US012708672B2

(12) United States Patent
Li et al.

(10) Patent No.: US 12,708,672 B2
(45) Date of Patent: Aug. 18, 2026

(54) VACCINE AND USES THEREOF IN CELL THERAPY

(71) Applicants: Innovative Cellular Therapeutics Holdings, Ltd., George Town (KY); Innovative Cellular Therapeutics, Inc., Rockville, MD (US)

(72) Inventors: Yang Li, Shanghai (CN); Zhiyuan Cao, Shanghai (CN); Wei Ding, Shanghai (CN); Xianyang Jiang, Shanghai (CN); Chengfei Pu, Shanghai (CN); Le Tian, Rockville, MD (US); Christopher Ballas, Rockville, MD (US); Zhao Wu, Shanghai (CN); Lei Xiao, Rockville, MD (US)

(73) Assignees: Innovative Cellular Therapeutics Holdings, Ltd., George Town (KY); Innovative Cellular Therapeutics, Inc., Rockville, MD (US)

( * ) Notice: Subject to any disclaimer, the term of this patent is extended or adjusted under 35 U.S.C. 154(b) by 598 days.

(21) Appl. No.: 18/194,349

(22) Filed: Mar. 31, 2023

(65) Prior Publication Data

US 2023/0226113 A1 Jul. 20, 2023

Related U.S. Application Data

(63) Continuation of application No. 17/592,601, filed on Feb. 4, 2022, now Pat. No. 11,633,427.

(60) Provisional application No. 63/250,440, filed on Sep. 30, 2021, provisional application No. 63/229,752, filed on Aug. 5, 2021, provisional application No. 63/154,446, filed on Feb. 26, 2021, provisional application No. 63/146,331, filed on Feb. 5, 2021.

(51) Int. Cl.

| | |
|---|---|
| ***A61K 35/17*** | (2025.01) |
| ***A61K 40/11*** | (2025.01) |
| ***A61K 40/31*** | (2025.01) |
| ***A61K 40/42*** | (2025.01) |
| ***A61K 47/69*** | (2017.01) |
| ***C07K 14/705*** | (2006.01) |

(52) U.S. Cl.

CPC .......... *A61K 47/6911* (2017.08); *A61K 40/11* (2025.01); *A61K 40/31* (2025.01); *A61K 40/42* (2025.01); *A61K 40/4211* (2025.01); *A61K 40/4244* (2025.01); *C07K 14/7051* (2013.01); *A61K 2239/30* (2023.05)

(58) Field of Classification Search

None

See application file for complete search history.

(56) References Cited

U.S. PATENT DOCUMENTS

| | | | | |
|---|---|---|---|---|
| 2022/0000921 | A1 | 1/2022 | Xiao | |
| 2023/0226113 | A1 * | 7/2023 | Li | A61K 40/31 424/93.71 |

OTHER PUBLICATIONS

Neal, et al., "The Basics of Artificial Antigen Presenting Cells in T Cell-Based Cancer Immunotherapies," 2017. J Immunol Res Ther. 2(1):68-79.

Schmidts, et al., "Cell-based artificial APC resistant to lentiviral transduction for efficient generation of CAR-T cells from various cell sources," Jul. 2020. J. ImmunoTher. Cancer, 8(2):10 pages.

PCT Communication mailed May 11, 2023 for PCT Application No. PCT/US23/61948, "Lipid Nanoparticle (LNP) and Uses thereof in Cell Therapy", 2 pages.

PCT Search Report and Written Opinion mailed Jul. 19, 2023 for PCT Application No. PCT/US23/61948, "Lipid Nanoparticle (LNP) and Uses thereof in Cell Therapy", 18 pages.

* cited by examiner

*Primary Examiner* — Michael D Burkhart

(74) *Attorney, Agent, or Firm* — Lee & Hayes, P.C.

(57) ABSTRACT

The present disclosure relates to compositions and methods for enhancing T cell response in vivo. For example, a method of enhancing T cell response in a subject or treating a subject having cancer, the method comprising: administering an effective amount of a composition comprising modified cells to the subject having a form of cancer associated with or expressing an antigen, for example, a solid tumor antigen; and administering (1) a nucleic acid encoding the antigen, (2) additional modified cells comprising the nucleic acid or the antigen, or (3) microorganisms, for example cold viruses, comprising the nucleic acid or the antigen. In embodiments, the modified cells comprise mixed cells targeting a solid tumor antigen and a white blood cell (WBC) antigen. In embodiments, the modified cells comprise a dominant negative form of an immune checkpoint molecule (e.g., PD-1). In embodiments, the modified cells comprise an exogenous polynucleotide encoding a therapeutic agent, such as IL-12 and IFNγ.

19 Claims, 25 Drawing Sheets

Specification includes a Sequence Listing.

Embodiment of conditional Activation

A: Antigen (e.g., GCC)
B: Notch

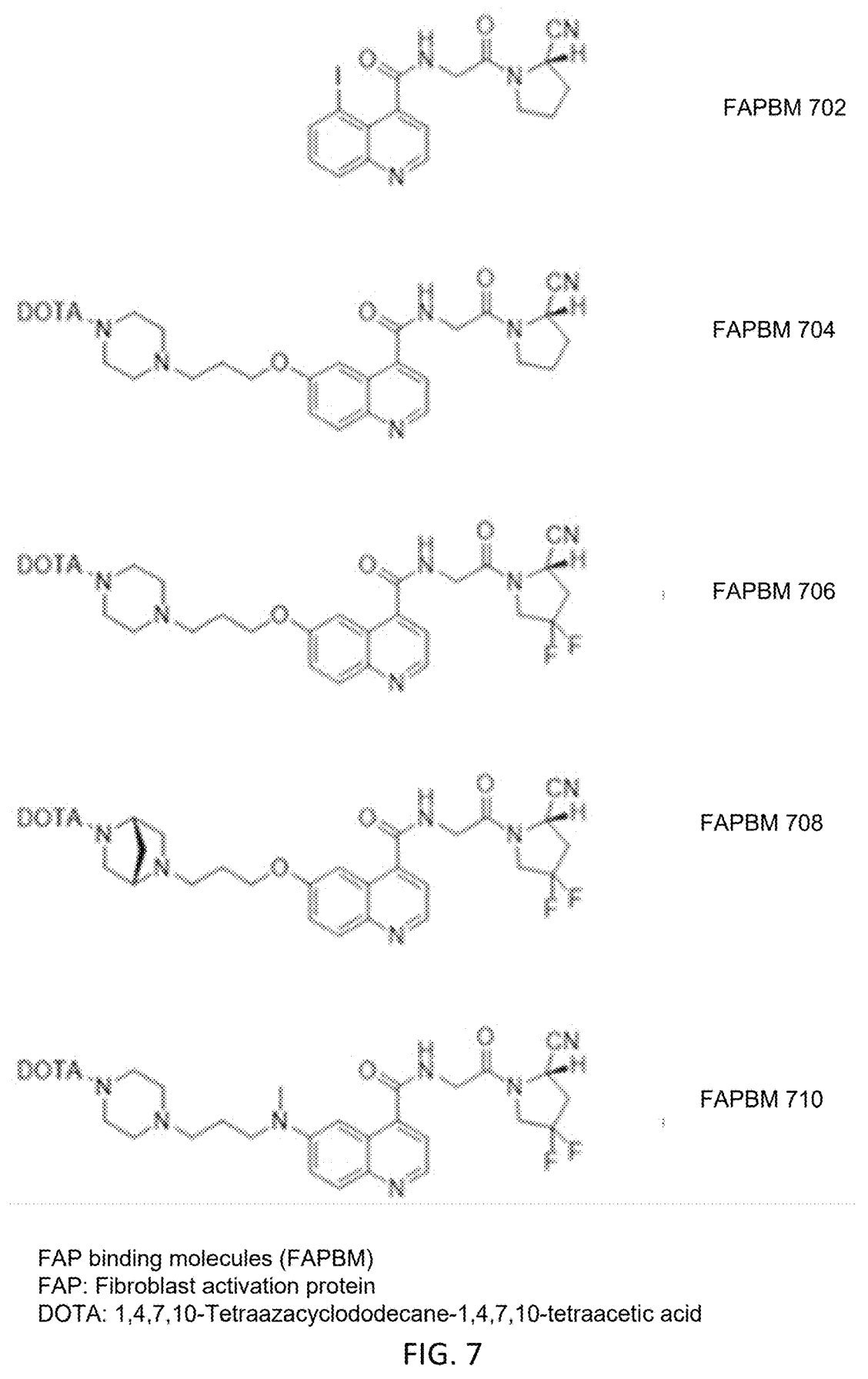

FAPBM 702

DOTA

FAPBM 704

DOTA

FAPBM 706

DOTA

FAPBM 708

DOTA

FAPBM 710

FAP binding molecules (FAPBM)
FAP: Fibroblast activation protein
DOTA: 1,4,7,10-Tetraazacyclododecane-1,4,7,10-tetraacetic acid

FIG. 7

GCC-LNP 100nm Size Distribution Report by Intensity v2.2

GFP-LNP 100nm Size Distribution Report by Intensity v2.2

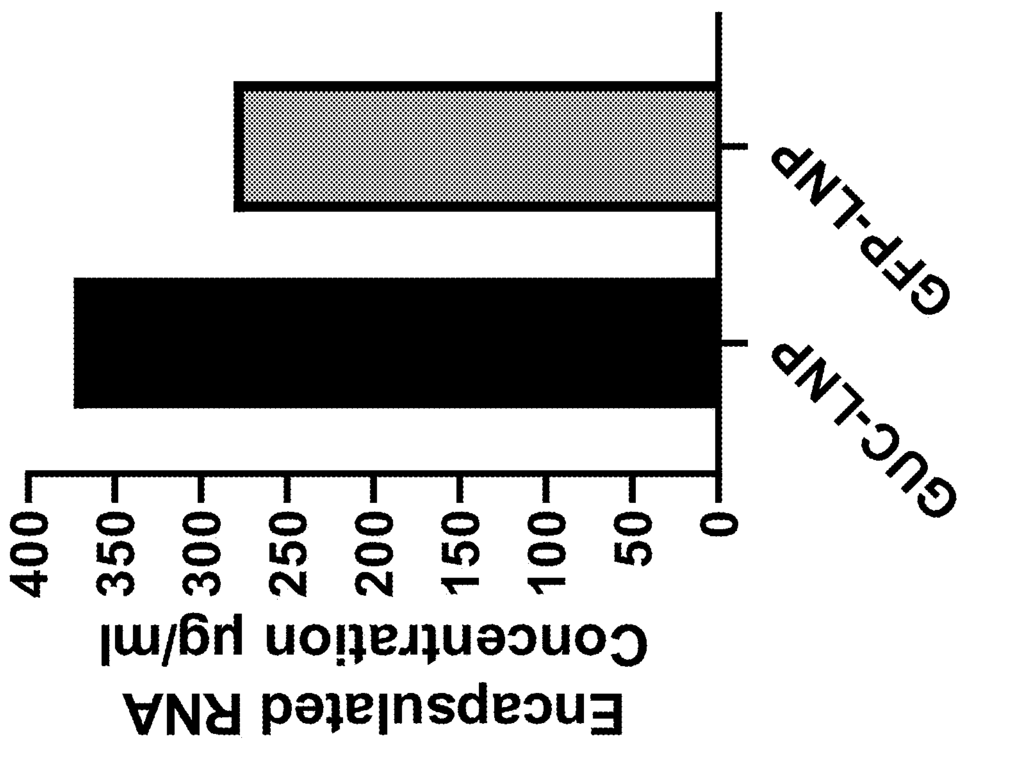
FIG. 20
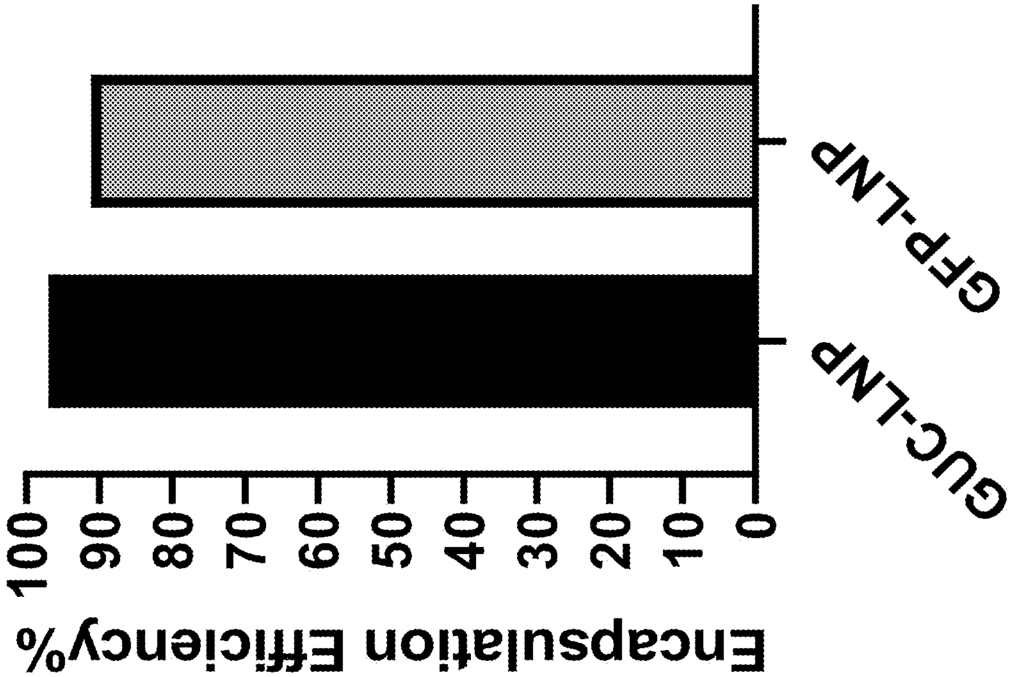

FIG. 25A
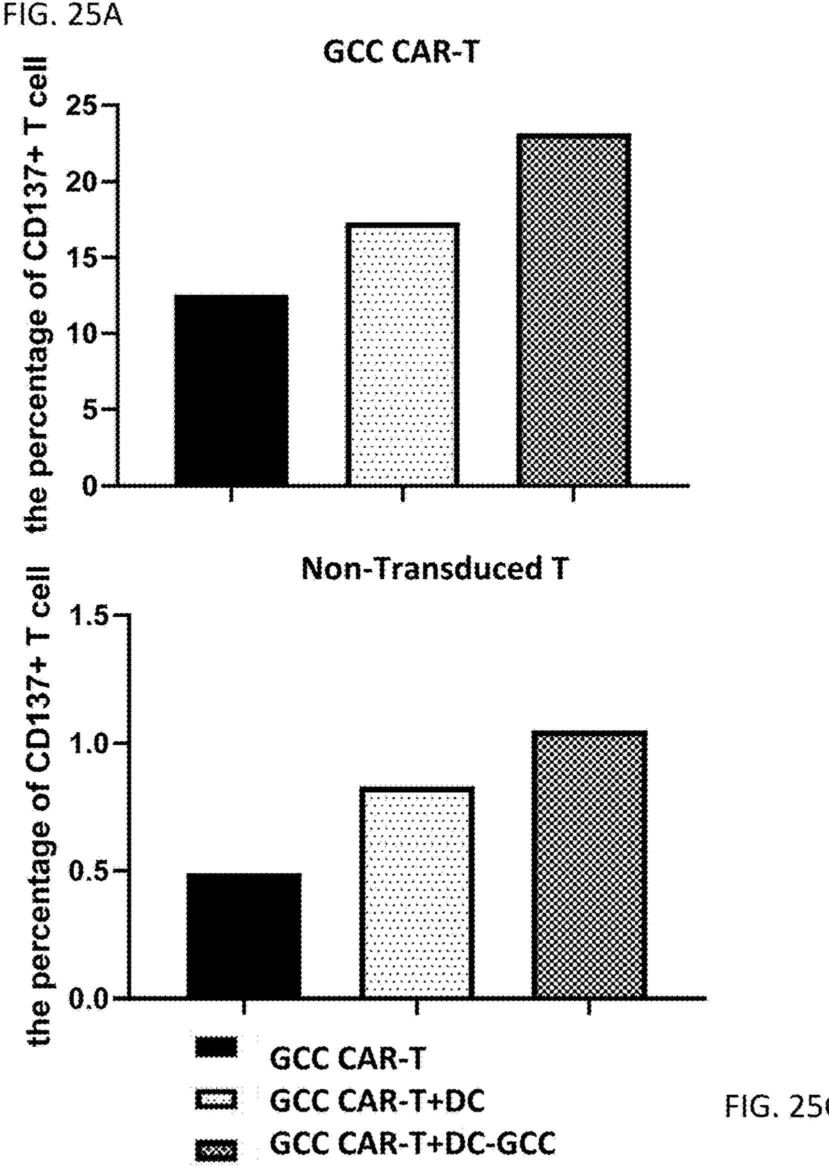
FIG. 25C
FIG. 25B
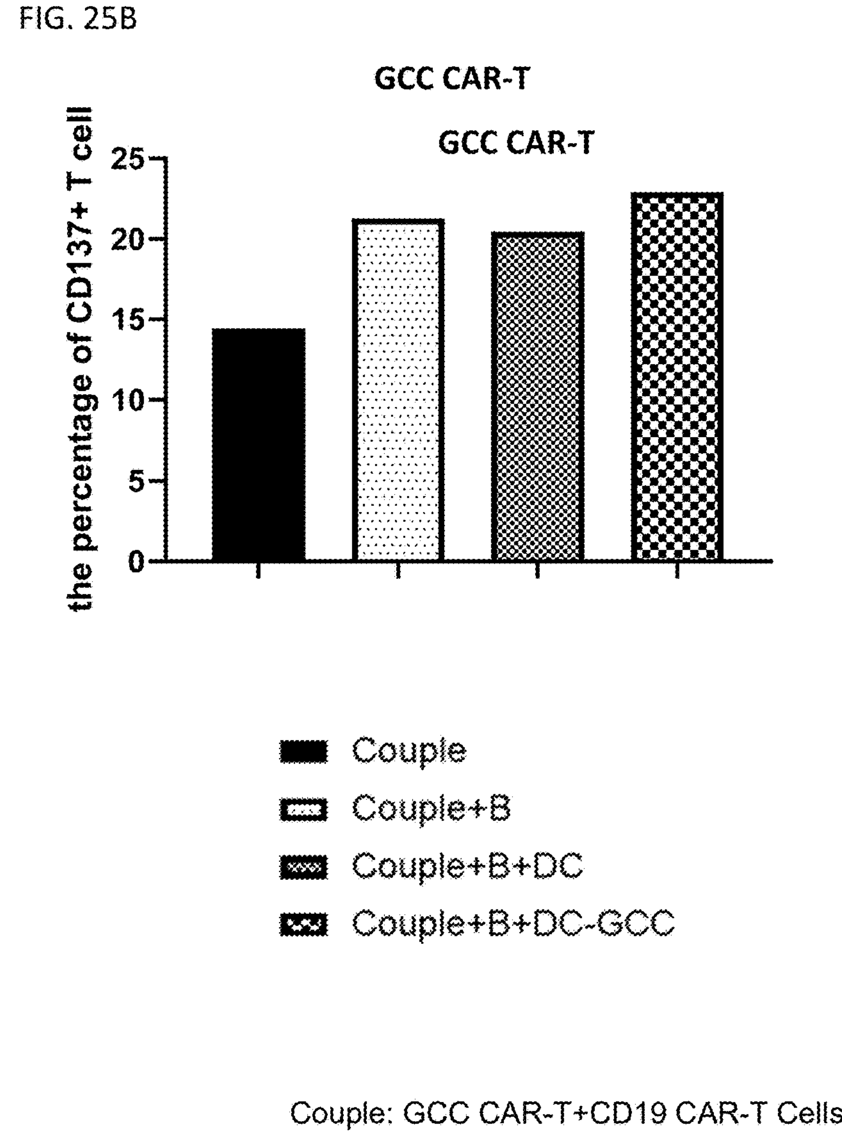

SEQUENCE LISTING

```
Sequence total quantity: 24
SEQ ID NO: 1            moltype = AA  length = 1073
FEATURE                 Location/Qualifiers
REGION                  1..1073
                        note = Synthesized
source                  1..1073
                        mol_type = protein
                        organism = synthetic construct
SEQUENCE: 1
```

-continued

```
MKTLLLDLAL WSLLFQPGWL SFSSQVSQNC HNGSYEISVL MMGNSAFAEP LKNLEDAVNE  60
GLEIVRGRLQ NAGLNVTVNA TFMYSDGLIH NSGDCRSSTC EGLDLLRKIS NAQRMGCVLI  120
GPSCTYSTFQ MYLDTELSYP MISAGSFGLS CDYKETLTRL MSPARKLMYF LVNFWKTNDL  180
PFKTYSWSTS YVYKNGTETE DCFWYLNALE ASVSYFSHEL GFKVVLRQDK EFQDILMDHN  240
RKSNVIIMCG GPEFLYKLKG DRAVAEDIVI ILVDLFNDQY FEDNVTAPDY MKNVLVLTLS  300
PGNSLLNSSF SRNLSPTKRD FALAYLNGIL LFGHMLKIFL ENGENITTPK FAHAFRNLTF  360
EGYDGPVTLD DWGDVDSTMV LLYTSVDTKK YKVLLTYDTH VNKTYPVDMS PTFTWKNSKL  420
PNDITGRGPQ ILMIAVFTLT GAVVLLLLVA LLMLRKYRKD YELRQKKWSH IPPENIFPLE  480
TNETNHVSLK IDDDKRRDTI QRLRQCKYDK KRVILKDLKH NDGNFTEKQK IELNKLLQID  540
YYNLTKFYGT VKLDTMIFGV IEYCERGSLR EVLNDTISYP DGTFMDWEFK ISVLYDIAKG  600
MSYLHSSKTE VHGRLKSTNC VVDSRMVVKI TDFGCNSILP PKKDLWTAPE HLRQANISQK  660
GDVYSYGIIA QEIILRKETF YTLSCRDRNE KIFRVENSNG MKPFRPDLFL ETAEEKELEV  720
YLLVKNCWEE DPEKRPDFKK IETTLAKIFG LFHDQKNESY MDTLIRRLQL YSRNLEHLVE  780
ERTQLYKAER DRADRLNFML LPRLVVKSLK EKGFVEPELY EEVTIYFSDI VGFTTICKYS  840
TPMEVVDMLN DIYKSFDHIV DHHDVYKVET IGDAYMVASG LPKRNGNRHA IDIAKMALEI  900
LSFMGTFELE HLPGLPIWIR IGVHSGPCAA GVVGIKMPRY CLFGDTVNTA SRMESTGLPL  960
RIHVSGSTIA ILKRTECQFL YEVRGETYLK GRGNETTYWL TGMKDQKFNL PTPPTVENQQ  1020
RLQAEFSDMI ANSLQKRQAA GIRSQKPRRV ASYKKGTLEY LQLNTTDKES TYF         1073

SEQ ID NO: 2           moltype = DNA  length = 3858
FEATURE                Location/Qualifiers
misc_feature           1..3858
                       note = Synthesized
source                 1..3858
                       mol_type = other DNA
                       organism = synthetic construct
SEQUENCE: 2
gaccagttgg gcatgaccag agagaagcgt ggggaagagt gggctgaggg actccactag  60
aggctgtcca tctggattcc ctgcctccct aggagcccaa cagagcaaag caagtgggca  120
caaggagtat ggttctaacg tgattggggt catgaagacg ttgctgttgg acttggcttt  180
gtggtcactg ctcttccagc ccgggtggct gtcctttagt tcccaggtga gtcagaactg  240
ccacaatggc agctatgaaa tcagcgtcct gatgatgggc aactcagcct ttgcagagcc  300
cctgaaaaac ttggaagatg cggtgaatga ggggctggaa atagtgagag gacgtctgca  360
aaatgctggc ctaaatgtga ctgtgaacgc tactttcatg tattcggatg gtctgattca  420
taactcaggc gactgccgga gtagcacctg tgaaggcctc gacctactca ggaaaatttc  480
aaatgcacaa cggatgggct gtgtcctcat agggccctca tgtacatact ccaccttcca  540
gatgtacctt gacacagaat tgagctaccc catgatctca gctggaagtt ttggattgtc  600
atgtgactat aaagaaacct taaccaggct gatgtctcca gctagaaagt tgatgtactt  660
cttggttaac ttttggaaaa ccaacgatct gcccttcaaa acttattcct ggagcacttc  720
gtatgtttac aagaatggta cagaaactga ggactgtttc tggtacctta atgctctgga  780
ggctagcgtt tcctatttct cccacgaact cggctttaag gtggtgttaa gacaagataa  840
ggagtttcag gatatcttaa tggaccacaa caggaaaagc aatgtgatta ttatgtgtgg  900
tggtccagag ttcctctaca agctgaaggg tgaccgagca gtggctgaag acattgtcat  960
tattctagtg gatcttttca atgaccagta ctttgaggac aatgtcacag cccctgacta  1020
tatgaaaaat gtccttgttc tgacgctgtc tcctgggaat tcccttctaa atagctcttt  1080
ctccaggaat ctatcaccaa caaaacgaga ctttgctctt gcctatttga atggaatcct  1140
gctctttgga catatgctga agatatttct tgaaaatgga gaaaatatta ccaccccaa  1200
atttgctcat gctttcagga atctcacttt tgaagggtat gacggtccag tgaccttgga  1260
tgactggggg gatgttgaca gtaccatggt gcttctgtat acctctgtgg acaccaagaa  1320
atacaaggtt cttttgacct atgataccca cgtaaataag acctatcctg tggatatgag  1380
ccccacattc acttggaaga actctaaact tcctaatgat attacaggcc ggggccctca  1440
gatcctgatg attgcagtct tcaccctcac tggagctgtg gtgctgctcc tgctcgtcgc  1500
tctcctgatg ctcagaaaat atagaaaaga ttatgaactt cgtcagaaaa aatggtccca  1560
cattcctcct gaaaatatct ttcctctgga gaccaatgag accaatcatg ttagcctcaa  1620
gatcgatgat gacaaaagac gagatacaat ccagagacta cgacagtgca aatacgacaa  1680
aaagcgagtg attctcaaag atctcaagca caatgatggt aatttcactg aaaaacagaa  1740
gatagaattg aacaagttgc ttcagattga ctattacaac ctgaccaagt tctacggcac  1800
agtgaaactt gataccatga tcttcggggt gatagaatac tgtgagagag gatccctccg  1860
ggaagtttta aatgacacaa tttcctaccc tgatggcaca ttcatggatt gggagtttaa  1920
gatctctgtc ttgtatgaca ttgctaaggg aatgtcatat ctgcactcca gtaagacaga  1980
agtccatggt cgtctgaaat ctaccaactg cgtagtggac agtagaatgg tggtgaagat  2040
cactgatttt ggctgcaatt ccattttacc tccaaaaaag gacctgtgga cagctccaga  2100
gcacctccgc caagccaaca tctctcagaa aggagatgtg tacagctatg ggatcatcgc  2160
acaggagatc atcctgcgga aagaaacctt ctacactttg agctgtcggg accggaatga  2220
gaagatttc agagtggaaa attccaatgg aatgaaaccc ttccgcccag atttattctt  2280
ggaaacagca gaggaaaaag agctagaagt gtacctactt gtaaaaaact gttgggagga  2340
agatccagaa aagagaccag atttcaaaaa aattgagact acacttgcca agatatttgg  2400
actttttcat gaccaaaaaa atgaaagcta tatggatacc ttgatccgac gtctacagct  2460
atattctcga aacctggaac atctggtaga ggaaaggaca cagctgtaca aggcagagag  2520
ggacagggct gacagactta actttatgtt gcttccaagg ctagtggtaa agtctctgaa  2580
ggagaaaggc tttgtggagc cggaactata tgaggaagtt acaatctact tcagtgacat  2640
tgtaggtttc actactatct gcaaatacag cacccccatg gaagtggtgg acatgcttaa  2700
tgacatctat aagagttttg accacattgt tgatcatcat gatgtctaca aggtggaaac  2760
catcggtgat gcgtacatgg tggctagtgg tttgcctaag agaaatggca atcggcatgc  2820
aatagacatt gccaagatgg ccttggaaat cctcagcttc atggggacct ttgagctgga  2880
gcatcttcct ggcctcccaa tatggattcg cattggagtt cactctggtc cctgtgctgc  2940
tggagttgtg ggaatcaaga tgcctcgtta ttgtctattt ggagatacgg tcaacacagc  3000
ctctaggatg gaatccactg gcctcccttt gagaattcac gtgagtggct ccaccatagc  3060
catcctgaag agaactgagt gccagttcct ttatgaagtg agaggagaaa catacttaaa  3120
```

```
gggaagagga aatgagacta cctactggct gactgggatg aaggaccaga aattcaacct  3180
gccaacccct cctactgtgg agaatcaaca gcgtttgcaa gcagaatttt cagacatgat  3240
tgccaactct ttacagaaaa gacaggcagc agggataaga agccaaaaac ccagacgggt  3300
agccagctat aaaaaaggca ctctggaata cttgcagctg aataccacag acaaggagag  3360
cacctatttt taaacctaaa tgaggtataa ggactcacac aaattaaaat acagctgcac  3420
tgaggcagcg acctcaagtg tcctgaaagc ttacattttc ctgagacctc aatgaagcag  3480
aaatgtactt aggcttggct gccctgtctg gaacatggac tttcttgcat gaatcagatg  3540
tgtgttctca gtgaaataac taccttccac tctggaacct tattccagca gttgttccag  3600
ggagcttcta cctggaaaag aaaagaaatg aatagactat ctagaacttg agaagatttt  3660
attcttattt catttatttt ttgtttgttt atttttatcg tttttgttta ctggctttcc  3720
ttctgtattc ataagatttt ttaaattgtc ataattatat tttaaatacc catcttcatt  3780
aaagtatatt taactcataa tttttgcaga aaatatgcta tatattaggc aagaataaaa  3840
gctaaaggtt tcccaaaa                                                3858

SEQ ID NO: 3            moltype = AA  length = 238
FEATURE                 Location/Qualifiers
REGION                  1..238
                        note = Synthesized
source                  1..238
                        mol_type = protein
                        organism = synthetic construct
SEQUENCE: 3
MSKGEELFTG VVPILVELDG DVNGHKFSVS GEGEGDATYG KLTLKFICTT GKLPVPWPTL  60
VTTLTYGVQC FSRYPDHMKQ HDFFKSAMPE GYVQERTIFF KDDGNYKTRA EVKFEGDTLV  120
NRIELKGIDF KEDGNILGHK LEYNYNSHNV YIMADKQKNG IKVNFKIRHN IEDGSVQLAD  180
HYQQNTPIGD GPVLLPDNHY LSTQSALSKD PNEKRDHMVL LEFVTAAGIT HGMDELYK    238

SEQ ID NO: 4            moltype = DNA  length = 1269
FEATURE                 Location/Qualifiers
misc_feature            1..1269
                        note = Synthesized
source                  1..1269
                        mol_type = other DNA
                        organism = synthetic construct
SEQUENCE: 4
gctagcggga actgccagac atcaaataaa acaaaaggct cagtcggaag actgggcctt  60
ttgttttatc tgttgtttgt cggtgaacac tctcccgaaa gcaagctgat aaaccgatac  120
aattaaaggc tccttttgga gccttttttt ttggagattt tcaacatgaa aaaattatta  180
tttgatgatc agatagcggc ggggaactgc cagacatcaa ataaaacaaa aggctcagtc  240
ggaagactgg gccttttgtt ttatctgttg tttgtcggtg aacactctcc cgactagtcg  300
cccccggagg ctttcccggg gcaaatcact cgaggaggct cttcaatgtc caagggcgag  360
gaactgttca cgggcgtcgt cccgatcctc gtcgaactcg atggcgacgt caacggccac  420
aagttctccg tcagcggtga aggtgaaggc gacgccacct acggcaagct caccettaag  480
ttcatctgca ccaccggcaa actgccggtg ccgtggccga cgctggtcac gaccctcacg  540
tatggcgttc agtgcttctc gcgctacccg gaccacatga agcagcacga tttcttcaag  600
tcggcgatgc cggaaggcta cgtccaggaa cgcacgatct tcttcaagga cgatggcaac  660
tacaagaccc gcgccgaagt caagttcgag ggcgacacgc ttgtgaatcg catcgaactt  720
aagggcatcg acttcaagga agatggcaac atcctcggcc acaagctgga gtataactac  780
aattcgcaca acgtctacat catggctgac aagcagaaga atggtatcaa ggttaacttc  840
aagatccgcc acaacatcga agacggctcc gtccagctgg cggaccacta tcagcagaac  900
accccgatcg gcgacggccc ggttctcctc ccggataacc actacctcag cacgcagtcg  960
gcgctgtcga aggacccgaa tgaaaagcgc gaccacatgg tccttctgga gttcgtgacc  1020
gcggcgggca tcacgcacgg catggacgaa ctttacaagt aatctagacg gtcagtttca  1080
cctgatttac gtaaaaaccc gcttcggcgg gtttttgctt ttggaggggc agaaagatga  1140
atgactgtct gacaaatgct ctttccctaa actcccccca taaaaaaacc cgccgaagcg  1200
ggtttttacg ttatttgcgg attaacgatt actgatttgc ccgggaaaaa gcctccgggg  1260
gcgggtacc                                                          1269

SEQ ID NO: 5            moltype = AA  length = 241
FEATURE                 Location/Qualifiers
REGION                  1..241
                        note = Synthesized
source                  1..241
                        mol_type = protein
                        organism = synthetic construct
SEQUENCE: 5
EIVMTQSPAT LSVSPGERAT LSCRASQSVS RNLAWYQQKP GQAPRLLIYG ASTRATGIPA  60
RFSGSGSGTE FTLTIGSLQS EDFAVYYCQQ YKTWPRTFGQ GTNVEIKGGG GSGGGGSGGG  120
GSQVQLQQWG AGLLKPSETL SLTCAVFGGS FSGYYWSWIR QPPGKGLEWI GEINHRGNTN  180
DNPSLKSRVT ISVDTSKNQF ALKLSSVTAA DTAVYYCARE RGYTYGNFDH WGQGTLVTVS  240
S                                                                  241

SEQ ID NO: 6            moltype = AA  length = 485
FEATURE                 Location/Qualifiers
REGION                  1..485
                        note = Synthesized
source                  1..485
                        mol_type = protein
                        organism = synthetic construct
```

-continued

```
SEQUENCE: 6
MALPVTALLL PLALLLHAAR PEIVMTQSPA TLSVSPGERA TLSCRASQSV SRNLAWYQQK  60
PGQAPRLLIY GASTRATGIP ARFSGSGSGT EFTLTIGSLQ SEDFAVYYCQ QYKTWPRTFG  120
QGTNVEIKGG GGSGGGGSGG GGSQVQLQQW GAGLLKPSET LSLTCAVFGG SFSGYYWSWI  180
RQPPGKGLEW IGEINHRGNT NDNPSLKSRV TISVDTSKNQ FALKLSSVTA ADTAVYYCAR  240
ERGYTYGNFD HWGQGTLVTV SSAKPTTTPA PRPPTPAPTI ASQPLSLRPE ACRPAAGGAV  300
HTRGLDFACD IYIWAPLAGT CGVLLLSLVI TKRGRKKLLY IFKQPFMRPV QTTQEEDGCS  360
CRFPEEEEGG CELRVKFSRS ADAPAYKQGQ NQLYNELNLG RREEYDVLDK RRGRDPEMGG  420
KPRRKNPQEG LYNELQKDKM AEAYSEIGMK GERRRGKGHD GLYQGLSTAT KDTYDALHMQ  480
ALPPR                                                             485

SEQ ID NO: 7          moltype = AA  length = 288
FEATURE               Location/Qualifiers
REGION                1..288
                      note = Synthesized
source                1..288
                      mol_type = protein
                      organism = synthetic construct
SEQUENCE: 7
MGHTRRQGTS PSKCPYLNFF QLLVLAGLSH FCSGVIHVTK EVKEVATLSC GHNVSVEELA  60
QTRIYWQKEK KMVLTMMSGD MNIWPEYKNR TIFDITNNLS IVILALRPSD EGTYECVVLK  120
YEKDAFKREH LAEVTLSVKA DFPTPSISDF EIPTSNIRRI ICSTSGGFPE PHLSWLENGE  180
ELNAINTTVS QDPETELYAV SSKLDFNMTT NHSFMCLIKY GHLRVNQTFN WNTTKQEHFP  240
DNLLPSWAIT LISVNGIFVI CCLTYCFAPR CRERRRNERL RRESVRPV              288

SEQ ID NO: 8          moltype = AA  length = 329
FEATURE               Location/Qualifiers
REGION                1..329
                      note = Synthesized
source                1..329
                      mol_type = protein
                      organism = synthetic construct
SEQUENCE: 8
MDPQCTMGLS NILFVMAFLL SGAAPLKIQA YFNETADLPC QFANSQNQSL SELVVFWQDQ  60
ENLVLNEVYL GKEKFDSVHS KYMGRTSFDS DSWTLRLHNL QIKDKGLYQC IIHHKKPTGM  120
IRIHQMNSEL SVLANFSQPE IVPISNITEN VYINLTCSSI HGYPEPKKMS VLLRTKNSTI  180
EYDGVMQKSQ DNVTELYDVS ISLSVSFPDV TSNMTIFCIL ETDKTRLLSS PFSIELEDPQ  240
PPPDHIPWIT AVLPTVIICV MVFCLILWKW KKKKRPRNSY KCGTNTMERE ESEQTKKREK  300
IHIPERSDEA QRVFKSSKTS SCDKSDTCF                                   329

SEQ ID NO: 9          moltype = AA  length = 254
FEATURE               Location/Qualifiers
REGION                1..254
                      note = Synthesized
source                1..254
                      mol_type = protein
                      organism = synthetic construct
SEQUENCE: 9
MEYASDASLD PEAPWPPAPR ARACRVLPWA LVAGLLLLLL LAAACAVFLA CPWAVSGARA  60
SPGSAASPRL REGPELSPDD PAGLLDLRQG MFAQLVAQNV LLIDGPLSWY SDPGLAGVSL  120
TGGLSYKEDT KELVVAKAGV YYVFFQLELR RVVAGEGSGS VSLALHLQPL RSAAGAAALA  180
LTVDLPPASS EARNSAFGFQ GRLLHLSAGQ RLGVHLHTEA RARHAWQLTQ GATVLGLFRV  240
TPEIPAGLPS PRSE                                                   254

SEQ ID NO: 10         moltype = AA  length = 111
FEATURE               Location/Qualifiers
REGION                1..111
                      note = Synthesized
source                1..111
                      mol_type = protein
                      organism = synthetic construct
SEQUENCE: 10
DIELTQSPAS LAVSLGQRAT ISCRASESVE YYVTSLMQWY QQKPGQPPKL LIFAASNVES  60
GVPARFSGSG SGTNFSLNIH PVDEDDVAMY FCQQSRKVPY TFGGGTKLEI K           111

SEQ ID NO: 11         moltype = AA  length = 120
FEATURE               Location/Qualifiers
REGION                1..120
                      note = Synthesized
source                1..120
                      mol_type = protein
                      organism = synthetic construct
SEQUENCE: 11
EVKLQQSGPG LVTPSQSLSI TCTVSGFSLS DYGVHWVRQS PGQGLEWLGV IWAGGGTNYN  60
SALMSRKSIS KDNSKSQVFL KMNSLQADDT AVYYCARDKG YSYYYSMDYW GQGTSVTVSS  120

SEQ ID NO: 12         moltype = AA  length = 121
FEATURE               Location/Qualifiers
REGION                1..121
```

```
                        note = Synthesized
source                  1..121
                        mol_type = protein
                        organism = synthetic construct
SEQUENCE: 12
QVQLQQWGAG LLKPSETLSL TCAVYGGSFS GYYWSWIRQS PEKGLEWIGE INHGGYVTYN  60
PSLESRVTIS VDTSKNFSLK LSSVTAADTA VYYCARDYGP GNYDWYFDLW GRGTLVTVSS  120
V                                                                 121

SEQ ID NO: 13           moltype = AA  length = 109
FEATURE                 Location/Qualifiers
REGION                  1..109
                        note = Synthesized
source                  1..109
                        mol_type = protein
                        organism = synthetic construct
SEQUENCE: 13
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPPALTF GGGTKVEIK             109

SEQ ID NO: 14           moltype = AA  length = 162
FEATURE                 Location/Qualifiers
REGION                  1..162
                        note = Synthesized
source                  1..162
                        mol_type = protein
                        organism = synthetic construct
SEQUENCE: 14
MRISKPHLRS ISIQCYLCLL LNSHFLTEAG IHVFILGCFS AGLPKTEANW VNVISDLKKI  60
EDLIQSMHID ATLYTESDVH PSCKVTAMKC FLLELQVISL ESGDASIHDT VENLIILANN  120
SLSSNGNVTE SGCKECEELE EKNIKEFLQS FVHIVQMFIN TS                    162

SEQ ID NO: 15           moltype = AA  length = 162
FEATURE                 Location/Qualifiers
REGION                  1..162
                        note = Synthesized
source                  1..162
                        mol_type = protein
                        organism = synthetic construct
SEQUENCE: 15
MRISKPHLRS ISIQCYLCLL LNSHFLTEAG IHVFILGCFS AGLPKTEANW VNVISDLKKI  60
EDLIQSMHID ATLYTESDVH PSCKVTAMKC FLLELQVISL ESGDASIHDT VENLIILANN  120
SLSSNGNVTE SGCKECEELE EKNIKEFLQS FVHIVQMFIN TS                    162

SEQ ID NO: 16           moltype = AA  length = 189
FEATURE                 Location/Qualifiers
REGION                  1..189
                        note = Synthesized
source                  1..189
                        mol_type = protein
                        organism = synthetic construct
SEQUENCE: 16
MLGSRAVMLL LLLPWTAQGR AVPGGSSPAW TQCQQLSQKL CTLAWSAHPL VGHMDLREEG  60
DEETTNDVPH IQCGDGCDPQ GLRDNSQFCL QRIHQGLIFY EKLLGSDIFT GEPSLLPDSP  120
VGQLHASLLG LSQLLQPEGH HWETQQIPSL SPSQPWQRLL LRFKILRSLQ AFVAVAARVF  180
AHGAATLSP                                                         189

SEQ ID NO: 17           moltype = AA  length = 328
FEATURE                 Location/Qualifiers
REGION                  1..328
                        note = Synthesized
source                  1..328
                        mol_type = protein
                        organism = synthetic construct
SEQUENCE: 17
MCHQQLVISW FSLVFLASPL VAIWELKKDV YVVELDWYPD APGEMVVLTC DTPEEDGITW  60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCS                                    328

SEQ ID NO: 18           moltype = AA  length = 219
FEATURE                 Location/Qualifiers
REGION                  1..219
                        note = Synthesized
source                  1..219
                        mol_type = protein
                        organism = synthetic construct
```

```
SEQUENCE: 18
MCPARSLLLV ATLVLLDHLS LARNLPVATP DPGMFPCLHH SQNLLRAVSN MLQKARQTLE  60
FYPCTSEEID HEDITKDKTS TVEACLPLEL TKNESCLNSR ETSFITNGSC LASRKTSFMM  120
ALCLSSIYED LKMYQVEFKT MNAKLLMDPK RQIFLDQNML AVIDELMQAL NFNSETVPQK  180
SSLEEPDFYK TKIKLCILLH AFRIRAVTID RVMSYLNAS                        219

SEQ ID NO: 19          moltype = AA  length = 193
FEATURE                Location/Qualifiers
REGION                 1..193
                       note = Synthesized
source                 1..193
                       mol_type = protein
                       organism = synthetic construct
SEQUENCE: 19
MAAEPVEDNC INFVAMKFID NTLYFIAEDD ENLESDYFGK LESKLSVIRN LNDQVLFIDQ  60
GNRPLFEDMT DSDCRDNAPR TIFIISMYKD SQPRGMAVTI SVKCEKISTL SCENKIISFK  120
EMNPPDNIKD TKSDIIFFQR SVPGHDNKMQ FESSSYEGYF LACEKERDLF KLILKKEDEL  180
GDRSIMFTVQ NED                                                    193

SEQ ID NO: 20          moltype = AA  length = 91
FEATURE                Location/Qualifiers
REGION                 1..91
                       note = Synthesized
source                 1..91
                       mol_type = protein
                       organism = synthetic construct
SEQUENCE: 20
MKVSAAALAV ILIATALCAP ASASPYSSDT TPCCFAYIAR PLPRAHIKEY FYTSGKCSNP  60
AVVFVTRKNR QVCANPEKKW VREYINSLEM S                                91

SEQ ID NO: 21          moltype = AA  length = 93
FEATURE                Location/Qualifiers
REGION                 1..93
                       note = Synthesized
source                 1..93
                       mol_type = protein
                       organism = synthetic construct
SEQUENCE: 21
MDRLQTALLV VLVLLAVALQ ATEAGPYGAN MEDSVCCRDY VRYRLPLRVV KHFYWTSDSC  60
PRPGVVLLTF RDKEICADPR VPWVKMILNK LSQ                              93

SEQ ID NO: 22          moltype = AA  length = 153
FEATURE                Location/Qualifiers
REGION                 1..153
                       note = Synthesized
source                 1..153
                       mol_type = protein
                       organism = synthetic construct
SEQUENCE: 22
MYRMQLLSCI ALSLALVTNS APTSSSTKKT QLQLEHLLLD LQMILNGINN YKNPKLTRML  60
TFKFYMPKKA TELKHLQCLE EELKPLEEVL NLAQSKNFHL RPRDLISNIN VIVLELKGSE  120
TTFMCEYADE TATIVEFLNR WITFCQSIIS TLT                              153

SEQ ID NO: 23          moltype = AA  length = 177
FEATURE                Location/Qualifiers
REGION                 1..177
                       note = Synthesized
source                 1..177
                       mol_type = protein
                       organism = synthetic construct
SEQUENCE: 23
MFHVSFRYIF GLPPLILVLL PVASSDCDIE GKDGKQYESV LMVSIDQLLD SMKEIGSNCL  60
NNEFNFFKRH ICDANKEGMF LFRAARKLRQ FLKMNSTGDF DLHLLKVSEG TTILLNCTGQ  120
VKGRKPAALG EAQPTKSLEE NKSLKEQKKL NDLCFLKRLL QEIKTCWNKI LMGTKEH     177

SEQ ID NO: 24          moltype = AA  length = 15
FEATURE                Location/Qualifiers
REGION                 1..15
                       note = Synthesized
source                 1..15
                       mol_type = protein
                       organism = synthetic construct
SEQUENCE: 24
GGGGSGGGGS GGGGS                                                  15
```

VACCINE AND USES THEREOF IN CELL THERAPY

CROSS REFERENCE TO RELATED PATENT APPLICATIONS

This application is a continuation of co-pending U.S. application Ser. No. 17/592,601 filed Feb. 4, 2022, which claims the benefit of U.S. Provisional Application 63/146,331, filed Feb. 5, 2021; U.S. Provisional Application 63/154,446, filed Feb. 26, 2021; U.S. Provisional Application 63/229,752, filed Aug. 5, 2021; and U.S. Provisional Application 63/250,440, filed Sep. 30, 2021, which are hereby incorporated by reference in their entirety.

SEQUENCE LISTING INFORMATION

A computer readable XML file, entitled "1071-0090USC1_ST26.xml," created on or about Mar. 31, 2023, with a file size of about 40,877 bytes, contains the sequence listing for this application and is hereby incorporated by reference in its entirety.

TECHNICAL FIELD

The present disclosure relates to compositions and methods for expanding and maintaining modified cells including genetically modified cells, and uses thereof in treating diseases, including cancer.

BACKGROUND

Cancer is known as malignant tumors involving abnormal cell growth invading or spreading to other parts of the body. In humans, there are more than one hundred types of cancer. One example is breast cancer occurring in the epithelial tissue of the breast. Since breast cancer cells lose the characteristics of normal cells, the connection between breast cancer cells is lost. Once cancer cells are exfoliated, they spread over the entire body via the blood and/or lymph systems, becoming life-threatening. Currently, breast cancer has become one of the common threats to women's physical and mental health. Although immunotherapy (e.g., CAR T) has been proven effective for treating some cancers, there is still a need to improve immunotherapy to treat more cancers, including those involving solid tumors, effectively.

SUMMARY

The present disclosure relates to compositions and methods for enhancing T cell response and/or CAR cell expansion and/or maintenance in vivo and/or in vitro. For example, a method of enhancing T cell response in a subject or treating a subject having cancer, the method comprising: administering an effective amount of a composition comprising modified cells to the subject having a form of cancer associated with or expressing an antigen, such as a solid tumor antigen; and administering one or more nucleic acids encoding the antigen or a variant thereof or administering an effective amount of a composition comprising additional modified cells comprising the one or more nucleic acids encoding the antigen or a variant thereof.

The present disclosure describes a method of enhancing the expansion of lymphocytes and/or overcoming tumor heterogeneity, the method comprising: obtaining lipid particles comprising a polynucleotide encoding the amino acid of SEQ ID NO: 1; contacting a population of antigen-presenting cells (APCs) and a population of lymphocytes with the lipid particles, the population of lymphocytes comprising a first population of lymphocytes comprising a chimeric antigen receptor (CAR) comprising the amino acid of SEQ ID NO: 5 or 6 and a second population of lymphocytes comprising a T cell Receptor (TCR), the second population of lymphocytes not comprising the CAR; and allowing expansion of the second populations of lymphocytes. In embodiments, the first population of lymphocytes further comprise a polynucleotide encoding IL-12, and a level of the expansion of the population of lymphocytes is greater than a level of expansion of a population of lymphocytes comprising the polynucleotide encoding the CAR without the polynucleotide encoding IL-12. Here, tumor heterogeneity refers to molecular variations between tumor cells. Examples of these cells comprise mixed tumor cells expressing different or different levels of tumor antigens or epitopes, mixed tumor cells expressing different or different levels of checkpoint inhibitors, and mixed cells comprising tumor cells and lymphocytes (M2 macrophage) that are associated with the tumor cells and/or promote, for example, tumor angiogenesis, metastasis, and immunosuppression. In embodiments, delivery of antigens to DCs enhances expansion of not only the corresponding CAR T cells that bind the antigens but also T cells that don't comprise the CAR (bystander T cells), which is surprising discovery. T cell response of these bystander T cells may help CAR T cells to overcome the tumor heterogeneity.

This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

FIG. 7 shows various fibroblast activation protein (FAP) binding molecules (FAPBM).

FIG. 20 shows GCC-LNP & GFP-LNP encapsulation efficiency and encapsulated RNA concentration.

FIGS. 25A, 25B, and 25C show activation of mixed CAR19 CAR T and GCC CAR T cells after mixed with DCs transfected with LNP-GCC.

DETAILED DESCRIPTION

Figure 1:
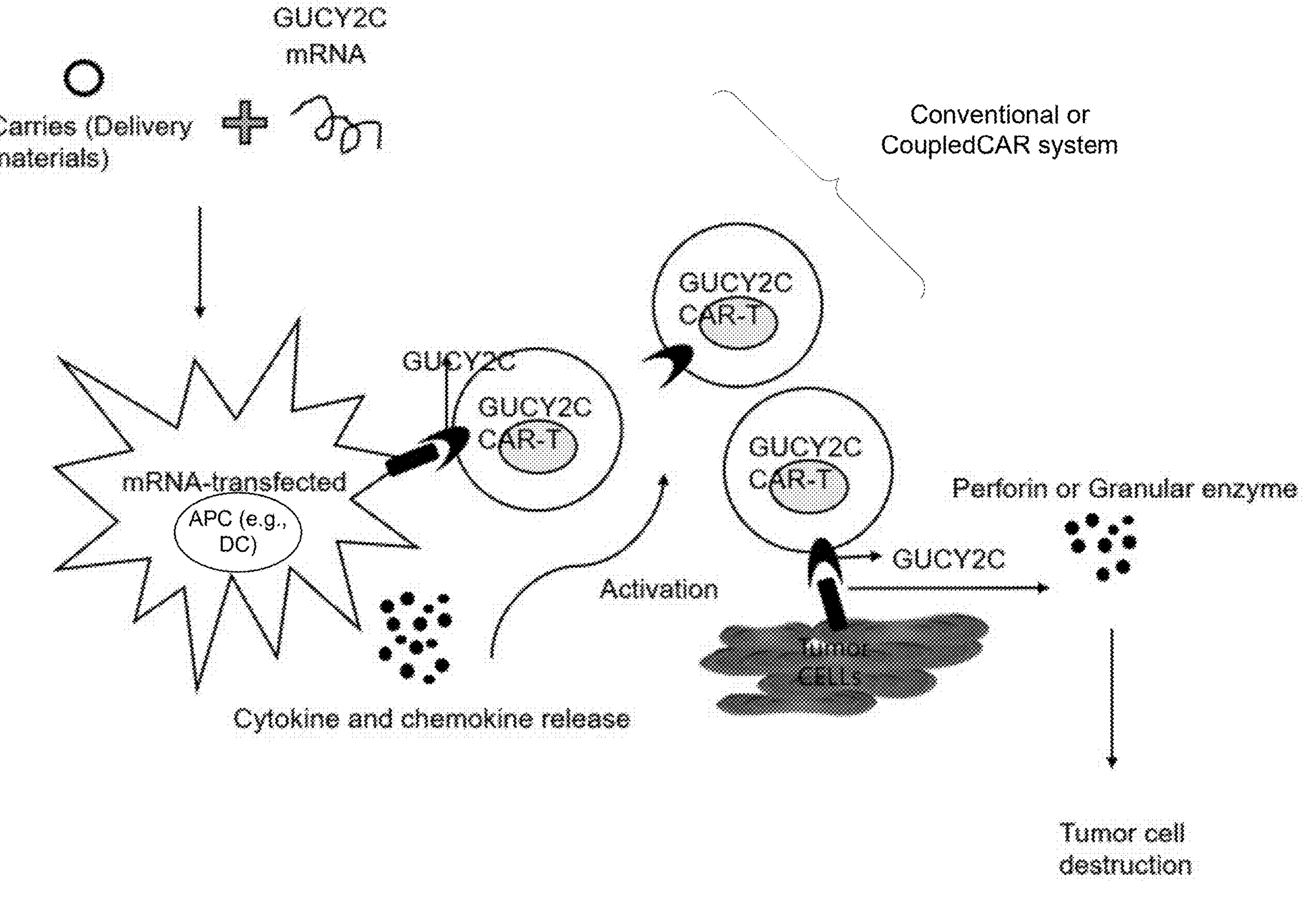
FIG. 1 is a schematic diagram of an exemplary combination of vaccines and cell therapies to treat cancer.
Figure 2:
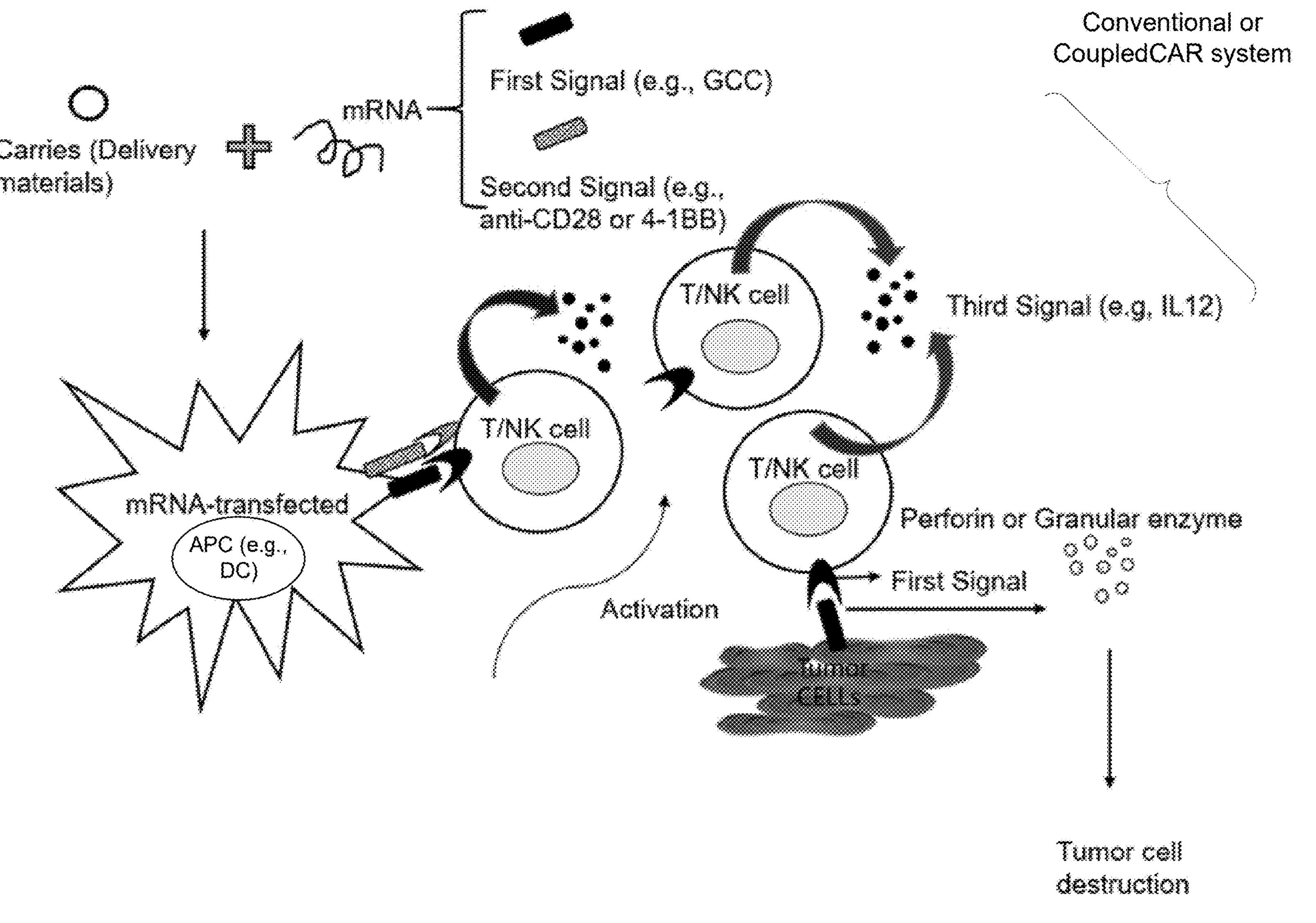
FIG. 2 is a schematic diagram of an exemplary combination of vaccines and cell therapies to treat cancer.
Figure 3:
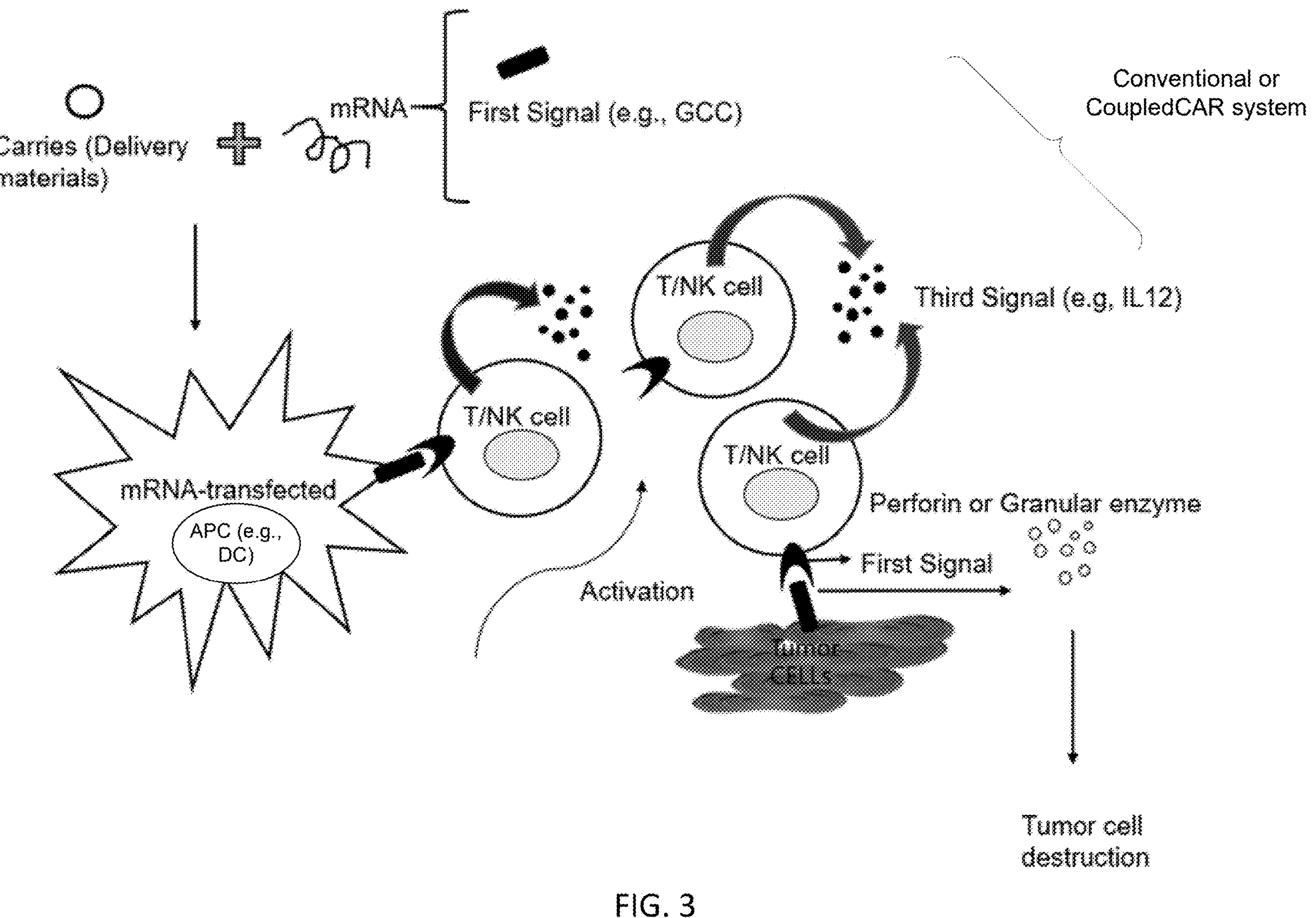
FIG. 3 is a schematic diagram of an exemplary combination of vaccines and cell therapies to treat cancer.
Figure 4:
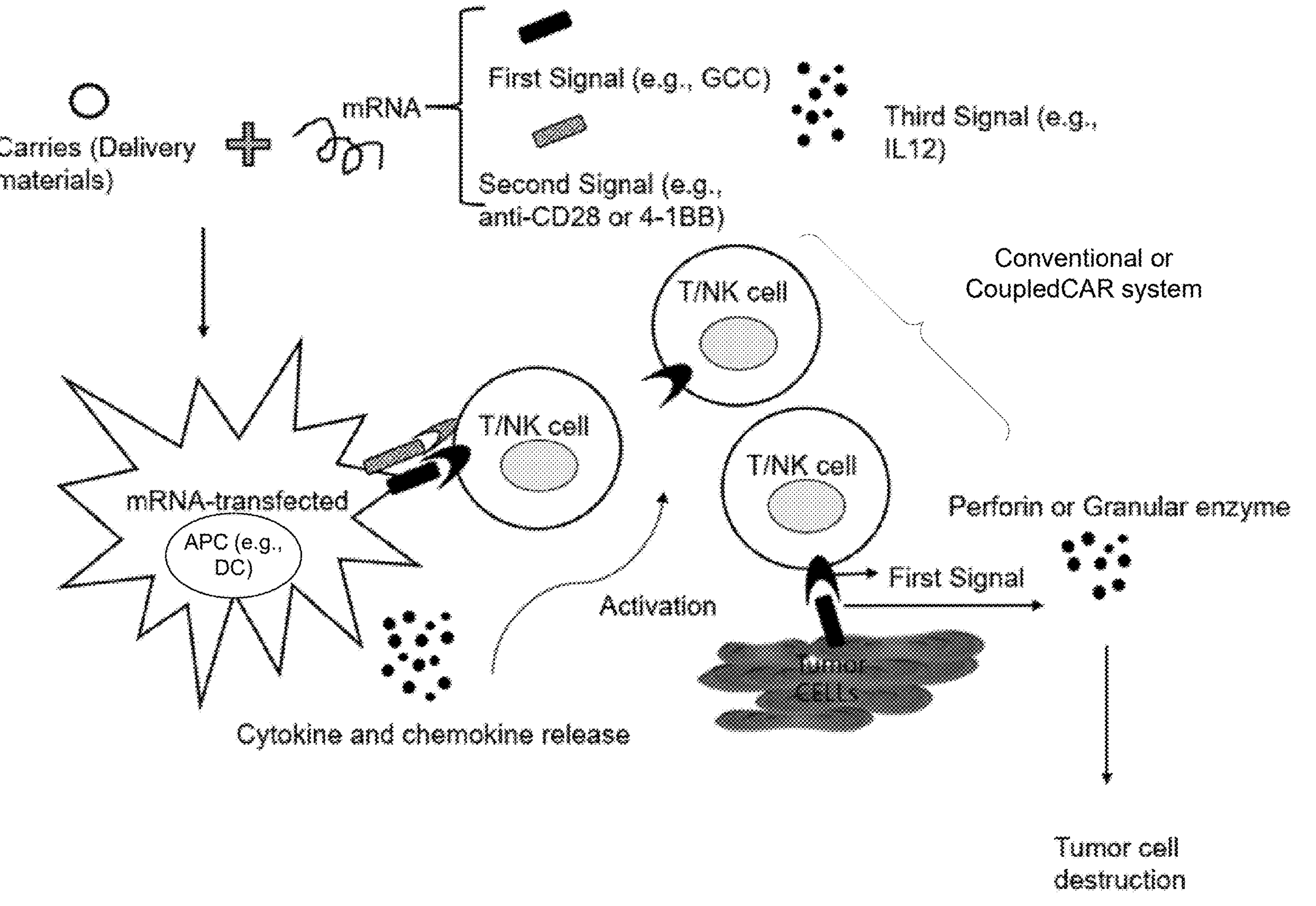
FIG. 4 is a schematic diagram of an exemplary combination of vaccines and cell therapies to treat cancer.
Figure 5:
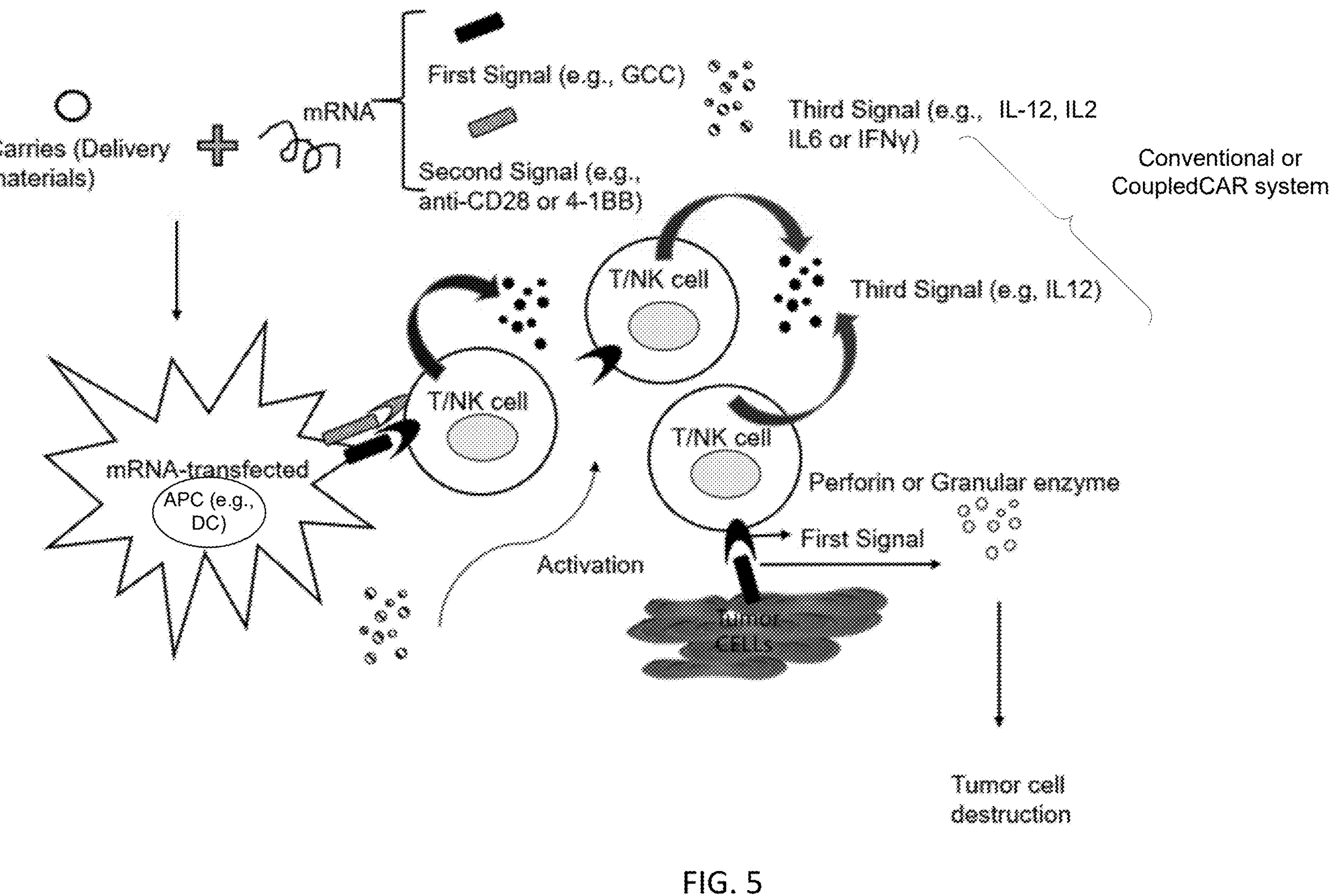
FIG. 5 is a schematic diagram of an exemplary combination of vaccines and cell therapies to treat cancer.
Figure 6:
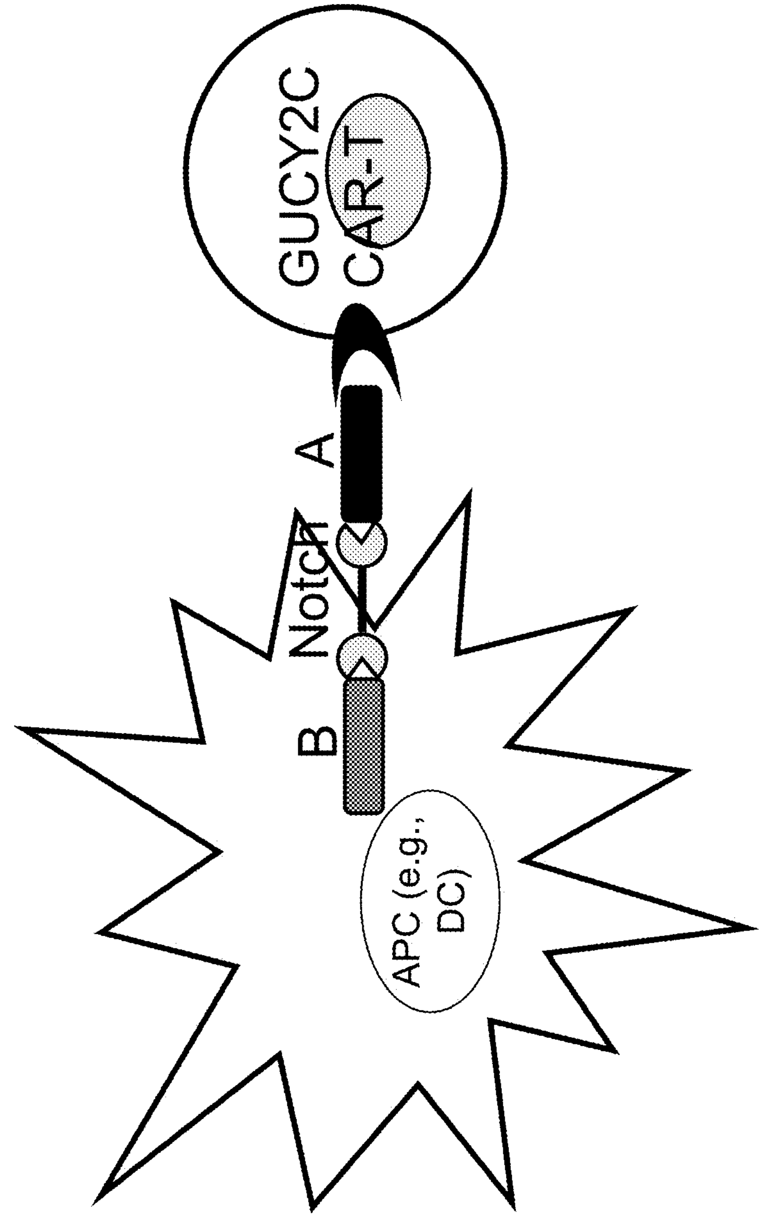
FIG. 6 is a schematic diagram of an exemplary combination of vaccines and cell therapies to treat cancer.

Unless defined otherwise, all technical and scientific terms used herein have the same meaning as commonly understood by those of ordinary skill in the art to which the disclosure belongs. Although any method and material similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multi-specific antibodies (e.g., bispecific antibodies), and antibody fragments so long as they exhibit the desired biological activity or function. The antibodies in the present disclosure may exist in a variety of forms including, for example, polyclonal antibodies; monoclonal antibodies; Fv, Fab, Fab', and F(ab') 2 fragments; as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragments" refers to a portion of a full-length antibody, for example, the antigen binding or variable region of the antibody. Other examples of antibody fragments include Fab, Fab', $F(ab')_2$, and Fv fragments; diabodies; linear antibodies; single-chain antibody molecules; and multi-specific antibodies formed from antibody fragments.

The term "Fv" refers to the minimum antibody fragment containing a complete antigen-recognition and -binding site. This fragment consists of a dimer of one heavy- and one light-chain variable region domain in a tight, non-covalent association. From the folding of these two domains emanates six hypervariable loops (3 loops each from the H and L chain) that contribute amino acid residues for antigen binding and confer antigen binding specificity to the antibody. However, even a single variable domain (or half of an Fv including only three complementarity determining regions (CDRs) specific for an antigen) has the ability to recognize and bind antigen, although at a lower affinity than the entire binding site (the dimer).

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. K and λ light chains refer to the two major antibody light chain isotypes.

The term "synthetic antibody" refers to an antibody that is generated using recombinant DNA technology, such as, for example, an antibody expressed by a bacteriophage. The term also includes an antibody that has been generated by the synthesis of a DNA molecule encoding the antibody and the expression of the DNA molecule to obtain the antibody or to obtain an amino acid encoding the antibody. Synthetic DNA is obtained using available and well-known technology in the art.

The term "antigen" refers to a molecule that provokes an immune response, which may involve either antibody production, the activation of specific immunologically-competent cells, or both. Antigens include any macromolecule, including all proteins, peptides, or molecules derived from recombinant or genomic DNA. For example, DNA includes a nucleotide sequence or a partial nucleotide sequence encoding a protein or peptide that elicits an immune response, and therefore, encodes an "antigen" as the term is used herein. An antigen need not be encoded solely by a full-length nucleotide sequence of a gene. An antigen can be generated, synthesized, or derived from a biological sample including a tissue sample, a tumor sample, a cell, or a biological fluid.

The term "anti-tumor effect," as used herein, refers to a biological effect associated with a decrease in tumor volume, a decrease in the number of tumor cells, a decrease in the number of metastases, decrease in tumor cell proliferation, decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies to prevent the occurrence of tumor in the first place.

The term "auto-antigen" refers to an endogenous antigen mistakenly recognized by the immune system as foreign. Auto-antigens include cellular proteins, phosphoproteins, cellular surface proteins, cellular lipids, nucleic acids, glycoproteins, including cell surface receptors.

The term "autologous" is used to describe a material derived from a subject that is subsequently re-introduced into the same subject.

The term "allogeneic" is used to describe a graft derived from a different subject of the same species. For example, a donor subject may be related or unrelated to the recipient subject, but the donor subject has immune system markers similar to the recipient subject.

The term "xenogeneic" is used to describe a graft derived from a subject of a different species. As an example, the donor subject is from a different species than a recipient subject, and the donor subject and the recipient subject can be genetically and immunologically incompatible.

The term "cancer" is used to refer to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Throughout this specification, unless the context requires otherwise, the words "comprise," "includes," and "including" will be understood to imply the inclusion of a stated step or element or group of steps or elements but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any element listed after the phrase and can include other elements that do not interfere with or contribute to the activity or action specified in the disclosure for the listed elements. Thus, the phrase "consisting essentially of" indicates that the listed elements are required or mandatory, but those other elements are optional and may or may not be present depending upon whether they affect the listed elements' activity or action.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules, or there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein, or (b) a peptide or polypeptide having an amino acid sequence that is substantially identical to a sequence of amino acids in a reference peptide or protein.

The term "co-stimulatory ligand" refers to a molecule on an antigen-presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including at least one of proliferation, activation, differentiation, and other cellular responses. A co-stimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor, and a ligand that binds explicitly with B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal that, combined with a primary signal, such as TCR/CD3 ligation, leads to T cell proliferation and/or upregulation or down-regulation of key molecules.

The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis and wherein if the disease is not ameliorated, the subject's health continues to deteriorate. In contrast, a "disorder" in a subject is a state of health in which the animal can maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as a template for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to naturally-occurring polynucleotide or amino acid sequences that may be found in a given wild-type cell or organism. Also, a particular polynucleotide sequence isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression or overexpression" refers to the transcription and/or translation of a particular nucleotide sequence into a precursor or mature protein, for example, driven by its promoter. "Overexpression" refers to the production of a gene product in transgenic organisms or cells that exceeds levels of production in normal or non-transformed organisms or cells. As defined herein, "expression" refers to expression or overexpression.

The term "expression vector" refers to a vector including a recombinant polynucleotide including expression control (regulatory) sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes), and viruses (e.g., lentiviruses, retroviruses, adenoviruses, and adeno-associated viruses) that incorporate the recombinant polynucleotide.

Viruses can deliver nucleic acids into a cell in vitro and in vivo (in a subject). Examples of viruses useful for delivery of nucleic acids into cells include retrovirus, adenovirus, herpes simplex virus, vaccinia virus, and adeno-associated virus.

There also exist non-viral methods for delivering nucleic acids into a cell, for example, electroporation, gene gun, sonoporation, magnetofection, and the use of oligonucleotides, lipoplexes, dendrimers, and inorganic nanoparticles.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous, the two sequences are 60% homologous. By way of example, the DNA sequences ATTGCC and TATGGC share 50% homology. A comparison is made when two sequences are aligned to give maximum homology.

The term "immunoglobulin" or "lg," refers to a class of proteins that function as antibodies. The five members included in this class of proteins are IgA, IgG, IgM, IgD, and IgE. IgA is the primary antibody present in body secretions, such as saliva, tears, breast milk, gastrointestinal secretions, and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses and is important in defense against bacteria and viruses. IgD is the immunoglobulin with no known antibody function but may serve as an antigen receptor. Finally, IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule, such as a protein or nucleic acid. For example, an "isolated polynucleotide," as used herein, refers to a polynucleotide, which has been purified from the sequences which flank it in a naturally-occurring state, e.g., a DNA fragment that has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment from association with other components of the cell.

The term "substantially purified" refers to a material that is substantially free from components normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In embodiments, the cells are cultured in vitro. In embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and encode the same amino acid sequence. The phrase nucleotide sequence that encodes a protein or an RNA may also include introns to the extent that the nucleotide sequence encoding the protein may contain an intron(s) in some version.

The term "lentivirus" refers to a genus of the Retroviridae family. Lentiviruses are unique among the retroviruses in infecting non-dividing cells; they can deliver a significant amount of genetic information into the DNA of the host cell, so they are one of the most efficient methods of a gene delivery vector. Moreover, lentiviruses enable the integration of genetic information into the host chromosome, resulting in stably transduced genetic information. HIV, SIV, and FIV are all examples of lentiviruses. Vectors derived from lentiviruses offer the means to achieve significant levels of gene transfer in vivo.

The term "modulating" refers to mediating a detectable increase or decrease in the level of a response in a subject compared with the level of a response in the subject in the absence of a treatment or compound and/or compared with the level of a response in an otherwise identical but untreated subject. The term encompasses perturbing and/or affecting a native signal or response, thereby mediating a beneficial therapeutic response in a subject, preferably a human.

Nucleic acid is "operably linked" when placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence, or a ribosome binding site is operably linked to a coding sequence if it is positioned to facilitate translation.

The term "under transcriptional control" refers to a promoter being operably linked to and in the correct location and orientation in relation to a polynucleotide to control (regulate) the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area such as a solid tumor within a specific tissue or organ of the patient relative to the level of expression in a normal cell from that tissue or organ. Patients having a solid tumor or a hematological malignancy characterized by overexpression of the tumor antigen can be determined by standard assays known in the art.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme), astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma, and brain metastases).

A solid tumor antigen is an antigen expressed on a solid tumor. In embodiments, solid tumor antigens are also expressed at low levels on healthy tissue. Examples of solid tumor antigens and their related disease tumors are provided in Table 1.

TABLE 1

| Solid Tumor antigen | Disease tumor |
|---|---|
| PRLR | Breast Cancer |
| CLCA1 | colorectal Cancer |
| MUC12 | colorectal Cancer |
| GUCY2C | colorectal Cancer |
| GPR35 | colorectal Cancer |
| CR1L | Gastric Cancer |
| MUC 17 | Gastric Cancer |
| TMPRSS11B | esophageal Cancer |
| MUC21 | esophageal Cancer |
| TMPRSS11E | esophageal Cancer |
| CD207 | bladder Cancer |
| SLC30A8 | pancreatic Cancer |
| CFC1 | pancreatic Cancer |
| SLC12A3 | Cervical Cancer |
| SSTR1 | Cervical tumor |
| GPR27 | Ovary tumor |
| FZD10 | Ovary tumor |
| TSHR | Thyroid Tumor |
| SIGLEC15 | Urothelial cancer |
| SLC6A3 | Renal cancer |
| KISS1R | Renal cancer |
| QRFPR | Renal cancer: |
| GPR119 | Pancreatic cancer |
| CLDN6 | Endometrial cancer/Urothelial cancer |
| UPK2 | Urothelial cancer (including bladder cancer) |
| ADAM12 | Breast cancer, pancreatic cancer, and the like |
| SLC45A3 | Prostate cancer |
| ACPP | Prostate cancer |
| MUC21 | Esophageal cancer |
| MUC16 | Ovarian cancer |
| MS4A12 | Colorectal cancer |
| ALPP | Endometrial cancer |
| CEA | Colorectal carcinoma |
| EphA2 | Glioma |
| FAP | Mesotelioma |
| GPC3 | Lung squamous cell carcinoma |
| IL 13-Rα2 | Glioma |
| Mesothelin | Metastatic cancer |
| PSMA | Prostate cancer |
| ROR1 | Breast lung carcinoma |
| VEGFR-II | Metastatic cancer |
| GD2 | Neuroblastoma |
| FR-a | Ovarian carcinoma |
| ErbB2 | Carcinomasb |
| EpCAM | Carcinomasa |
| EGFRvlll | Glioma—Glioblastoma |
| EGFR | Glioma—NSCL cancer |
| tMUC1 | Cholangiocarcinoma, Pancreatic cancer, Breast |
| PSCA | pancreas, stomach, or prostate cancer |
| FCER2, GPR18, FCRLA, CXCR5, FCRL3, FCRL2, HTR3A, and CLEC17A | breast cancer |
| TRPMI, SLC45A2, and SLC24A5 | lymphoma |
| DPEP3 | melanoma |
| KCNK16 | ovarian, testis |
| LIM2 or KCNV2 | pancreatic |
| SLC26A4 | thyroid cancer |
| CD171 | Neuroblastoma |
| Glypican-3 | Sarcoma |
| IL-13 | Glioma |
| CD79a/b | Lymphoma |
| MAGE A4 | Lung cancer |

The term "parenteral administration" of a composition includes, e.g., subcutaneous (s.c.), intravenous (i.v.), intramuscular (i.m.), intrasternal injection, or infusion techniques.

The terms "patient," "subject," "individual," and the like are used interchangeably herein and refer to any human or animal, amenable to the methods described herein. In certain non-limiting embodiments, the patient, subject, or individual is a human or animal. For example, in embodiments, the term "subject" includes living organisms in which an immune response can be elicited (e.g., mammals). Examples of subjects include humans, and animals, such as dogs, cats, mice, rats, and transgenic species.

A subject in need of treatment or need thereof includes a subject having a disease, condition, or disorder that needs to be treated. A subject in need also includes a subject that needs treatment to prevent disease, condition, or disorder.

"Polynucleotide" or "nucleic acid" refers to mRNA, RNA, CRNA, rRNA, cDNA, or DNA. The term typically refers to a polymeric form of nucleotides of at least 10 bases in length, either ribonucleotides or deoxynucleotides, or a modified form of either type of nucleotide. The term includes all forms of nucleic acids, including single and double-stranded forms of nucleic acids.

The terms "polynucleotide variant" and "variant," and the like refer to polynucleotides displaying substantial sequence identity with a reference polynucleotide sequence or polynucleotides that hybridize with a reference sequence under stringent conditions that are defined hereinafter. These terms also encompass polynucleotides distinguished from a reference polynucleotide by adding, deleting, or substituting at least one nucleotide. Accordingly, the terms "polynucleotide variant" and "variant" include polynucleotides in which one or more nucleotides have been added, deleted, or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized).

Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions. In this regard, it is well understood in the art that some amino acids may be changed to others with broadly similar properties without changing the nature of the polypeptide activity. Polypeptide variants also encompass polypeptides in which one or more amino acids have been added, deleted, or replaced with different amino acid residues.

The term "promoter" refers to a DNA sequence recognized by the cell's synthetic machinery or introduced synthetic machinery required to initiate the specific transcription of a polynucleotide sequence. The term "expression control (regulatory) sequences" refers to DNA sequences necessary to express an operably linked coding sequence in a particular host organism. The control sequences that are suitable for prokaryotes, for example, include a promoter, optionally an operator sequence, and a ribosome binding site. In addition, eukaryotic cells utilize promoters, polyadenylation signals, and enhancers.

The term "bind," "binds," or "interacts with" refers to a molecule recognizing and adhering to a second molecule in a sample or organism but does not substantially recognize or adhere to other structurally unrelated molecules in the sample. The term "specifically binds," as used herein with respect to an antibody, refers to an antibody that recognizes a specific antigen but does not substantially recognize or bind other molecules in a sample. For example, an antibody that specifically binds an antigen from one species may also bind that antigen from one or more species. But, such cross-species reactivity does not alter an antibody's classification as specific. In another example, an antibody that specifically binds an antigen may also bind different allelic forms of the antigen. However, such cross reactivity does not alter the classification of an antibody as specific. In some instances, the terms "specific binding" or "specifically binding" can be used about the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A), in a reaction containing labeled "A" and the antibody, will reduce the amount of labeled A bound to the antibody.

By "statistically significant," it is meant that the result was unlikely to have occurred by chance. Statistical significance can be determined by any method known in art. Commonly used significance measures include the p-value, which is the frequency or probability with which the observed event would occur if the null hypothesis were true. The null hypothesis is rejected if the obtained p-value is smaller than the significance level. In simple cases, the significance level is defined at a p-value of 0.05 or less. A "decreased" or "reduced" or "lesser" amount is typically a "statistically significant" or a physiologically significant amount. It may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation" refers to a primary response induced by binding a stimulatory molecule (e.g., a TCR/CD3 complex) with its cognate ligand, thereby mediating a signal transduction event, such as signal transduction via the TCR/CD3 complex. In addition, stimulation can mediate altered expression of certain molecules, such as downregulation of TGF-β and/or reorganization of cytoskeletal structures.

The term "stimulatory molecule" refers to a molecule on a T cell that specifically binds a cognate stimulatory ligand present on an antigen presenting cell. For example, a functional signaling domain derived from a stimulatory molecule is the zeta chain associated with the T cell receptor complex. The stimulatory molecule includes a domain responsible for signal transduction.

The term "stimulatory ligand" refers to a ligand that when present on an antigen-presenting cell (e.g., an APC, a dendritic cell, a B-cell, and the like) can specifically bind with a cognate binding partner (referred to herein as a "stimulatory molecule") on a cell, for example, a T cell, thereby mediating a primary response by the T cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, disease, severity, age, weight, etc., of the subject to be treated.

The term "treat a disease" refers to reducing the frequency or severity of at least one sign or symptom of a disease or disorder experienced by a subject.

The term "transfected" or "transformed" or "transduced" refers to a process by which an exogenous nucleic acid is transferred or introduced into the host cell. A "transfected" or "transformed" or "transduced" cell has been transfected, transformed, or transduced with the exogenous nucleic acid. The cell includes the primary subject cell and its progeny.

The term "vector" refers to a polynucleotide that comprises an isolated nucleic acid and can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds that facilitate the transfer of nucleic acid into cells, such as polylysine compounds, liposomes, and the like. Examples of viral vectors include adenoviral vectors, adeno-associated virus vectors, retroviral vectors, and others. For example, lentiviruses are complex retroviruses, which, in addition to the common retroviral genes gag, pol, and env, contain other genes with regulatory or structural functions. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiply attenuating the HIV virulence genes, for example, the genes env, vif, vpr, vpu, and nef are deleted, making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges and individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, 1, 2, 2.7, 3, 4, 5, 5.3, and 6. This applies regardless of the breadth of the range.

A "chimeric antigen receptor" (CAR) molecule is a recombinant polypeptide that includes at least an extracellular domain, a transmembrane domain, and a cytoplasmic or intracellular domain. In embodiments, the domains of the CAR are on the same polypeptide chain, for example, a chimeric fusion protein. However, in embodiments, the domains are on different polypeptide chains, for example, the domains are not contiguous.

The extracellular domain of a CAR molecule includes an antigen binding domain. The antigen binding domain is for expanding and/or maintaining the modified cells, such as CAR T cells, or killing a tumor cell, such as a solid tumor. In embodiments, the antigen binding domain for expanding and/or maintaining modified cells binds an antigen, for example, a cell surface molecule or marker, on the surface of a WBC. In embodiments, the WBC is at least one of GMP (granulocyte macrophage precursor), MDP (monocyte-macrophage/dendritic cell precursors), cMoP (common monocyte precursor), basophil, eosinophil, neutrophil, SatM (Segerate-nucleus-containing atypical monocyte), macrophage, monocyte, CDP (common dendritic cell precursor), cDC (conventional DC), pDC (plasmacytoid DC), CLP (common lymphocyte precursor), B cell, ILC (Innate Lymphocyte), NK cell, megakaryocyte, myeloblast, pro-myelocyte, myelocyte, meta-myelocyte, band cells, lymphoblast, prolymphocyte, monoblast, megakaryoblast, promegakaryocyte, megakaryocyte, platelets, or MSDC (Myeloid-derived suppressor cell). In embodiments, the WBC is a granulocyte, monocyte, and or lymphocyte. In embodiments, the WBC is a lymphocyte, for example, a B cell. In embodiments, the WBC is a B cell. In embodiments, the cell surface molecule of a B cell includes CD19, CD22, CD20, BCMA, CD5, CD7, CD2, CD16, CD56, CD30, CD14, CD68, CD11b, CD18, CD169, CD1c, CD33, CD38, CD138, or CD13. In embodiments, the cell surface molecule of the B cell is CD19, CD20, CD22, or BCMA. In embodiments, the cell surface molecule of the B cell is CD19.

The cells described herein, including modified cells such as CAR and T cells, can be derived from stem cells. Stem cells may be adult stem cells, embryonic stem cells, more particularly non-human stem cells, cord blood stem cells, progenitor cells, bone marrow stem cells, induced pluripotent stem cells, totipotent stem cells, or hematopoietic stem cells. A modified cell may also be a dendritic cell, an NK-cell, a B-cell, or a T cell selected from the group consisting of inflammatory T-lymphocytes, cytotoxic T-lymphocytes, regulatory T lymphocytes, or helper T-lymphocytes. In embodiments, Modified cells may be derived from the group consisting of CD4+ T lymphocytes and CD8+ T lymphocytes. Prior to expansion and genetic modification of the cells of the invention, a source of cells may be obtained from a subject through various non-limiting methods. T cells may be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any T cell lines available and known to those skilled in the art may be used. In embodiments, modified cells may be derived from a healthy donor, from a patient diagnosed with cancer, or from a patient diagnosed with an infection. In embodiments, a modified cell is part of a mixed population of cells that present different phenotypic characteristics.

A population of cells refers to a group of two or more cells. The cells of the population could be the same, such that the population is a homogenous population of cells. The cells of the population could be different, such that the population is a mixed population or a heterogeneous population of cells. For example, a mixed population of cells could include modified cells comprising a first CAR and cells comprising a second CAR, wherein the first CAR and the second CAR bind different antigens.

The term "stem cell" refers to certain types of cells that have the capacity for self-renewal and the ability to differentiate into other kinds(s) of a cell. For example, a stem cell gives rise either to two daughter stem cells (as occurs in vitro with embryonic stem cells in culture) or to one stem cell and a cell that undergoes differentiation (as occurs, e.g., in hematopoietic stem cells, which give rise to blood cells). Different categories of stem cells may be distinguished based on their origin and/or on the extent of their capacity for differentiation into other types of cells. For example, stem cells may include embryonic stem (ES) cells (i.e., pluripotent stem cells), somatic stem cells, induced pluripotent stem cells, and other types of stem cells.

The pluripotent embryonic stem cells are found in the inner cell mass of a blastocyst and have an innate capacity for differentiation. For example, pluripotent embryonic stem cells can form any type of cell in the body. When grown in vitro for long periods, ES cells maintain pluripotency as progeny cells retain the potential for multilineage differentiation.

Somatic stem cells can include fetal stem cells (from the fetus) and adult stem cells (found in various tissues, such as bone marrow). These cells have been regarded as having a capacity for differentiation lower than that of the pluripotent ES cells—with the capacity of fetal stem cells being greater than that of adult stem cells. Somatic stem cells apparently differentiate into only a limited number of types of cells and have been described as multipotent. The "tissue-specific" stem cells normally give rise to only one cell type. For example, embryonic stem cells may be differentiated into blood stem cells (e.g., Hematopoietic stem cells (HSCs)), which may be further differentiated into various blood cells (e.g., red blood cells, platelets, white blood cells, etc.).

Induced pluripotent stem cells (i.e., iPS cells or iPSCs) may include a type of pluripotent stem cell artificially derived from a non-pluripotent cell (e.g., an adult somatic cell) by inducing an expression of specific genes. Induced pluripotent stem cells are similar to natural pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. Induced pluripotent cells can be obtained from adult stomach, liver, skin, and blood cells.

In embodiments, the antigen binding domain for killing a tumor binds an antigen on the surface of a tumor, for example, a tumor antigen or tumor marker. Tumor antigens are proteins produced by tumor cells that elicit an immune response, particularly T cell mediated immune responses. Tumor antigens are well known in the art and include, for example, tumor associated MUC1 (tMUC1), a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, surviving, telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, CD19, and mesothelin. For example, when the tumor antigen is CD19, the CAR thereof can be referred to as CD19 CAR or 19CAR, a CAR molecule that includes an antigen binding domain that binds CD19.

In embodiments, the extracellular antigen binding domain of a CAR includes at least one scFv or at least a single domain antibody. As an example, there can be two scFvs on a CAR. The scFv includes a light chain variable (VL) region and a heavy chain variable (VH) region of a target antigen-specific monoclonal antibody joined by a flexible linker. Single chain variable region fragments can be made by linking light and/or heavy chain variable regions by using a short linking peptide (Bird et al., Science 242:423-426, 1988). An example of a linking peptide is the GS linker having the amino acid sequence (GGGGS) 3 (SEQ ID NO: 24), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides and preferably comprise about 20 or fewer amino acid residues. The single chain variants can be produced either recombinantly or synthetically. For synthetic production of scFv, an automated synthesizer can be used. For recombinant production of scFv, a suitable plasmid containing a polynucleotide that encodes the scFv can be introduced into a suitable host cell, either eukaryotic, such as yeast, plant, insect, or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The cytoplasmic domain of the CAR molecules described herein includes one or more co-stimulatory domains and one or more signaling domains. The co-stimulatory and signaling domains transmit the signal and activate molecules, such as T cells, in response to antigen binding. The one or more co-stimulatory domains are derived from stimulatory molecules and/or co-stimulatory molecules, and the signaling domain is derived from a primary signaling domain, such as the CD3 zeta domain. In embodiments, the signaling domain further includes one or more functional signaling domains derived from a co-stimulatory molecule. In embodiments, the co-stimulatory molecules are cell surface molecules (other than antigens receptors or their ligands) required to activate a cellular response to an antigen.

In embodiments, the co-stimulatory domain includes the intracellular domain of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, or any combination thereof. The signaling domain includes a CD3 zeta domain derived from a T cell receptor in embodiments.

The CAR molecules described herein also include a transmembrane domain. The incorporation of a transmembrane domain in the CAR molecules stabilizes the molecule. In embodiments, the transmembrane domain of the CAR molecules is the transmembrane domain of a CD28 or 4-1BB molecule.

Between the extracellular domain and the transmembrane domain of the CAR, there may be incorporated a spacer domain. As used herein, the term "spacer domain" generally means any oligo- or polypeptide that functions to link the transmembrane domain to the extracellular domain and/or the cytoplasmic domain on the polypeptide chain. A spacer domain may include up to 300 amino acids, preferably 10 to 100 amino acids, and most preferably 25 to 50 amino acids.

The present disclosure further describes methods or compositions for treating cancer using cells derived from tumor-infiltrating lymphocytes (TILs). In embodiments, a T cell clone that expresses a TCR with a high affinity for the target antigen may be isolated. For example, TILs or peripheral blood mononuclear cells (PBMCs) can be cultured in the presence of antigen-presenting cells (APCs) pulsed with a peptide representing an epitope known to elicit a dominant T cell response when presented in the context of a defined HLA allele. High-affinity clones may be selected based on MHC-peptide tetramer staining and/or the ability to recognize and lyse target cells pulsed with low titrated concentrations of cognate peptide antigen. After the clone has been selected, the TCRα and TCRβ chains or TCRγ and TCRδ chains are identified and isolated by molecular cloning. For example, for TCRα and TCRβ chains, the TCRα and TCRβ gene sequences are then used to generate an expression construct that ideally promotes stable, high-level expression of both TCR chains in human T cells. For example, the transduction vehicle, a gammaretrovirus or lentivirus, can then be generated and tested for functionality (antigen specificity and functional avidity) and used to produce a clinical lot of the vector. An aliquot of the final product can then be used to transduce the target T cell population (generally purified from patient PBMCs), which is expanded before infusion into the patient.

Various methods may be implemented to obtain genes encoding tumor-reactive TCR. More information is provided in Kershaw et al., Clin Transl Immunology. 2014 May; 3 (5): e16. In embodiments, specific TCR can be derived from spontaneously occurring tumor-specific T cells in patients. Antigens included in this category include the melanocyte differentiation antigens MART-1 and gp100 and the MAGE antigens and NY-ESO-1, with expression in a broader range of cancers. In addition, TCRs specific for viral-associated malignancies can also be isolated, as long as viral proteins are expressed by transformed cells. Malignancies in this category include liver and cervical cancer, hepatitis and papilloma viruses, and Epstein-Barr virus-associated malignancies. In embodiments, target antigens of the TCR include CEA (e.g., for colorectal cancer), gp100, MART-1, p53 (e.g., for melanoma), MAGE-A3 (e.g., melanoma, esophageal and synovial sarcoma), and NY-ESO-1 (e.g., for melanoma and sarcoma as well as multiple myelomas).

In embodiments, preparation and transfusion of tumor infiltrating lymphocytes (TIL) may be implemented in the following manner. For example, tumor tissue from surgical or biopsy specimens can be obtained under aseptic conditions and transported to the cell culture chamber in an ice box. Necrotic tissue and adipose tissue can be removed. The tumor tissue can be cut into small pieces of about 1-3 cubic millimeters. Collagenase, hyaluronidase, and DNA enzyme can be added and digested overnight at 4° C. Filtering with a 0.2 μm filter, cells can be separated and collected by lymphocyte separation fluid under 1500 rpm for 5 min. Expanding the cells in a culture medium comprising PHA, 2-mercaptoethanol, and CD3 monoclonal antibody, and a small dose of IL-2 (10-20 IU/ml) may be added to induce activation and proliferation. The cell density may be carefully measured and maintained within the range of $0.5\text{-}2\times10^6$/ml for 7-14 days at a temperature of 37° C. with 5% $CO_2$.

TIL positive cells can kill homologous cancer cells can be screened out by co-culture. The TIL-positive cells can be amplified in a serum-free medium containing a high dose of IL-2 (5000-6000 IU/ml) until greater than $1\times10^{11}$ TILs can be obtained. To administer TILs, they are first collected in saline using continuous-flow centrifugation and then filtered through a platelet-administration set into a 200-300 mL volume containing 5% albumin and 450000 IU of IL-2. The TILs can be infused into patients through a central venous catheter over a period of 30-60 minutes. In embodiments, TILs can be infused in two to four separate bags, and the individual infusions can be separated by several hours.

The present disclosure further describes a method of enhancing T cell response caused by CAR T/TILs/TCR based therapies using delivery of the antigen corresponding to these therapies. For example, GUCY2C or, at least, the extracellular domain of GUCY2C may be delivered to patients' bodies to enhance GUCY2C CAR T cells' anti-tumor activities, an increase in T cell response. In embodiments, the increase in T cell response is based on the number of copies of CAR(s) and/or the amount of cytokine released (e.g., IL-6 and IFN-γ. In embodiments, the T cell response comprises cytokine releases, cell expansion, and/or activation levels. In embodiments, the first vector further comprises a polynucleotide encoding IL-6 or IFNγ, or a combination thereof. In embodiments, the first vector further comprises a polynucleotide encoding IL-12. In embodiments, the polynucleotide comprises a polynucleotide encoding NFAT and/or VHL. In embodiments, the population of modified cells comprises cells expressing the first binding molecule and IL-6 or IFNγ, or a combination thereof, cells expressing the second binding molecules, cells expressing the first and second molecules, and/or cells expressing the first binding molecule and IL-12. In embodiments, the population of modified cells comprises cells expressing the second binding molecule and IL-6 or IFNγ, or a combination thereof, cells expressing the second binding molecules, cells expressing the first and second molecules, and/or cells expressing the first binding molecule and IL-12. In embodiments, the population of modified cells comprises cells expressing the second binding molecule and IL-6 or IFNγ, or a combination thereof, cells expressing the second binding molecules, cells expressing the first and second molecules, and/or cells expressing the second binding molecule and IL-12. In embodiments, the population of modified cells comprises cells expressing a dominant negative form of PD-1. The antigen may be formulated as a form of a vaccine. Examples of vaccines include DCs, including the antigen, amph-ligand, and a nanoparticle RNA vaccine. More information about the vaccine examples may be found at E Snook, A. "Companion vaccines for CAR T-cell therapy: applying basic immunology to enhance therapeutic efficacy," Future Medicinal Chemistry, V. 12, No. 15, 2020, pp. 1359-62, which is incorporated by its entirety.

In embodiments, the CAR molecules' cytoplasmic domain described herein comprises a co-stimulatory domain and a CD3 zeta domain. In embodiments, the CAR molecules described herein may include a co-stimulatory domain without a corresponding component of the CD3 zeta domain. In embodiments, the CAR molecules described herein may include a CD3 zeta domain without a co-stimulatory domain.

In embodiments, the modified cell comprises a dominant negative variant of a receptor of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3

(LAG-3), T cell immunoreceptor with Ig and ITIM domains (TIGIT), leukocyte-associated immunoglobulin-like receptor 1 (LAIRI), natural killer cell receptor 2B4 (2B4), or CD 160. In embodiments, the modified cell further comprises a nucleic acid sequence encoding a suicide gene, and/or the suicide gene comprises an HSV-TK suicide gene system. In embodiments, the isolated T cell comprises a reduced amount of TCR compared to the corresponding wide-type T cell.

Dominant negative mutations have an altered gene product that antagonizes the wild-type allele. These mutations usually result in an altered molecular function (often inactive) and are characterized by a dominant or semi-dominant phenotype. In embodiments, the modified cells described herein comprise the dominant negative (DN) form of the PD-1 receptor. In embodiments, the expression of the DN PD-1 receptor in the modified cells described herein is regulated by an inducible gene expression system. In embodiments, the inducible gene expression system is a lac system, a tetracycline system, or a galactose system.

The present disclosure describes pharmaceutical compositions. The pharmaceutical compositions include one or more of the following: CAR molecules, TCR molecules, modified CAR T cells, modified cells comprising CAR or TCR, mix population of modified cells, nucleic acids, and vectors described herein. Pharmaceutical compositions are administered appropriately to the disease to be treated (or prevented). Such factors will determine the quantity and frequency of administration as the patient's condition and the type and severity of the patient's disease, although clinical trials may determine appropriate dosages.

The term "pharmaceutically acceptable" means approved by a regulatory agency of the U.S. Federal or a state government or the EMA (European Medicines Agency) or listed in the U.S. Pharmacopeia Pharmacopeia (United States Pharmacopeia-33/National Formulary-28 Reissue, published by the United States Pharmacopeia Convention, Inc., Rockville Md., publication date: April 2010) or other generally recognized pharmacopeia for use in animals, and more particularly in humans.

The term "carrier" refers to a diluent, adjuvant {e.g., Freund's adjuvant (complete and incomplete)), excipient, or vehicle with which the therapeutic is administered. Pharmaceutical carriers can be sterile liquids, such as water and oils, including petroleum, animal, vegetable, or synthetic origins, such as peanut oil, soybean oil, mineral oil, sesame oil, and the like. Water is a preferred carrier when the pharmaceutical composition is administered intravenously. Saline solutions and aqueous dextrose and glycerol can also be used as liquid carriers, particularly for injectable solutions.

The present disclosure also describes a pharmaceutical composition comprising the first and the second population of cells described herein. The pharmaceutical composition described herein, comprising a first population of cells comprising a first antigen binding molecule and a second population of cells comprising a second antigen binding domain, are suitable for cancer therapy. For example, the binding of a first antigen binding molecule with an antigen enhances the expansion of the cells suitable for cancer therapy.

The present disclosure also describes a method for enhancing cancer therapy using the cells described herein suitable for cancer therapy. The method comprises administering an effective amount of a first composition to the subject having a form of cancer expressing a tumor antigen, the first composition comprising a population of cells (e.g., T cells) comprising an antigen binding molecule (e.g., CAR) binding an antigen; and administering an effective amount of a second composition to the subject, the second composition comprising the antigen in the form of vaccines (e.g., DC-antigen and nanoparticle-mRNA). The first and second compositions can be performed simultaneously or separately, for example, sequentially. More information about the cells suitable for cancer therapy can be found at Eyileten, C., Majchrzak, K., Pilch, Z., et al. "Immune Cells in Cancer Therapy and Drug Delivery," Mediators of Inflammation, V. 2016, 2016, pp. 1-13 and Reinhard, K., Rengstl, B., Oehm, P., et al. "An RNA vaccine drives expansion and efficacy of claudin-CAR-T cells against solid tumors," Science, V. 367, No. 6476, 2020, pp. 446-53., which are incorporated herein for reference.

When "an immunologically effective amount," "an anti-tumor effective amount," "a tumor-inhibiting effective amount," or "a therapeutically effective amount" is indicated, the precise amount of the compositions of the present disclosure to be administered can be determined by a physician with consideration of individual differences in age, weight, tumor size, the extent of infection or metastasis, and condition of the patient (subject). It can be stated that a pharmaceutical composition comprising the modified cells described herein may be administered at a dosage of $10^4$ to $10^9$ cells/kg body weight, preferably $10^5$ to $10^6$ cells/kg body weight, including all integer values within those ranges. Modified cell compositions may also be administered multiple times at these dosages. The cells can be administered using infusion techniques commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly. In certain embodiments, it may be desired to administer activated T cells to a subject and then subsequently redraw the blood (or have apheresis performed), collect the activated and expanded T cells, and reinfuse the patient with these activated and expanded T cells. This process can be carried out multiple times every few weeks. In certain embodiments, T cells can be activated from 10 cc to 400 cc in blood draws. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocols may select out certain populations of T cells.

The administration of the pharmaceutical compositions described herein may be carried out in any convenient manner, including by aerosol inhalation, injection, ingestion, transfusion, implantation, or transplantation. The compositions described herein may be administered to a patient subcutaneously, intradermally, intratumorally, intranodally, intramedullary, intramuscularly, by intravenous (i. v.) injection, or intraperitoneally. In embodiments, the modified cell compositions described herein are administered to subjects by intradermal or subcutaneous injection. In embodiments, the T cell compositions of the present disclosure are administered by i.v. injection. The compositions of modified cells may be injected directly into a tumor, lymph node, or site of infection. In embodiments, cells activated and expanded using the methods described herein, or other methods known in the art where T cells are expanded to therapeutic levels, are administered to patients in conjunction with (e.g., before, simultaneously, or following) any number of relevant treatment modalities, for example as a combination therapy, including but not limited to treatment with agents for antiviral therapy, cidofovir, and interleukin-2, Cytarabine (also known as ARA-C); or natalizumab treatment for MS patients; or efalizumab treatment for psoriasis patients or other treatments for PML patients. In further embodiments, the T cells described herein can be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies, or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun 73:316-321, 1991; Bierer et al., Curr. Opin. Immun 5:763-773, 1993; Isoniemi (supra)). In embodiments, the cell compositions described herein are administered to a subject in conjunction with (e.g., before, simultaneously, or following) bone marrow transplantation, T cell ablative therapy using either chemotherapy agents such as fludarabine, external-beam radiation therapy (XRT), cyclophosphamide, or antibodies such as OKT3 or CAMPATH. In embodiments, the cell compositions described herein are administered following B-cell ablative therapy. For example, agents that react with CD20, e.g., Rituxan, may be administered to patients. In embodiments, subjects may undergo standard treatment with high-dose chemotherapy followed by peripheral blood stem cell transplantation. In certain embodiments, following the transplant, subjects receive an infusion of the expanded immune cells of the present disclosure. In embodiments, expanded cells are administered before or following surgery. The dosage of the above treatments to be administered to a subject in need will vary with the precise nature of the condition being treated and the treatment recipient. The scaling of dosages for human administration can be performed according to art-accepted practices by a physician depending on various factors. Additional information on the methods of cancer treatment using modified cells is provided in U.S. Pat. No. 8,906,682, incorporated by reference in its entirety.

In embodiments, the method may further comprise administering an additional composition comprising CAR T cells targeting an antigen of WBCs (e.g., CD19 and BCMA).

The present disclosure is related to enhancing CoupledCAR® to treat cancer patients. In embodiments, the method comprises administering a mixed cell in an immunologically effective amount comprising a first population of modified cells comprising a first binding molecule targeting a solid tumor antigen and a second population of modified cells comprising a second binding molecule targeting a WBC or a blood antigen in a pharmaceutically acceptable carrier and administering one or more nucleic acid encoding the solid tumor antigen or a variant thereof in a pharmaceutically acceptable carrier, the nucleic acid being in vitro transcribed RNA. In embodiments, the transcribed RNA is encapsulated in liposomes. In embodiments, the method comprises administering the first population of modified cells comprising a first binding molecule targeting a solid tumor antigen in a pharmaceutically acceptable carrier, administration of the second population of modified cells comprising a second binding molecule targeting a WBC or a blood antigen in a pharmaceutically acceptable carrier, and administering one or more nucleic acid encoding the solid tumor antigen or a variant thereof in a pharmaceutically acceptable carrier, the nucleic acid being in vitro transcribed RNA. In embodiments, the transcribed RNA is encapsulated in liposomes. More information on CoupledCAR® may be found at PCT Publication NOS: WO2020106843 and WO2020146743.

Lipid particles include lipid nanoparticles (LNPs) which are spherical veisicles comprising lipids. They can be used for delivery to nucleic acids to a target site. Lipids include cationic lipids, neutrol lipids, and anionic lipids. Examples of cationic lipids include DOTMA (2-di-O-octadecenyl-3-trimethylammonium propane), DOTAP (12-dioleoyloxy-3-[trimethylammonium]-propane), DOSPA (2,3-dioleyloxy-N-[2 (sperminecarboxamido)ethyl]-N,N-dimethyl-I-propanaminium trifluoroacetate), and DC-Chol (3B [N—(N',N'-dimethylaminoethane)-carbamoyl]cholesterol). Examples of neutral lipids include cholesterol, DOPC (1,2-Dioleoyl-sn-glycero-3-phosphocholine), and DOPE (12-Dioleoyl-sn-glycero-3-phosphoethanolamine).

Some lipids are amphipathic, such as phospholipids Examples of phospholipids include DSPC (distearoylphosphatidylcholine). Phospholipids have a propensity to form liposomes when hydrated in aqueous solutions. Liposomes are spherical vesicles consisting of one or more concentric lipid bilayers enclosing discrete aqueous spaces. As used herein, LNPs include liposomes. Liposomes can also be formed using cationic lipids or a combination of lipids such as cationic, neutral, anionic, and/or phospholipids.

In embodiments, the first composition may comprise a modified cell. The modified cell may comprise an antigen binding molecule, and expression and/or function of one or more proteins in the modified T cell has been increased or enhanced, and the one or more proteins comprise cytokine (s) (e.g., IL-6 or IFNγ, or a combination thereof). In embodiments, the modified T cells express and secrete the one or more proteins in response to activation of the modified T cells, hypoxia, or a combination thereof. In embodiments, IL-6 is human IL-6, and IFNγ is human IFNγ. In embodiments, the modified T cells comprise an exogenous polynucleotide encoding the one or more proteins. In embodiments, the exogenous polynucleotide is present in the modified T cell in a recombinant DNA construct, mRNA, or viral vector. In embodiments, the exogenous polynucleotide comprises a promoter comprising a binding site for a transcription modulator that modulates the expression and/or secretion of IL-6, IFNγ, or a combination thereof, in the modified cell. In embodiments, the transcription modulator comprises Hif1a, NFAT, FOXP3, or NFkB. Examples of cytokines include IL-1P, IL-2, IL-4, IL-5, IL-6, IL-7, IL-8, IL-10, IL-12, IL-13, IL-15, IL-17, IL-1Ra, IL-2R, IFN-γ, IFN-γ, MIP-In, MIP-IP, MCP-1, TNFα, GM-CSF, GCSF, CXCL9, CXCL10, CXCR factors, VEGF, RANTES, EOTAXIN, EGF, HGF, FGF-P, CD40, CD40L, and ferritin. In embodiments, a cytokine may be administered to the subject directly. For example, method of enhancing anti-tumor activities of modified cells, the method comprising: administering an effective amount of the modified cells to a subject having a solid tumor; and administering an effective amount of an agent to the subject, the agent comprising Granulocyte Colony Stimulating Factor (G-CSF); wherein the modified cells inhibit the growth of the solid tumor in the subject, and wherein the anti-tumor activities in the subject are greater than those in a subject that is administered with an effective amount of modified cells but without the agent. In embodiments, administering an effective amount of the agent to the subject comprises administering an effective amount of G-CSF to the subject using a long-acting G-CSF at a dose of about 1-60 mg per subject or 10-1000 μg/kg of body weight. In embodiments, administering an effective amount of the agent to the subject comprises administering an effective amount of G-CSF to the subject using a long-acting G-CSF at a dose of about 6 mg per subject or 100 μg/kg of body weight. In embodiments, administering an effective amount of the agent to the subject comprises administering an effective amount of G-CSF to the subject in less than 1, 2, 3, 4, or 5 days after the subject has been administered the effective amount of the modified cells. In embodiments, administering an effective amount of agent to the subject comprises administering an effective amount of G-CSF to the subject in less than 14 days after the subject has been administered the effective amount of modified cells.

Embodiments relate to using or using polynucleotide encoding the antigen binding molecule and/or therapeutic agent(s) to enhance the expansion of the modified cells or enhance the T cell response in a subject. The method or use includes: providing a viral particle (e.g., AAV, lentivirus or their variants) comprising a vector genome, the vector genome comprising the polynucleotide, wherein the polynucleotide is operably linked to an expression control element conferring transcription of the polynucleotide; and administering an amount of the viral particle to the subject such that the polynucleotide is expressed in the subject. In embodiments, the AAV preparation may include AAV vector particles, empty capsids and host cell impurities, thereby providing an AAV product substantially free of AAV empty capsids. More information on the administration and preparation of the viral particle may be found at the U.S. Pat. No. 9,840,719 and Milani M, Annoni A, Moalli F, et al. Phagocytosis-shielded lentiviral vectors improve liver gene therapy in nonhuman primates. Sci Transl Med. 2019; 11 (493): eaav7325. doi: 10.1126/scitranslmed.aav7325, which are incorporated herein by reference.

In embodiments, the polynucleotide may integrate into the genome of the modified cell, and the progeny of the modified cell will also express the polynucleotide, resulting in a stably transfected modified cell. In embodiments, the modified cell expresses the polynucleotide encoding the CAR. However, the polynucleotide does not integrate into the genome of the modified cell such that the modified cell expresses the transiently transfected polynucleotide for a finite period (e.g., several days), after which the polynucleotide is lost through cell division or other factors. For example, the polynucleotide is present in the modified cell in a recombinant DNA construct, in an mRNA, or a viral vector, and/or the polynucleotide is an mRNA, which is not integrated into the genome of the modified cell.

The present disclosure describes enhancing a combination of the vaccine and CAR T therapy. While the combination therapy showed in vitro expansion, vaccines have been designed to target APCs (e.g., DCs). Examples of the vaccines include peptide-DC vaccination for pMHC-directed CAR-T cells, surrogate antigen delivery to APCs in vivo, and native antigen delivery to APCs in vivo. It has been known that immune checkpoint molecule (e.g., PD-1) on DC plays a critical role in limiting T cell responses. For example, while DCs are the major antigen-presenting cells for cross-presenting tumor antigens to T cells, subsequent PD-L1 upregulation protects them from killing by cytotoxic T lymphocytes, which dampens the antitumor responses. In addition, blocking PD-L1 in established tumors promotes the re-activation of tumor-infiltrating T cells for tumor control.

In embodiments, the method of stimulating an immune response to tumor cells expressing an antigen comprises administering to CAR T cells targeting the antigen to a subject; and administering one or more nucleic acids encoding the antigen or a variant thereof, wherein the nucleic acid is in vitro transcribed RNA is encapsulated in liposomes, in a pharmaceutically acceptable carrier, diluent, buffer, preservative, or excipient, wherein the CAR T cells comprise a modified immune checkpoint molecule (e.g., PD-1). An immune checkpoint molecule refers to a molecule associated with the T-cells and regulates T-cell response. In embodiments, the immune checkpoint molecule is selected from the group consisting of PD-1, cytotoxic T lymphocyte antigen-4 (CTLA-4), B- and T-lymphocyte attenuator (BTLA), T-cell immunoglobulin mucin-3 (TIM-3), lymphocyte-activation protein 3 (LAG-3), T-cell immunoreceptor with Ig and ITIM domains (TIGIT), leukocyte-associated immunoglobulin-like receptor 1 (LAIRI), natural killer cell receptor 2B4 (2B4), and CD 160.

In embodiments, a modified PD-1 is a dominant negative form of PD-1. In embodiments, the modified PD-1 comprises an extracellular domain of PD-1 and a cytoplasmic domain of the PD-1 polypeptide is truncated, or the modified cell has a partial or complete deletion of the PD-1 gene and a reduced amount of PD-1 as compared to the corresponding wild-type cell, or a non-functional PD-1 gene. In embodiments, the modified PD-1 comprises a mutation of Tyrosine residue 223 and/or a mutation of Tyrosine residue 248.

In embodiments, a modified CTLA-4 is a truncated CTLA-4 that interferes with a pathway between CTLA-4 of a T-cell and CTLA4 ligand of a target cell. For example, the truncated CTLA4 comprises a CTLA4 extracellular domain or a CTLA4 transmembrane domain, or a combination thereof. Examples of the truncated CTLA4 can be found at PCT Publication No: WO2020/086989, which is incorporated in its entirety.

Embodiments relate to a lipid particle comprising: a cationic and/or pH responsive lipid, a water-soluble therapeutically effective compound, and polynucleotides encoding an antigen and one or more immune cell activators. In embodiments, the one or more immune cell activators are one or more T cell activators such as ligands of CD80, CD86 protein, 41BBL protein, and other costimulatory structural receptors; and CD28 antibody, 41BB antibody, and other costimulatory structural receptor activating antibodies. Embodiments use nanoliposome particle carrier mRNA vaccine (LNP mRNA vaccine) combined with CoupledCAR-T to conduct cell in vitro co-cultivation experiments, flow cytometric detection of cytokine expression, and CAR-T expression. Expected experimental results: Enhance the expansion of CAR-T, reduce exhaustion, and improve the ability of CoupledCAR-T to kill tumor cells. Embodiments use LNP mRNA vaccine to present and express different signals (including ligands, antibodies, targets, factors, etc.), such as using LNP mRNA vaccine to present second signals (such as CD80, CD86 protein, 41BBL protein, and other co-stimulatory structure receptors) Ligand, and CD28 antibody, 41BB antibody, and other co-stimulatory structural receptor activation antibodies), presenting the third signal (such as cytokines IL2/7/15/21/23/12/18, CCL5, CCL22, etc.) Etc. conducted cell co-cultivation experiments in vitro, flow cytometric detection of cytokine expression, and CAR-T expression. Expected experimental results: Enhance the expansion of CAR-T, reduce exhaustion, and improve the ability of CoupledCAR-T to kill tumor cells. The use of nanoliposome particle carrier mRNA vaccine (LNP mRNA vaccine) in combination with CoupledCAR-T, and we are the delivery of the second signal (such as CD80, CD86 protein, 41BBL protein and other co-stimulatory structure receptor ligands, and CD28 Antibodies, 41BB antibodies and other co-stimulatory structural receptor activating antibodies) and third signals (such as cytokines IL2/7/15/21/23/

12/18, CCL5, CCL22, etc.) to achieve CAR-T cells in A large amount of expansion in the microenvironment of solid tumors, and the activation does not cause exhaustion. It can better perform the functions of T cells. More information about LNP and its uses in cell therapies can be found at PCT Publication NOS: WO2020206231, WO2005120469, WO2021021634, WO2019014623, and WO2016155809 and Reinhard et al., A nanoparticle RNA vaccine strategy targets chimeric antigen receptor (CAR)-T cells to solid tumors in difficult-to-treat mouse models, SCIENCE 24 Jan. 2020:446-453, which are incorporated herein by their entirety. Parameters of LNP examples are provided in Table 2.

TABLE 2

| Particles | AA Sequences | mRNA Sequences | Electric Charge Ratio | Size |
|---|---|---|---|---|
| GCC-LNP | SEQ ID NO: 1 | SEQ ID NO: 2 | 5:1 | 100 nm |
| GFP-LNP | SEQ ID NO: 3 | SEQ ID NO: 4 | 6:1 | 100 nm |

Figure 8:
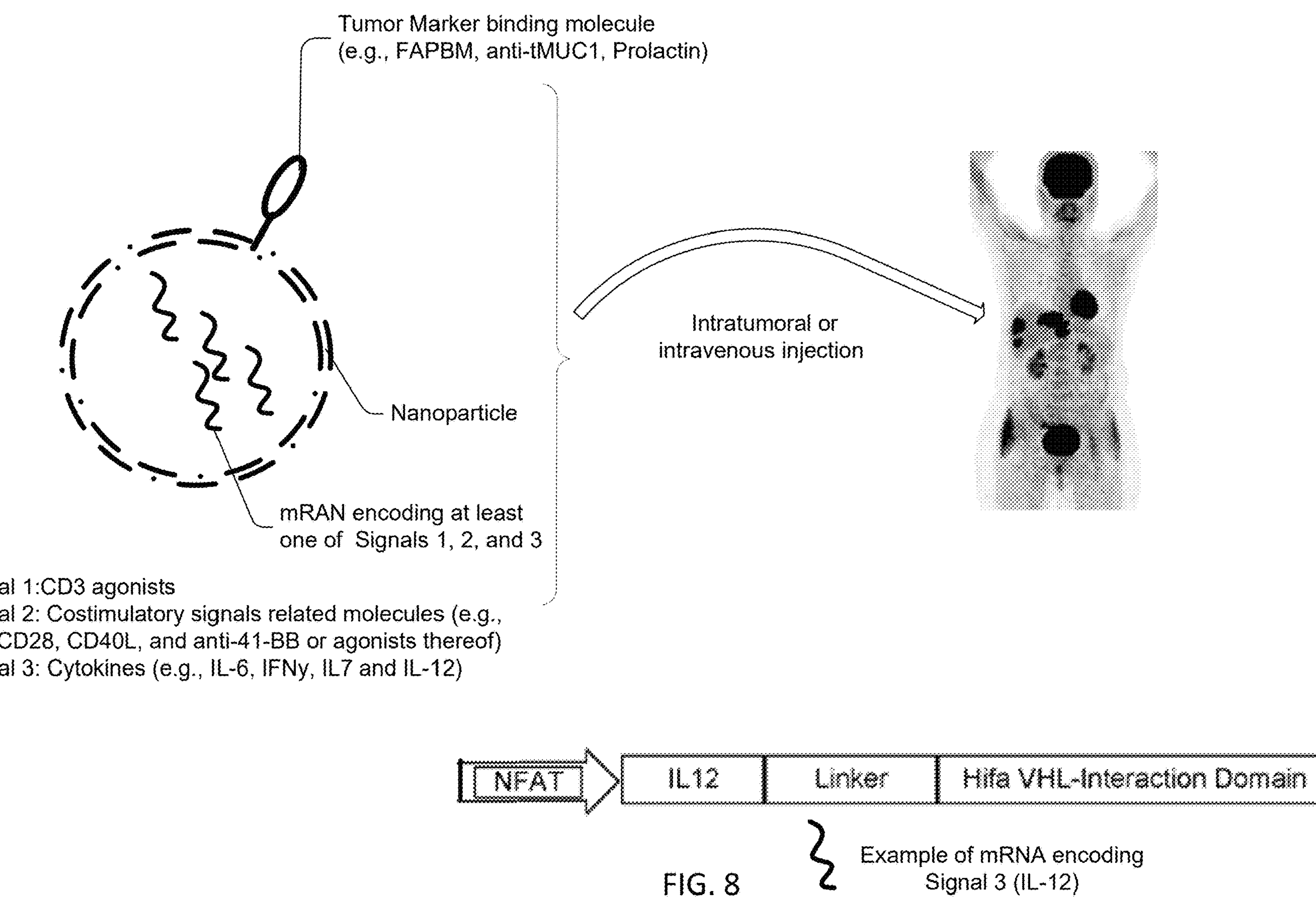
FIG. 8 shows embodiments implementing nanoparticles directed to solid tumors to treat cancer patients.
Figure 9:
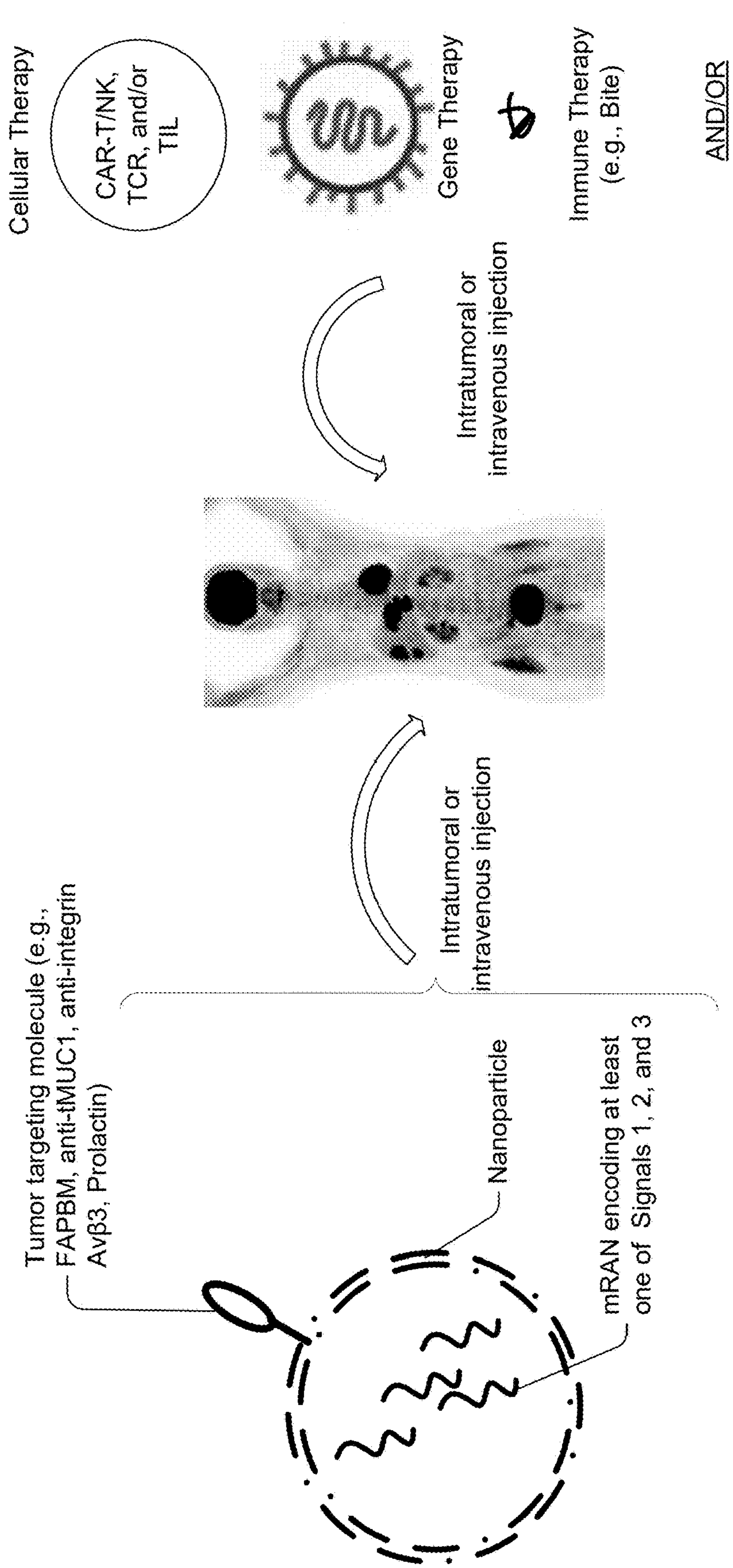
FIG. 9 shows embodiments implementing nanoparticles directed to solid tumors to treat cancer patients.
Figure 10:
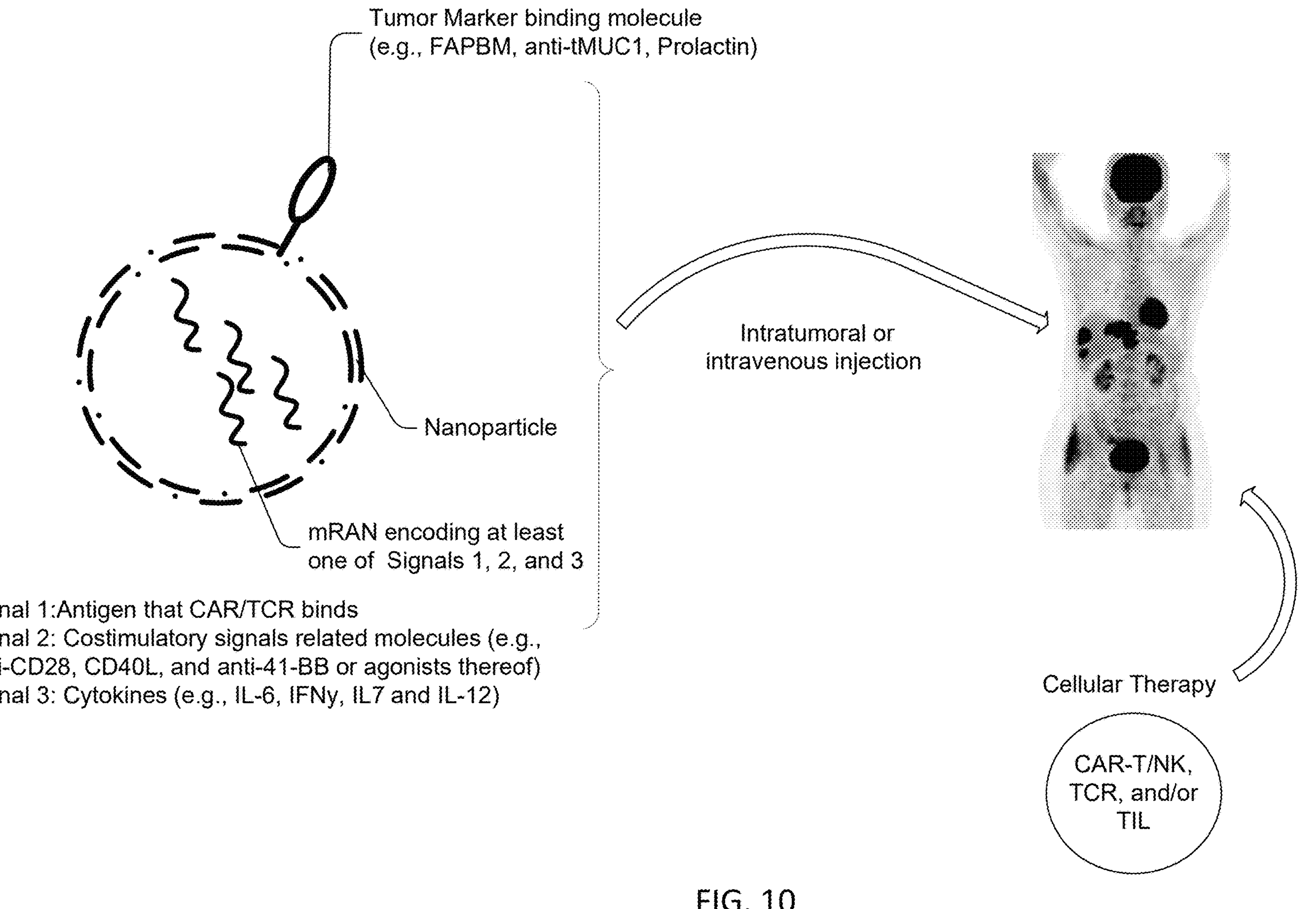
FIG. 10 shows embodiments implementing nanoparticles directed to solid tumors to treat cancer patients.
Figure 11:
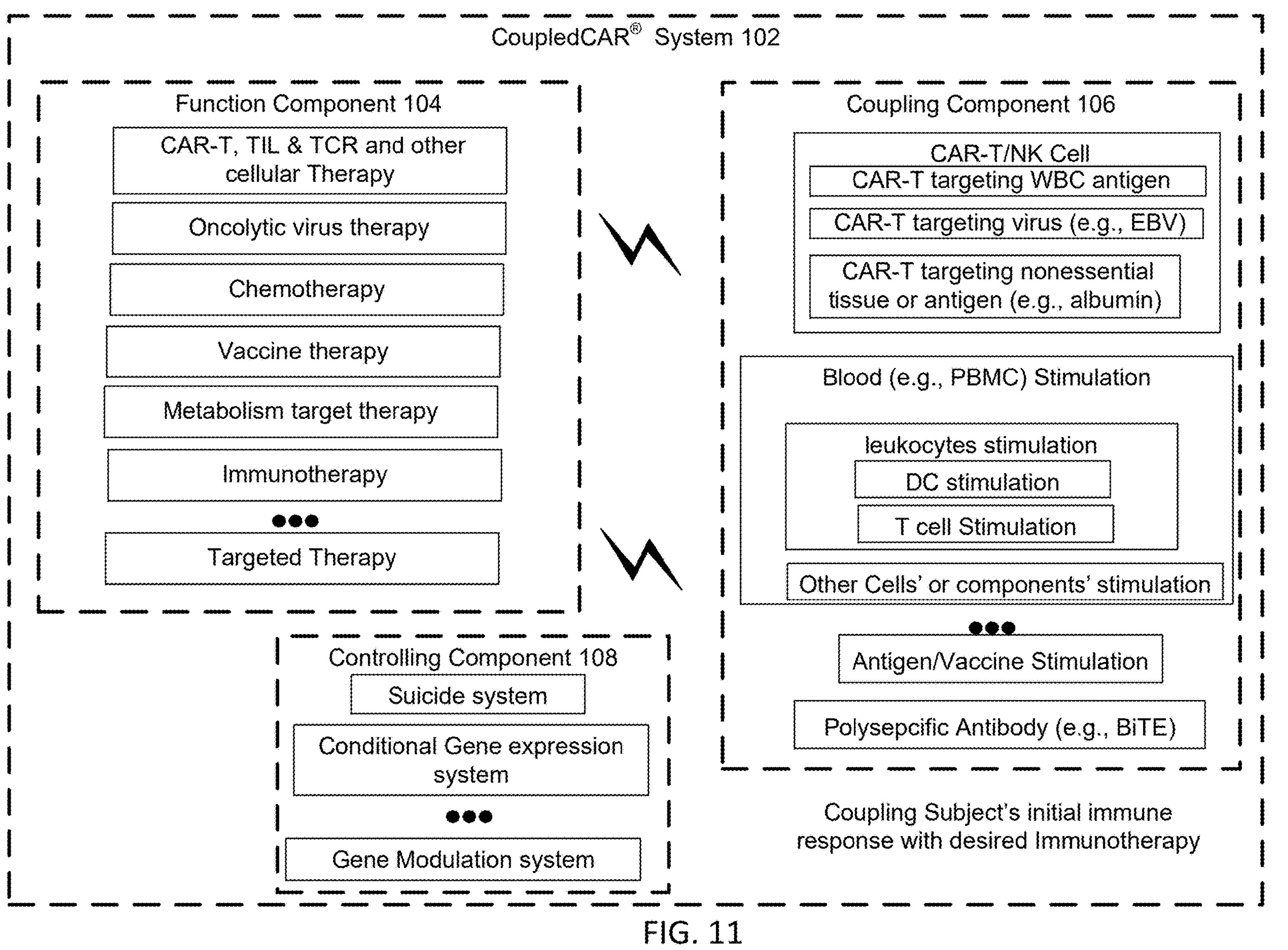
FIG. 11 shows a schematic diagram of a CoupledCAR® system.
Figure 12:
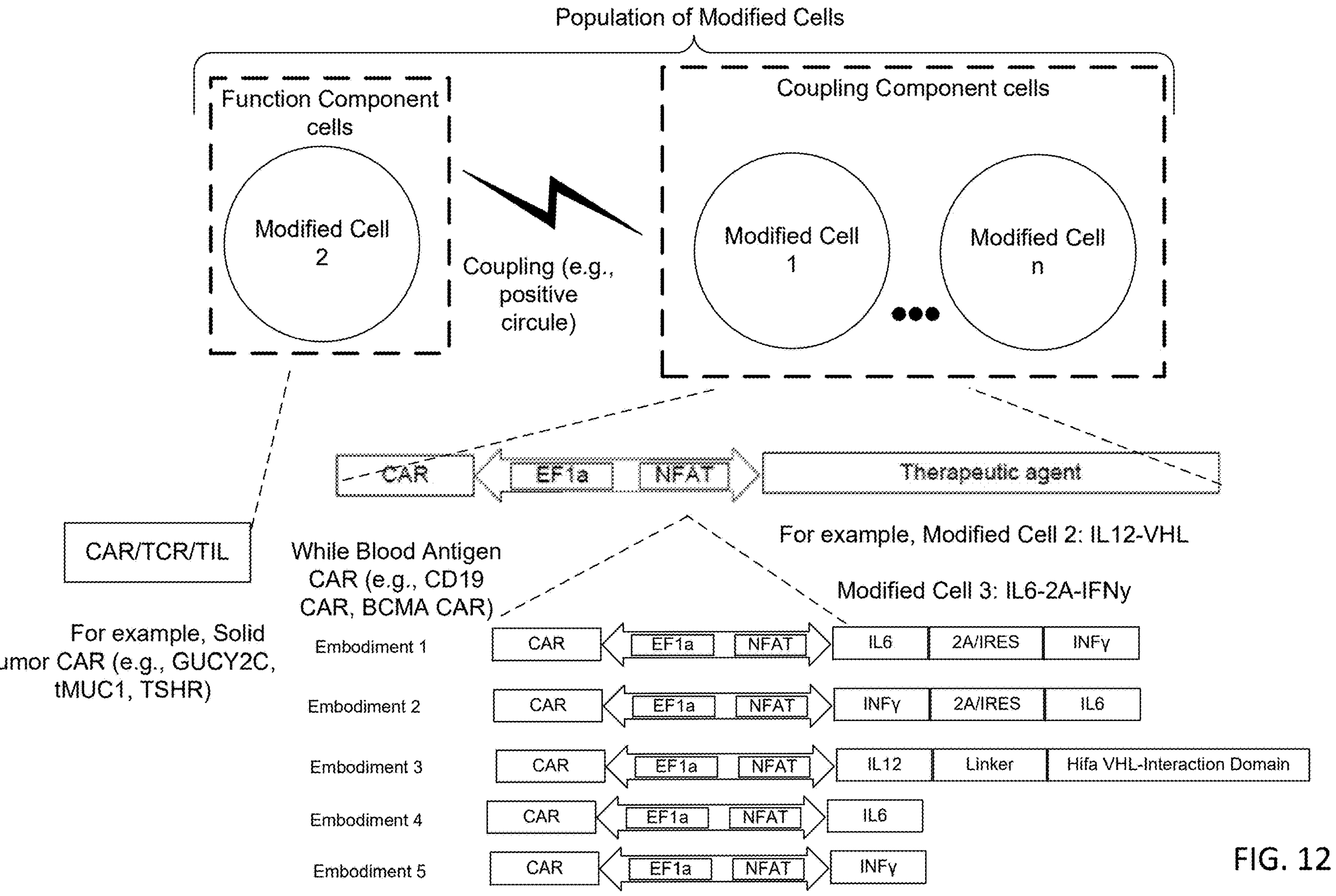
FIG. 12 shows an exemplary embodiment of the CoupledCAR® system.
Figure 13:
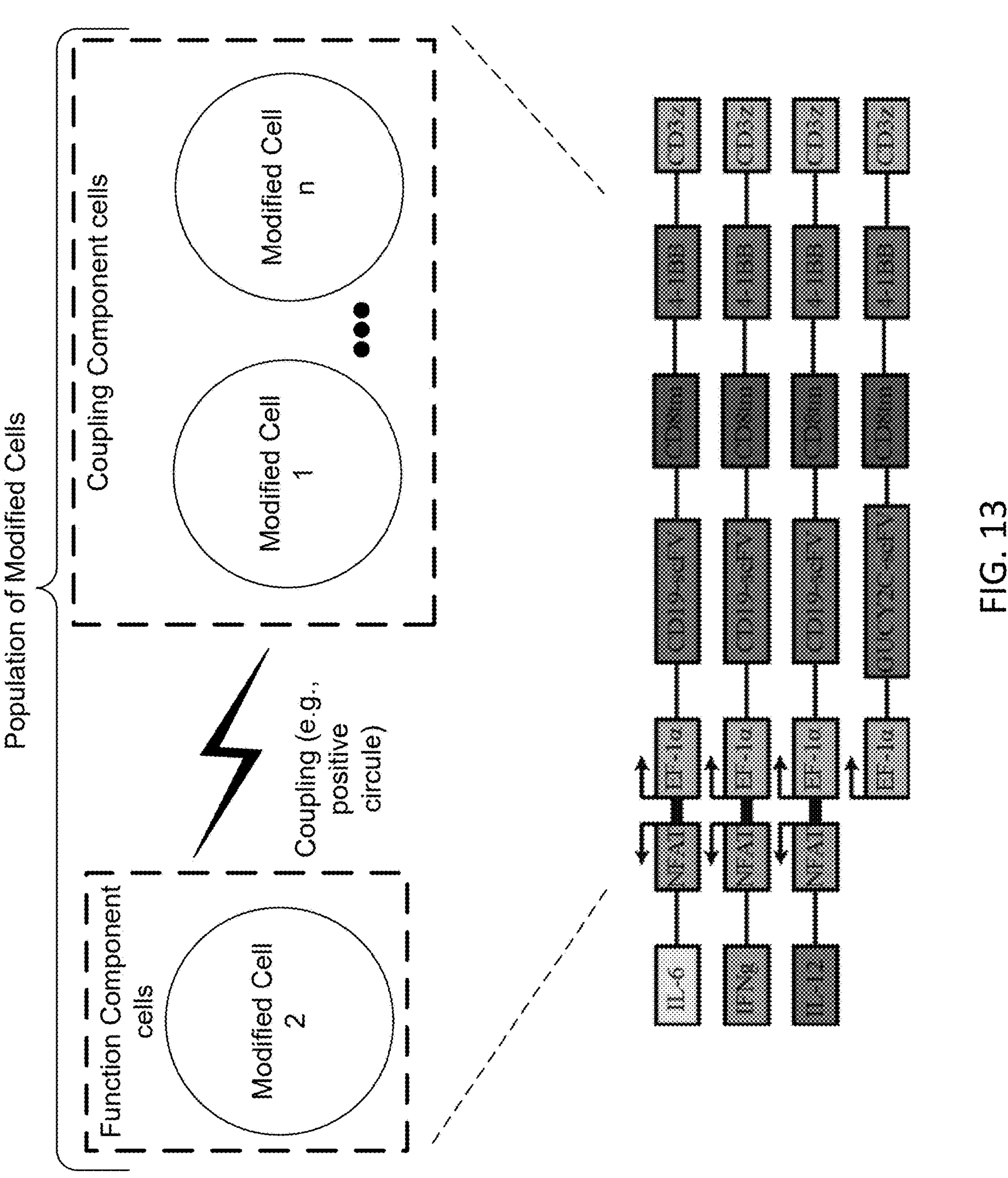
FIG. 13 shows another exemplary embodiment of the CoupledCAR® system.
Figure 14:
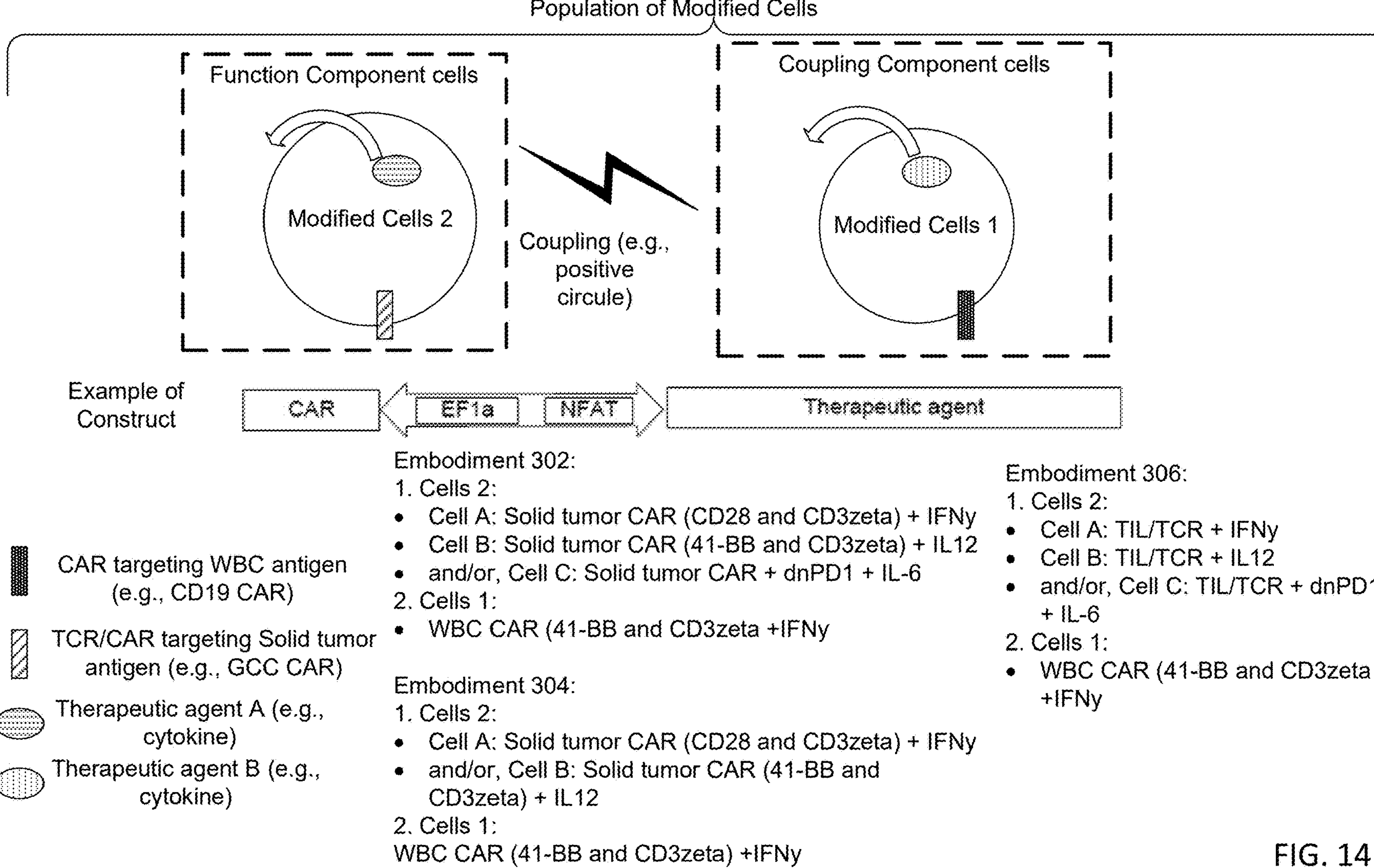
FIG. 14 shows yet another exemplary embodiment of the CoupledCAR® system.
Figure 15:
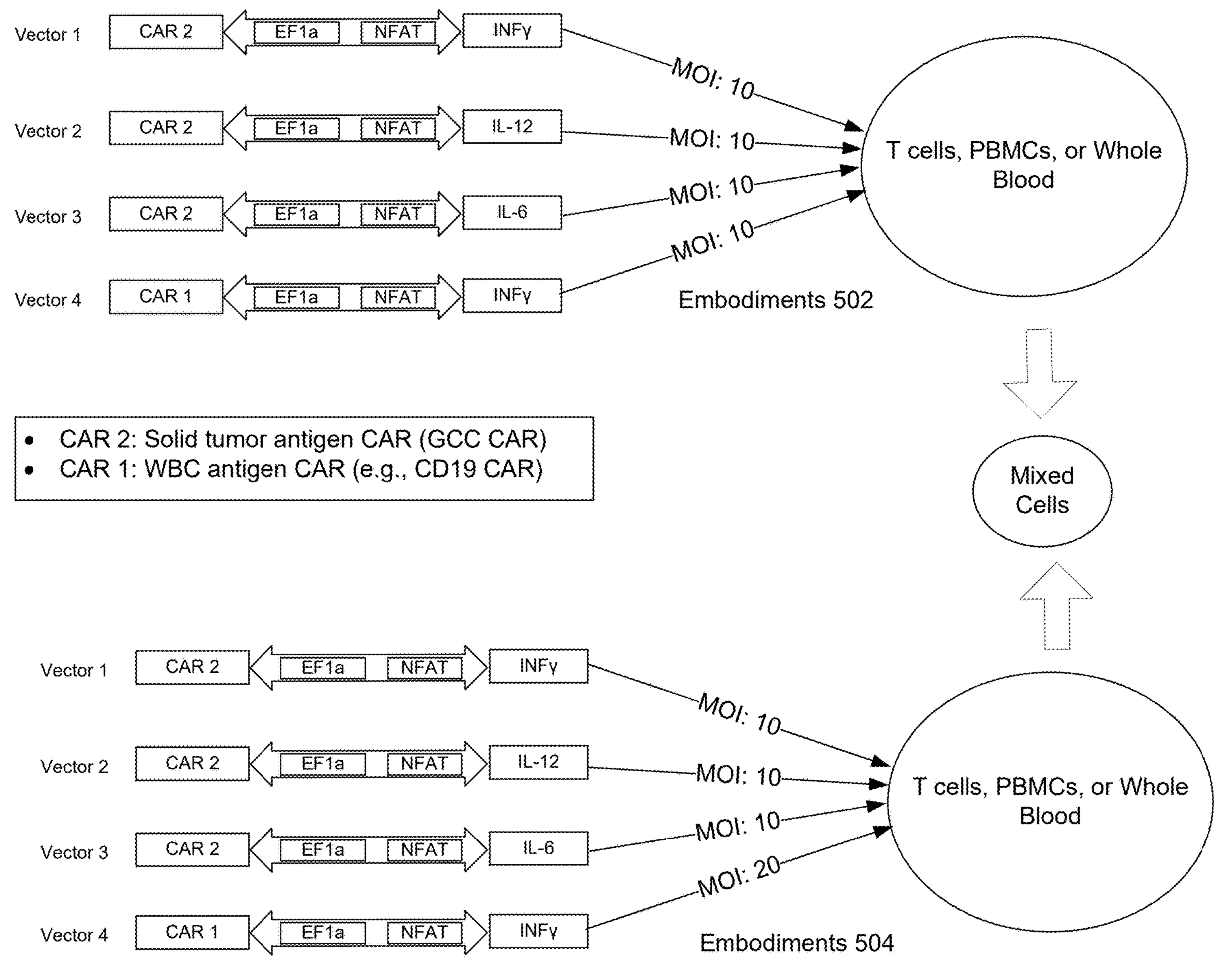
FIG. 15 shows a schematic diagram of manufactured of mixed CART cells overcoming tumor heterogeneity.
Figure 16:
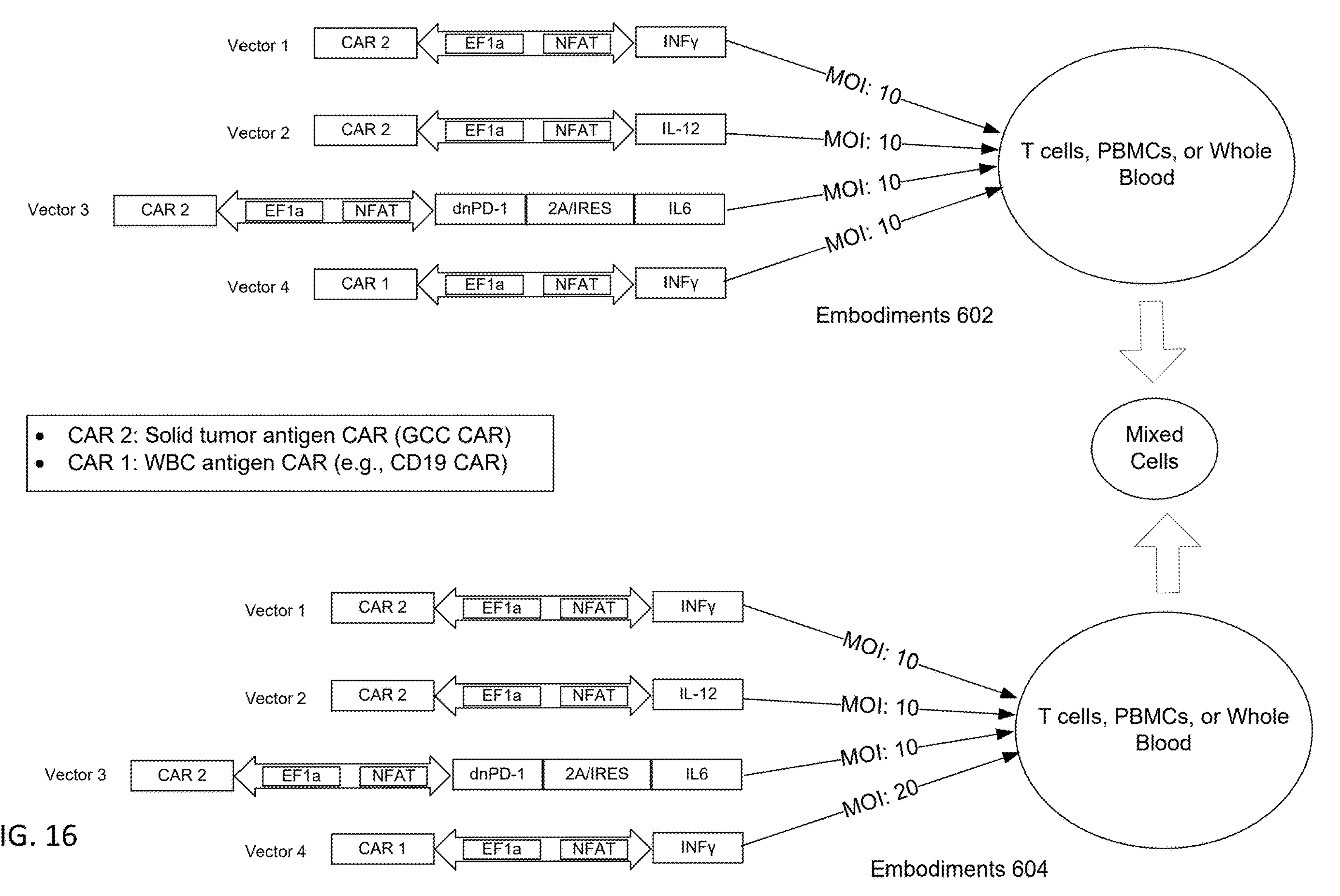
FIG. 16 shows another schematic diagram of manufactured mixed CART cells overcoming tumor heterogeneity.
Figure 17:
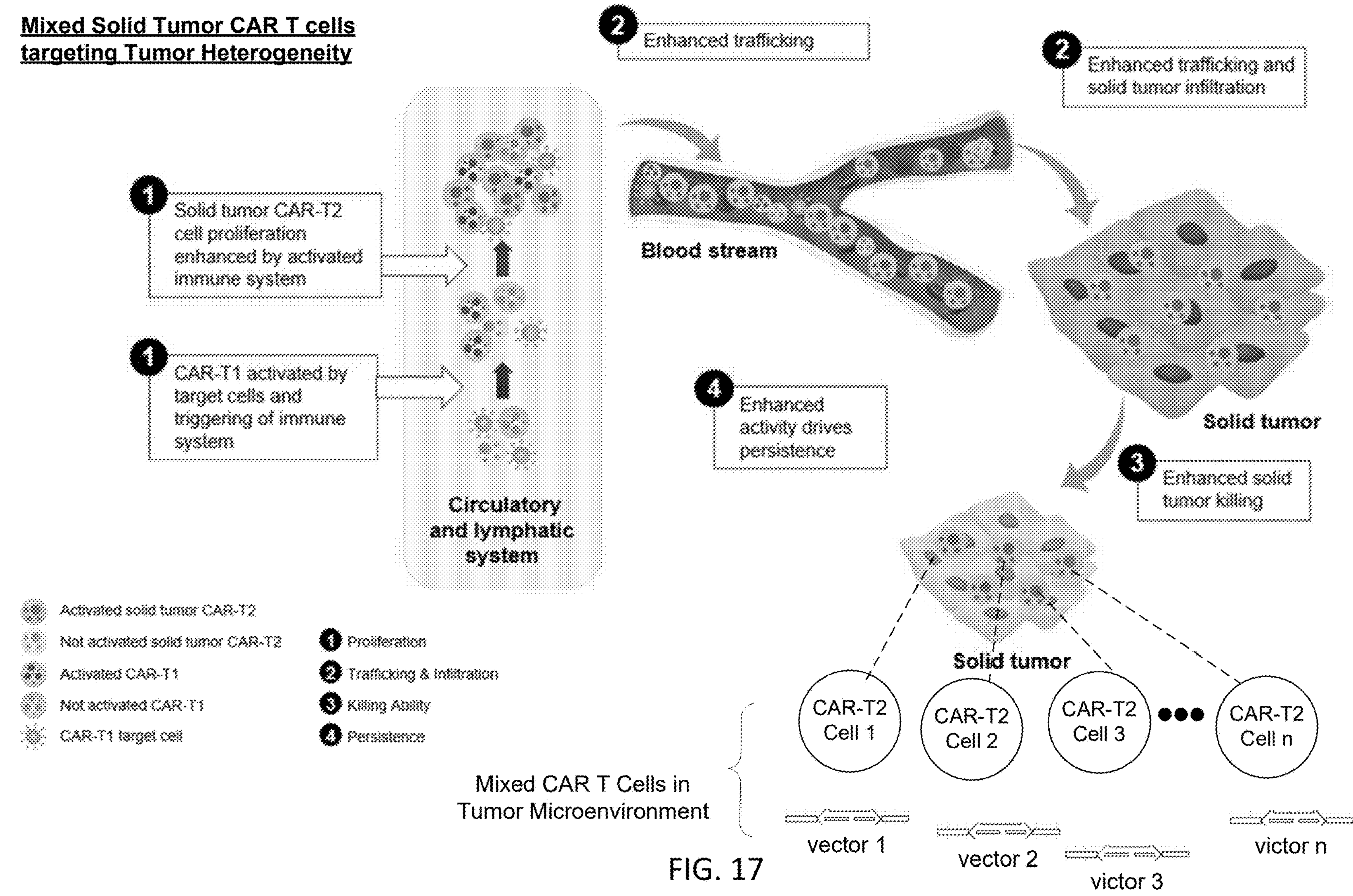
FIG. 17 shows a schematic diagram of overcoming tumor heterogeneity using mixed solid tumor CART cells, and CAR may be replaced by TIL/TCR technology.

FIGS. 8 and 9 show embodiments implementing nanoparticles directed to solid tumors to treat cancer patients. For example, FAP is highly expressed in various tumor environments and has been widely used in tumor imaging and immunotherapy. Thus, FAPBM may be coupled to the surface of a nanoparticle to direct the nanoparticle to the tumor environment. In addition, as shown in FIG. 8, the contained RNA may include regulatory elements (e.g., hypoxic elements and/or NFAT) to improve safety. Examples of therapies and related sequences thereof may be found at Applicants' PCT Patent Application No: PCT/US21/31258 and PCT/US2021/028429, which are incorporated herein by their entirety.

The present disclosure describes a method of enhancing Lymphocyte or T cell response (e.g., expansion of lymphocytes) and/or overcoming tumor heterogeneity, the method comprising: obtaining lipid particles comprising a polynucleotide encoding an antigen and a polynucleotide encoding IL-12; contacting a population of antigen-presenting cells (APCs) and a population of lymphocytes with the lipid particles, the population of lymphocytes comprising an antigen binding molecule binding the antigen; and allowing Lymphocyte or T cell response of the population of lymphocytes. In embodiments, the Lymphocyte or T cell response comprises expansion of lymphocytes, and a level of the expansion of the population of lymphocytes is greater than a level of expansion of a population of lymphocytes contacted with lipid particles comprising the polynucleotide encoding the antigen but without the polynucleotide encoding IL-12.

The present disclosure describes a method of enhancing the expansion of lymphocytes and/or overcoming tumor heterogeneity, the method comprising: obtaining lipid particles comprising a polynucleotide encoding the amino acid of SEQ ID NO: 1; contacting a population of antigen-presenting cells (APCs) and a population of lymphocytes with the lipid particles, the population of lymphocytes comprising a first population of lymphocytes comprising a chimeric antigen receptor (CAR) comprising the amino acid of SEQ ID NO: 5 or 6 and a second population of lymphocytes comprising a T cell Receptor (TCR), the second population of lymphocytes not comprising the CAR; and allowing expansion of the second populations of lymphocytes. In embodiments, the first population of lymphocytes further comprise a polynucleotide encoding IL-12, and a level of the expansion of the population of lymphocytes is greater than a level of expansion of a population of lymphocytes comprising the polynucleotide encoding the CAR without the polynucleotide encoding IL-12. Here, tumor heterogeneity refers to molecular variations between tumor cells. Examples of these cells comprise mixed tumor cells expressing different or different levels of tumor antigens or epitopes, mixed tumor cells expressing different or different levels of checkpoint inhibitors, and mixed cells comprising tumor cells and lymphocytes (M2 macrophage) that are associated with the tumor cells and/or promote, for example, tumor angiogenesis, metastasis, and immunosuppression. In embodiments, delivery of antigens to DCs enhances expansion of not only the corresponding CAR T cells that bind the antigens but also T cells that don't comprise the CAR (bystander T cells), which is surprising discovery. T cell response of these bystander T cells may help CAR T cells to overcome the tumor heterogeneity. In embodiments, cell proliferation or expansion refers to the process that results in an increase in the total number of cells, which can be measured by various methods, such as by metabolic activity assays, cell proliferation marker assays, ATP concentration assays, and DNA synthesis assays. Cell proliferation can also be measure using the Invitrogen™ CellTrace™ Violet Cell Proliferation Kit which labels cells to trace multiple generations using dye dilution by flow cytometry. In embodiments, the T cell expansion can be measured based on an increase in copy number of CAR molecules in genomic DNA of the T cells. In embodiments, the T cell expansion can be measured based on flow cytometry analysis on molecules expressed on the T cells.

In embodiments, the lymphocytes comprise T cells or NK Cells, or a combination thereof. In embodiments, the APCs comprise dendritic cells (DCs).

In embodiments, the antigen binding molecule comprises a chimeric antigen receptor (CAR). In embodiments, the CAR comprises an extracellular domain, a transmembrane domain, and an intracellular domain, and the extracellular domain binds a tumor antigen. In embodiments, the intracellular domain comprises a CD3 zeta signaling domain. In embodiments, the intracellular domain comprising a co-stimulatory domain that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, or a combination thereof.

In embodiments, the lipid particles are lipid nanoparticles (LNPs), and the antigen comprises the SEQ ID NO: 1. In embodiments, the CAR comprises the SEQ ID NO: 5.

In embodiments, the contacting the population of APCs and the population of lymphocytes with the lipid particles comprises contacting the population of APCs and the population of lymphocytes with the lipid particles to allow the population of APCs to express the antigen and express as well as secret the IL-12.

In embodiments, the binding molecule comprises a T Cell Receptor (TCR). In embodiments, the binding molecule comprises a modified TCR. In embodiments, the TCR is derived from spontaneously occurring tumor-specific T cells in patients. In embodiments, the TCR binds a tumor antigen. In embodiments, the tumor antigen comprises CEA, gp100, MART-1, p53, MAGE-A3, or NY-ESO-1. In embodiments, the TCR comprises TCRγ and TCRδ chains, TCRα and TCRβ chains, or a combination thereof.

In embodiments, the lipid particles comprise a first lipid particle comprising the polynucleotide encoding the antigen, a second lipid particle comprising the polynucleotide encoding IL-12, and a third lipid particle comprising a polynucleotide encoding a costimulatory signal related molecule. In embodiments, the costimulatory signal-related molecule comprises anti-CD28, CD40L, and anti-41-BB or agonists.

In embodiments, the modified cell comprises a dominant negative form of an immune checkpoint molecule. In embodiments, the immune checkpoint molecule comprises at least one of PD-1, cytotoxic T lymphocyte antigen-4 (CTLA-4), B- and T-lymphocyte attenuator (BTLA), T-cell immunoglobulin mucin-3 (TIM-3), lymphocyte-activation protein 3 (LAG-3), T-cell immunoreceptor with Ig and ITIM domains (TIGIT), leukocyte-associated immunoglobulin-like receptor 1 (LAIRI), natural killer cell receptor 2B4 (2B4), and CD 160.

Lymphocyte or T cell response in a subject refers to cell-mediated immunity associated with a helper, killer, regulatory, and other types of T cells. For example, T cell response may include activities such as assisting other WBCs in immunologic processes and identifying and destroying virus-infected cells and tumor cells. T cell response in the subject can be measured via various indicators such as the number of virus-infected cells and/or tumor cells that T cells kill, the amount of cytokines (e.g., IL-6 and IFN-γ) that T cells release in vivo and/or in co-culturing with virus-infected cells and/or tumor cells, indicates a level of proliferation of T cells in the subject, a phenotype change of T cells, for example, changes to memory T cells, and level longevity or lifetime of T cells in the subject.

In embodiments, the method of enhancing the T cell response described herein can effectively treat a subject in need, such as a subject diagnosed with a tumor. The term tumor refers to a mass, a collection of fluid, such as blood, or a solid mass. A tumor can be malignant (cancerous) or benign. Examples of blood cancers include chronic lymphocytic leukemia, acute myeloid leukemia, acute lymphoblastic leukemia, and multiple myeloma.

Solid tumors usually do not contain cysts or liquid areas. The major types of malignant solid tumors include sarcomas and carcinomas. Sarcomas are tumors that develop in soft tissue cells called mesenchymal cells, which can be found in blood vessels, bone, fat tissues, ligament lymph vessels, nerves, cartilage, muscle, ligaments, or tendon, while carcinomas are tumors that form in epithelial cells, which are found in the skin and mucous membranes. The most common types of sarcomas include undifferentiated pleomorphic sarcoma, which involves soft tissue and bone cells; leiomyosarcoma, which involves smooth muscle cells that line blood vessels, gastrointestinal tract, and uterus; osteosarcoma, which involves bone cells, and liposarcoma which involves fat cells. Examples of sarcomas include Ewing sarcoma, Rhabdomyosarcoma, chondosarcoma, mesothelioma, fibrosarcoma, fibrosarcoma, and glioma.

The five most common carcinomas include adrenocarcinoma, which involves organs that produce fluids or mucous, such as the breasts and prostate; basal cell carcinoma, which involves cells of the outer-most layer of the skin, for example, skin cancer; squamous cell carcinoma, which involves the basal cells of the skin; and transitional cell carcinoma which affects transitional cells in the urinary tract which includes the bladder, kidneys, and ureter. Examples of carcinomas include cancers of the thyroid, breast, prostate, lung, intestine, skin, pancreas, liver, kidneys, bladder, and cholangiocarcinoma.

The present disclosure further relates to a combination of mRNA vaccine techniques and CoupledCAR® to expanding lymphocytes in a subject having a form of cancer. More information of CoupledCAR® can be found at PCT Publication NOs: WO2020106843 and WO2020146743 and US Patent Publication NOs: US20210100841 and US20210137983, which are incorporated by reference in their entirety. For example, the present disclosure describes a method of enhancing expansion and/or activation of the response of lymphocytes, such as T cells, the method comprising: obtaining lipid particles comprising a polynucleotide encoding an antigen; contacting a population of APCs and a population of lymphocytes with the lipid particles, the population of lymphocytes comprising a first population of lymphocytes comprising a CAR binding a blood cell antigen and a second population of lymphocytes comprising an antigen binding molecule binding a solid tumor antigen; allowing expansion of the first and second population of lymphocytes, wherein a level of the expansion of the first and second population of lymphocytes is greater than a level of expansion of a respective first and second population of lymphocytes that are contacted with the population of APCs but without the lipid particles. In embodiments, the first population of lymphocytes and/or the second population of lymphocytes can be replaced with a polyspecific binding molecule, for example, CD3-CD19 and CD3-GCC. More information about the polyspecific binding molecule may be found at PCT Patent Publication NO: WO2021216731, which is incorporated by reference in its entirety.

In embodiments, the APCs comprise DCs and B cells. In embodiments, the solid tumor antigen comprises MUC1 (tMUC1), PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, CLDN 18.2, KISS1R, QRFPR, GPR119, CLDN6, UPK2, ADAM12, SLC45A3, ACPP, MUC21, MUC16, MS4A12, ALPP, CEA, EphA2, FAP, GPC3, IL13-Rα2, Mesothelin, PSMA, ROR1, VEGFR-II, GD2, FR-α, ErbB2, EpCAM, EGFRvIII, MAGE A4, EGFR, or a combination thereof. In embodiments, the lymphocytes comprise NK cells and/or T cells. In embodiments, the antigen binding molecule comprises a CAR or TCR.

The present disclosure is further described by referencing the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples, but rather, should be construed to encompass any and all variations which become evident as a result of the teaching provided herein.

Exemplary Embodiments

The following are exemplary embodiments:

1. A method of enhancing T cell response in a subject or treating a subject having cancer, the method comprising: administering an effective amount of a composition comprising modified cells to the subject having a form of cancer associated with or expressing an antigen (e.g., a solid tumor antigen); and administering an effective amount of: a composition comprising one or more nucleic acids encoding the antigen or a variant thereof, a composition comprising additional modified cells, microorganisms (e.g., cold viruses), and/or lipid particles (e.g., Lipid nanoparticle (LNP)) comprising: the one or more nucleic acids or the antigen or a variant thereof.

2. The method of embodiment 1, wherein the modified cells comprise modified T cells, modified NK cells, modified macrophages, or modified dendritic cells.

3. The method of embodiment 1, wherein the modified cells comprise at least two different modified cells: a first modified cell comprising an antigen binding domain for expanding and/or maintaining the modified cells; and a second modified cell comprising an antigen binding domain for killing a target cell, such as a tumor cell (e.g., the solid tumor antigen).

4. The method of embodiment 3, wherein the modified cells are modified T cells.

5. The method of embodiment 3, wherein the at least two different modified cells include two different modified T cells, two different modified immune cells, or a combination thereof.

6. The method of embodiment 3, wherein the modified immune cells include modified T cells, DC cells, and/or macrophages.

7. The method of embodiment 3, wherein the antigen binding domain for expanding/or and maintaining the modified cells bind the surface antigen of a WBC, and the antigen binding domain for killing a target cell binds a tumor antigen.

8. The method of embodiment 7, wherein the WBC is a B cell.

9. The method of embodiment 7, wherein the cell surface antigen of the WBC is CD19, CD22, CD20, BCMA, CD5, CD7, CD2, CD16, CD56, CD30, CD14, CD68, CD11b, CD18, CD169, CD1c, CD33, CD38, CD138, or CD13.

10. The method of embodiment 7, wherein the cell surface antigen of the WBC is CD19, CD20, CD22, or BCMA.

11. The method of any of embodiments 1-10, wherein the solid tumor antigen is tMUC1, PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, KISS1R, QRFPR, GPR119, CLDN6, UPK2, ADAM12, SLC45A3, ACPP, MUC21, MUC16, MS4A12, ALPP, CEA, EphA2, FAP, GPC3, IL13-Rα2, Mesothelin, PSMA, ROR1, VEGFR-II, GD2, FR-α, ErbB2, EpCAM, EGFRvIII, B7-H3, EGFR, or one of those listed in Table 1.

12. The method of any of embodiments 1-10, wherein the solid tumor antigen is tMUC1, TSHR, GUCY2C, ACPP, CLDN18.2, PSMA, MAGE A4, MSLN, CD205, ADAM12, GPC-3, or UPK2.

13. The method of embodiment 1, wherein the modified cells comprise an exogenous polynucleotide encoding a therapeutic agent.

15. The method of embodiment 13, wherein the exogenous polynucleotide comprises a promoter comprising a binding site for a transcription modulator that modulates the expression and/or secretion of IL-6, IFNγ, or a combination thereof, in the modified cell.

16. The method of embodiment 14, wherein the transcription modulator comprises Hif1a, NFAT, FOXP3, or NFKB.

17. The method of any of embodiment 13-16, wherein the therapeutic agent comprises at least one of IL-1P, IL-2, IL-4, IL-5, IL-6, IL-7, IL-8, IL-10, IL-12, IL-13, IL-15, IL-17, IL-1Ra, IL-2R, IFN-γ, IFN-γ, MIP-In, MIP-IP, MCP-1, TNFα, GM-CSF, GCSF, CXCL9, CXCL10, CXCR factors, VEGF, RANTES, EOTAXIN, EGF, HGF, FGF-P, CD40, CD40L, and ferritin.

18. The method of any of embodiments 13-16, wherein the therapeutic agent comprises a costimulatory structure, activating antibody or ligand, agonist, such as CD205, CD40L, CD28L, CD137L, or a dominant negative form of an immune checkpoint molecule. In embodiments, the therapeutic agent is expressed by a target cell of the one or more nucleic acids (e.g., APC such as B cell or DC, or T cell).

19. The method of any of embodiments 1-18, wherein the modified cell comprises a modified immune checkpoint molecule (e.g., PD-1).

20. The method of embodiment 19 wherein the immune checkpoint molecule is selected from the group consisting of PD-1, cytotoxic T lymphocyte antigen-4 (CTLA-4), B- and T-lymphocyte attenuator (BTLA), T-cell immunoglobulin mucin-3 (TIM-3), lymphocyte-activation protein 3 (LAG-3), T-cell immunoreceptor with Ig and ITIM domains (TIGIT), leukocyte-associated immunoglobulin-like receptor 1 (LAIRI), natural killer cell receptor 2B4 (2B4), and CD 160.

21. The method of embodiment 19 wherein a modified PD-1 is a dominant negative form of PD-1.

22. The method of embodiment 19 wherein modified PD-1 comprises an extracellular domain of PD-1 and a cytoplasmic domain of the PD-1 polypeptide is truncated, or the modified cell has a partial or a complete deletion of the PD-1 gene and a reduced amount of PD-1 as compared to the corresponding wild-type cell, or a non-functional PD-1 gene.

23. The method of embodiment 19 wherein the modified PD-1 comprises a mutation of Tyrosine residue 223 and/or a mutation of Tyrosine residue 248.

24. The method of any embodiments 1-23, wherein the modified cells comprise a binding molecule that binds the antigen.

25. The method of embodiment 24, wherein the binding molecule is a chimeric antigen receptor.

26. The method of embodiment 25, wherein the CAR comprises an extracellular domain, a transmembrane domain, and an intracellular domain, and the extracellular domain binds a tumor antigen.

26. The method of embodiment 25, wherein the intracellular domain comprises a co-stimulatory domain that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, or a combination thereof.

27. The method of embodiment 24, wherein the intracellular domain comprises a CD3 zeta signaling domain.

28. The method of embodiment 24, wherein the binding molecule is a TCR.

29. The method of embodiment 24, wherein the modified cells comprise a modified T Cell Receptor (TCR).

30. The method of embodiment 28 or 29, wherein the TCR is derived from spontaneously occurring tumor-specific T cells in patients.

31. The method of embodiment 28 or 29, wherein the TCR binds a tumor antigen.

32. The method of embodiment 28 or 29, wherein the tumor antigen comprises CEA, gp100, MART-1, p53, MAGE-A3, or NY-ESO-1.

33. The method of embodiment 28 or 29, wherein the TCR comprises TCRγ and TCRδ chains, TCRα and TCRβ chains, or a combination thereof.

34. The method of any of embodiment 1-33, wherein the modified cells are derived from TILs. 35. The method of embodiment 1, wherein the additional modified cells comprise PBMCs, blood cells (red blood cells), DCs, B cells, and/or T cells.

36. The method of embodiment 35, wherein the additional modified cells are formulated to a vaccine. More information about the formulation of vaccines can be found at doi.org/10.2217/fon-2020-0224, doi.org/10.4155/fmc-2020-0081, doi.org/10.4155/fmc-2020-0081, and doi.org/10.4155/fmc-2020-0081, which are incorporated by their entirety.

37. The method of embodiment 1, wherein the one or more nucleic acids further comprise a polynucleotide encoding the therapeutic agent described in previous embodiments. More information about modified mRNA expressing therapeutic agents to leukocytes can be found at DOI: 10.1038/s41467-018-06936-1, which is incorporated by their entirety.

38. The method of any of embodiment 1-37, wherein a SynNotch system is added to the one or more nucleic acids to allow DC cells to express antigen outside the cell and connect intracellularly with genes that activate cells or enhance cell killing, such as cytokines and costimulatory ligands, and when the extracellular antigen recognizes the tumor, it will cause the intracellular SynNotch signal to activate the cell and enhance the CAR-T killing function. 39. The method of any of embodiments 1-38, wherein the one or more nucleic acids comprise in vitro transcribed RNA encapsulated in liposomes.

40. The method of embodiment 39, wherein the liposomes comprise N-[1-(2,3-dioleyloxy) propyl]-N,N,N-trimethylammonium chloride (DOTMA), dioleoylphosphatidylethanolamine (DOPE), or DOTMA and cholesterol.

41. The method of any of embodiments 1-40, wherein the antigen comprises a non-essential tissue antigen. More information about the non-essential tissue antigen can be found at a U.S. Pat. No. 10,793,638B.

42. The method of any of embodiments 1-40, wherein the antigen comprises a tumor-associated antigen (TAA). More information about the non-essential tissue antigen can be found at a PCT Patent Publication NO: WO2020146743, which is incorporated in its entirety. 43. The method of any of embodiments 1-40, wherein the antigen comprises a neoantigen, a class of tumor-specific antigens, differs from the traditional tumor-associated antigen (TAA). TAA is not unique to tumor tissue as it is also present in normal tissues; it is highly expressed in proliferating tumor cells expressing HER2, MART-1, MUC1, and MAGE (Li L, Goedegebuure S P, Gillanders W E. Preclinical and clinical development of neoantigen vaccines. Ann Oncol. 2017; 28: xii11-7), which is incorporated by their entirety.

44. The method of any of embodiments 1-43, wherein the antigen or the one or more nucleic acids are delivered into cells using the systems and methods described in the U.S. patent Ser. No. 10/526,573, which is incorporated by its entirety.

45. The method of any of embodiments 1-44, wherein the one or more nucleic acids are inserted into the genome of the microorganism (e.g., vaccinia viruses).

46. A polynucleotide(s) comprise the one or more nucleic acids of any of embodiments 1-45.

47. A cell comprises the polynucleotide(s) of embodiment 46.

48. A method of enhancing T cell response in a subject or treatment of a subject having cancer, the method comprising:

administering an effective amount of a composition comprising CAR T cells to the subject having a form of cancer associated with or expressing an antigen (e.g., a solid tumor antigen) that the CAR binds; and administering one or more nucleic acids encoding the antigen or a variant thereof, a level of T cell response or anti-tumor activities caused by the CAR T cells enhanced compared to a subject administered with the CAR T cells without the one or more nucleic acids.

49. A method of enhancing T cell response in a subject or treatment of a subject having cancer, the method comprising:

administering an effective amount of a composition comprising first CAR T cells targeting a first antigen (e.g., a WBC antigen such as CD19 and BCMA) to the subject having a form of cancer associated with or expressing an antigen (e.g., a solid tumor antigen);

administering an effective amount of a composition comprising second CAR T cells targeting the antigen to the subject; and in a predetermined time or response to a predetermined condition, administering one or more nucleic acids encoding the antigen or a variant thereof, a level of T cell response or anti-tumor activities caused by the CAR T cells enhanced as compared to a subject that is administered with the CAR T cells without the one or more nucleic acids.

50. The method of embodiment 49, wherein the predetermined time comprises any one of 1-30 days after administration of the CAR T cells.

51. The method of embodiment 49 wherein the predetermined condition comprises a level of second CAR T cells, or solid tumor antigen CAR copy numbers drop to a certain amount.

52. A method of enhancing T cell response in a subject or treatment of a subject having cancer, the method comprising:

administering an effective amount of a composition comprising first CAR T cells targeting a first antigen (e.g., a WBC antigen such as CD19 and BCMA) to the subject having a form of cancer associated with or expressing an antigen (e.g., a solid tumor antigen);

administering an effective amount of a composition comprising second CAR T cells targeting the antigen to the subject; and administering one or more nucleic acids encoding the antigen or a variant thereof, a level of T cell response or anti-tumor activities caused by the CAR T cells enhanced compared to a subject administered with the CAR T cells without the one or more nucleic acids.

53. A kit comprises the vaccine and CAR T cells in any of the previous suitable embodiments.

54. A lipid particle comprising: a cationic and/or pH responsive lipid, a water-soluble therapeutically effective compound, and polynucleotides encoding an antigen and one or more immune cell activators.

55. The lipid particle of embodiment 54, wherein:

the lipid particle is associated with a tumor marker associated molecule (e.g., a fibroblast activation protein binding molecule (FAPBM) as shown in FIG. 7, an antibody against tMUC1 and Prolactin), and/or the polynucleotides comprise:

a polynucleotide encoding a cytokine (e.g., IL-6, IL-2, IL-12, IL-7, and IFNγ) controlled by one or more regulatory domains (e.g., NFAT and Hifa VHL interaction domain), a CD3 agonist or antibody against a solid tumor antigen (e.g., GCC, TSHR, and ACPP), and/or an agonist of a costimulatory signal domain molecule (e.g., CD28 and 4-1BB).

56. The particle of embodiment 54 or 55, wherein the lipid forms a structure receiving the water-soluble therapeutically effective compound and the polynucleotides, and/or the particle further comprises a lamellar internal organization.

57. The particle of any one of embodiments 54 to 56, wherein the lamellar internal organization comprises 2 to 40, preferably 2 to 20, more preferably 2 to 10, in particular 3 to 8 lamellae per row.

58. The particle of any one of embodiments 54 to 57, wherein the polynucleotides are pharmaceutically active or encodes a pharmaceutically active peptide or protein.

59. The particle of any one of embodiments 54 to 58, wherein the antigen comprises a solid tumor antigen and/or a WBC antigen.

60. The particle of embodiment 59, wherein the antigen is a disease-associated antigen or elicits an immune response against a disease-associated antigen or cells expressing a disease-associated antigen.

61. The particle of any one of the embodiments is 54 to 60, wherein the therapeutically effective compound has a molecular mass of less than 1000 Da.

62. The particle of any one of embodiments 54 to 61, wherein the therapeutically effective compound is useful in immunotherapy.

63. The particle of any one of embodiments 54 to 62, wherein the therapeutically effective compound is an agent stimulating gamma-delta T cells, preferably Vgamma9Vdelta2 T cells.

64. The particle of embodiment 63, wherein the agent stimulating gamma-delta T cells is a bisphosphonate, preferably a nitrogen-containing bisphosphonate (amino bisphosphonate).

65. The particle of embodiment 63 or 64, wherein the agent stimulating gamma delta T cells are selected from the group consisting of zoledronic acid, clodronic acid, ibandronic acid, pamidronic acid, risedronic acid, minodronic acid, olpadronic acid, alendronic acid, incadronic acid and salts thereof.

66. The particle of any one of embodiments 54 to 65 comprises a helper lipid.

67. The particle of embodiment 66, wherein the helper lipid is a neutral lipid or negatively charged lipid.

68. The particle of any one of embodiments 54 to 67, wherein the a cationic lipid comprises 1,2-dimyristoyl-sn-glycero-3-ethylphosphocholine (DMEPC), 1,2-di-O-octadecenyl-3-trimethylammonium propane (DOTMA) and/or 1,2-dioleoyl-3-trimethylammonium propane (DOTAP).

69. The particle of any one of embodiments 66 to 68, wherein the helper lipid comprises 1,2-di-(9Z-octadecenoyl)-sn-glycero-3-phosphoethanolamine (DOPE), cholesterol (Choi), 1-palmitoyl-2-oleoyl-sn-glycero-3phosphocholin (POPC) and/or 1,2-dioleoyl-sn-glycero-3-phosphocholine (DOPC).

70. The particle of any one of embodiments 54 to 69, wherein the particle has an average diameter in the range of from about 50 nm to about 1000 nm.

71. The particle of embodiment 70, wherein the particle has an average diameter in the range of from about 50 nm to about 400 nm, preferably from about 50 nm to about 200 nm, or in the range of from about 200 nm to about 1000 nm, preferably from about 200 nm to about 800 nm, more preferably from about 300 nm to about 600 nm.

72. The particle of any one of embodiments 54 to 71, wherein the particle is obtainable by addition of the polynucleotides to a colloidal lipid dispersion comprising the cationic lipid and the water-soluble therapeutically effective compound.

73. The particle of embodiment 72 wherein the colloidal lipid dispersion comprising the cationic lipid and the water-soluble therapeutically effective compound is obtainable by injection of an ethanol solution of the lipids into an aqueous phase comprising the water-soluble therapeutically effective compound.

74. A pharmaceutical composition comprising particles as set forth in any one of embodiments 54 to 73.

75. The pharmaceutical composition of embodiment 74, wherein, after systemic administration of the particles, a portion of the polynucleotides and a portion of the therapeutically effective compound are delivered to a target cell, preferably to the target cell.

76. The pharmaceutical composition of embodiment 75, wherein a portion of the polynucleotides and a portion of the therapeutically effective compound are delivered to the cytosol of the target cell.

77. The pharmaceutical composition of embodiment 75 or 76, wherein the polynucleotides comprise RNAs encoding a peptide or protein, and the polynucleotides are translated by the target cell to produce the peptide or protein.

78. The pharmaceutical composition of any one of embodiments 75 to 77, wherein the target cell is a spleen cell, preferably an antigen presenting cell, more preferably a professional antigen presenting cell, more preferably a dendritic cell.

79. The pharmaceutical composition of any one of embodiments 74 to 78, wherein, after systemic administration of the particles, polynucleotides accumulation and/or polynucleotides expression in the spleen occurs.

80. The pharmaceutical composition of any one of embodiments 74 to 79, wherein, after systemic administration of the particles, no or essentially no polynucleotide accumulation and/or polynucleotide expression in the lung and/or liver occurs.

81. The pharmaceutical composition of any one of embodiments 74 to 80, wherein, after systemic administration of the particles, polynucleotide accumulation and/or polynucleotide expression in the spleen is at least 5-fold the amount of polynucleotide accumulation and/or polynucleotide expression in the lung and/or liver.

82. The pharmaceutical composition of any one of embodiments 74 to 81, wherein, after systemic administration of the particles, polynucleotide accumulation and/or polynucleotide expression in antigen presenting cells, preferably professional antigen presenting cells in the spleen, occurs.

83. The pharmaceutical composition of embodiment 82, wherein the antigen presenting cells are dendritic cells and/or macrophages.

84. The pharmaceutical composition of any one of embodiments 75 to 83, wherein systemic administration is by parenteral administration, preferably by intravenous administration, subcutaneous administration, intradermal administration, or intraarterial administration.

85. The pharmaceutical composition of any one of the embodiments of 74 to 84, wherein the composition comprises one or more pharmaceutically acceptable carriers, diluents, and/or excipients.

86. The pharmaceutical composition of any one of embodiments 74 to 85, wherein the composition further comprises an adjuvant.

87. The pharmaceutical composition of any one of embodiments 74 to 86, wherein the composition is formulated for systemic administration.

88. The pharmaceutical composition of any one of embodiments 74 to 87 for inducing or enhancing an immune response, preferably an immune response against cancer.

89. The pharmaceutical composition of any one of embodiments 74 to 88 for use in a prophylactic and/or therapeutic treatment of a disease involving an antigen, preferably a cancer disease.

90. A method for delivering an antigen to antigen presenting cells, preferably professional antigen presenting cells, in the spleen, or expressing an antigen in antigen presenting cells, preferably professional antigen presenting cells, in the spleen comprising administering to a subject a pharmaceutical composition of any one of embodiments 74 to 87.

91. The method of embodiment 90, wherein the antigen presenting cells are dendritic cells and/or macrophages.

92. A method for inducing or enhancing an immune response, preferably an immune response against cancer, in a subject comprising administering to the subject a pharmaceutical composition of any one of embodiments 74 to 87.

93. A method for stimulating, priming, and/or expanding T cells in a subject comprising administering to the subject a pharmaceutical composition of any one of embodiments 74 to 87.

94. A method of treating or preventing a disease involving an antigen, preferably a cancer disease, in a subject comprising administering to the subject a pharmaceutical composition of any one of embodiments 74 to 87.

95. A method of producing a particle of any one of embodiments 54 to 73 comprising the following steps of:

(i) providing a colloidal lipid dispersion comprising one cationic lipid and one water-soluble therapeutically effective compound, and (ii) adding polynucleotides to the lipid dispersion comprising one cationic lipid and one water-soluble therapeutically effective compound.

96. The method of embodiment 95 wherein the colloidal lipid dispersion comprising one cationic lipid and one water-soluble therapeutically effective compound is provided by injection of an ethanol solution of lipids into an aqueous phase comprising the one water-soluble therapeutically effective compound.

97. The method of embodiment 95 or 96, wherein the number of positive charges derived from the cationic lipids divided by the number of negative charges derived from the polynucleotides is between 0.025 and 4.

98. The pharmaceutical composition, the particle, the lipid particle, the method of any of embodiments 54-97, wherein the one or more immune cell activators are one or more T cell activators.

99. The pharmaceutical composition, the particle, the lipid particle, the method of embodiment 98, wherein the one or more T cell activators comprise CD28 antibodies.

100. The pharmaceutical composition, the particle, the lipid particle, the method of embodiment 98, wherein the one or more T cell activators comprise CD3 antibodies.

101. The pharmaceutical composition, the particle, the lipid particle, the method of embodiment 98, wherein the one or more T cell activators comprise 4-1BB antibodies.

102. The pharmaceutical composition, the particle, the lipid particle, the method of embodiment 98, wherein the one or more T cell activators comprise CD 80 ligands.

103. The pharmaceutical composition, the particle, the lipid particle, the method of embodiment 98, wherein the one or more T cell activators comprise CD86 ligands.

104. The pharmaceutical composition, the particle, the lipid particle, the method of embodiment 98, wherein the one or more T cell activators comprise a molecule binding a costimulatory receptor.

105. The pharmaceutical composition, the particle, the lipid particle, the method of any of embodiments 54-97, wherein the one or more immune cell activators are one or more NK cell activators.

106. The pharmaceutical composition, the particle, the lipid particle, the method of embodiment 105, wherein the one or more T cell activators comprise CD2 antibodies.

107. The pharmaceutical composition, the particle, the lipid particle, the method of embodiment 98, wherein the one or more T cell activators comprise CD335 antibodies.

108. The pharmaceutical composition, the particle, the lipid particle, the method of any of embodiments 54-107, wherein the polynucleotides comprise an RNA.

109. The pharmaceutical composition, the particle, the lipid particle, the method of any of embodiments 54-107, wherein the polynucleotides comprise an mRNA.

110. A method for inducing or enhancing an immune response, preferably an immune response against cancer, in a subject comprising administering to the subject a pharmaceutical composition of any one of embodiments 74 to 87 and 98 to 109.

111. The method of embodiment 110, further comprising: administering to the subject a pharmaceutical composition comprising a population of immune cells comprising a binding molecule.

112. The method of embodiment 111, wherein the immune cells are NK and/or T cells.

113. The method of embodiment 111, wherein the binding molecule is a CAR or TCR.

114. The method of any of embodiments 111-113, wherein the immune cells comprise a polynucleotide encoding IL-12.

115. The composition and method of any suitable preceding embodiments, wherein sequences thereof may be found at Applicants' PCT Patent Application No: PCT/US21/31258 and PCT/US2021/028429, which are incorporated herein by their entirety.

116. A method of delivery drugs to a microenvironment of tumor cells expressing a solid tumor antigen, the method comprising:

administering an effective amount of a population of CART cells comprising a chimeric antigen receptor (CAR), the CAR binding the solid tumor antigen, the CART cells engineered to express and secret multiple therapeutic agents in response to the binding of the CAR and the solid tumor antigen, the multiple therapeutic agents comprising IL-12 or IFNγ; and allowing the CART to bind cells of the tumor cells, thereby releasing the multiple agents to microenvironment of the tumor cells.

117. A method of overcoming tumor heterogeneity, the method comprising:

preparing mixed CAR T cells comprising first CAR T cells engineered to express a CAR and second CAR T cells engineered to express the CAR and a polynucleotide encoding a therapeutic agent;

contacting tumor cells with the mixed CAR T cells, the tumor cells comprising multiple tumor antigens or epitopes, the CAR binding a tumor antigen or epitope of the multiple tumor antigens or epitopes;

allowing T cell response caused by the mixed CAR T cells on the tumor cells, wherein the T cell response is greater than T cell response caused by the first CAR T cells without the second CAR T cells.

118. The method of embodiment 117, wherein the multiple tumor antigens comprise another tumor antigen or epitope that the CAR does not bind.

119. The method of embodiment 117, wherein the T cells response is measured based on a level of cytokine release, a level of anti-tumor activity, and/or a level of expansion of CAR T cells.

120. The method of embodiment 117, wherein the therapeutic agent is IL-12.

121. The method of embodiment 117, wherein the therapeutic agent is IFNγ.

122. The method of embodiment 117, wherein expression of the polynucleotide is regulated by an NFAT promoter.

123. The method of embodiment 117, wherein the mixed CAR T cells comprise, at least, two of: a CAR T cell engineered to expressing the CAR, a CAR T cell engineered to expressing the CAR and IL-12, a CAR T cells engineered to expressing the CAR and IFNγ, and a CAR T cells engineered to expressing the CAR, IL-12, and IFNγ. 124. The method of embodiment 117, wherein the CAR comprises a co-stimulatory domain of CD28.

125. A method of treating a subject having cancer cells expressing a solid tumor antigen and/or enhancing treatment of the subject, the method comprising the steps described in any of embodiments 117-124.

126. The method of any of embodiments 116-125, wherein the therapeutic agent comprises a fusion protein (e.g., polyspecific antibody) comprising: a first antigen binding domain targeting a receptor of a first immune cell; a second antigen binding domain targeting a receptor of a second immune cell; and a third antigen binding domain targeting a tumor antigen.

127. The method of any of embodiments 116-125, wherein the therapeutic agent comprises a first fusion protein (e.g., polyspecific antibody) comprising a first antigen binding domain targeting a receptor of a first immune cell and an antigen binding domain targeting a tumor antigen; and a second antigen binding domain targeting a receptor of a second immune cell and an antigen binding domain targeting a tumor antigen.

128. The method of embodiments 126 or 127, wherein the first immune cell is a T cell, and the second immune cell is a DC or macrophage.

129. The method of any preceding suitable embodiments, wherein the fusion is a bispecific or a trispecific antibody.

130. The method of any preceding suitable embodiments, wherein the receptor of the first immune cell and the receptor of the second immune cell are selected from receptors in the below immune cell's receptors such as monocyte/CD16, CD32, CD64, Mannose receptor (MR), Scavenger receptor (SR), Toll-like receptor (TLR), Phosphatidylserine receptor (PSR), CD14, CD40; NK cell/CD16, NKp46, NKp30, NKp44, NKp80, NKG2D, KIR-S, CD94/NKG2C, CRACC, Ly9, CD84, NTBA, CD3Z, 41BB, CD28, 2B4; imDC/Complement receptor, FcR, MR, TLR; mDC/Basic granulocyte, FcεRI, Acid granulocyte, FcεRI, Mast cells, FcεRI, FcγRIII; NKT/γδT cell; Innate lymphoid cell/Neutrophil; Dectin-1, Mac-1, TREM-1, TLR1, TLR2, TLR3, TLR4, TLR5, TLR6, TLR7, TLR8, TLR9, TLR10, NOD1, NOD2, CR4, CR1 (CD35), FcγR; T cell/CD3, CD28, 41BB, and OX40.

131. The method of any preceding suitable embodiments, wherein the fusion protein further comprises a therapeutic agent (such as a cytokine), and information of antibody cytokine fusion proteins can be found at Schmid AS, Tintor D, Neri D. Novel antibody-cytokine fusion proteins featuring granulocyte-colony stimulating factor, interleukin-3 and interleukin-4 as payloads. J Biotechnol. 2018; 271:29-36. doi: 10.1016/j.jbiotec.2018.02.004, which is incorporated by reference in its entirety.

132. The method of embodiment 131, wherein the therapeutic agent comprises or is a cytokine or one of the other anti-tumor molecules such as chemotherapy payload.

133. The method of embodiment 132, wherein the cytokine comprises or is at least one of IL-12, IL-6, and IFNγ.

134. The method of any preceding suitable embodiments, wherein the first antigen binding domain comprises an agonistic antibody corresponding to the receptor of the first immune cell, and/or the second antigen binding domain comprises an agonistic antibody corresponding to the receptor of the second immune cell.

135. The method of any preceding suitable embodiments, wherein the solid tumor antigen is a non-essential tissue antigen.

136. The method of any of the preceding embodiments, wherein the expression of the therapeutic agent is implemented by introducing a nucleic acid sequence encoding the therapeutic agent and/or the CAR, which is present in the modified cell in a recombinant DNA construct, in an mRNA, or in a viral vector.

137. The method of embodiment 136, wherein the nucleic acid sequence is an mRNA, which is not integrated into the genome of the modified cell.

138. The method of embodiment 136, wherein the nucleic acid sequence is associated with an oxygen-sensitive polypeptide domain.

139. The method of embodiment 136, wherein the oxygen-sensitive polypeptide domain comprises HIF VHL binding domain.

140. The method of embodiment 136, wherein the nucleic acid sequence is regulated by a promoter comprising a binding site for a transcription modulator that modulates the expression and/or secretion of the therapeutic agent in the cell.

141. The method of embodiment 140, wherein the transcription modulator is or includes Hif1a, NFAT, FOXP3, and/or NFKB.

142. The method of any of the preceding embodiments, wherein the CAR comprises an antigen-binding domain, a transmembrane domain, and an intracellular signaling domain.

143. The method of embodiment 142, wherein the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

144. The method of any one of embodiments 142 and 143, wherein the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D 145. The method of any one of embodiments 116-144, wherein the CAR is replaced by a modified TCR.

146. The method of embodiment 145, wherein the TCR is derived from spontaneously occurring tumor-specific T cells in patients.

147. The method of embodiment 145, wherein the TCR binds to a tumor antigen.

148. The method of embodiment 147, wherein the tumor antigen comprises CEA, gp100, MART-1, p53, MAGE-A3, or NY-ESO-1.

149. The method of embodiment 145, wherein the TCR comprises TCRγ and TCRδ Chains or TCRα and TCRβ chains, or a combination thereof.

150. The method of any of the preceding embodiments, wherein the T cell is replaced by an NK cell.

151. The method of any of the preceding embodiments, wherein the cells comprise a nucleic acid sequence encoding a binding molecule and a dominant negative form of an inhibitory immune checkpoint molecule or a receptor thereof.

152. The method of embodiment 151, wherein the inhibitory immune checkpoint molecule is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRI), natural killer cell receptor 2B4 (2B4), and CD 160.

153. The method of embodiment 152, wherein inhibitory immune checkpoint molecule is modified PD-1.

154. The method of embodiment 152, wherein the modified PD-1 lacks a functional PD-1 intracellular domain for PD-1 signal transduction, interferes with a pathway between PD-1 of a human T cell of the human cells and PD-L1 of a certain cell, comprises or is a PD-1 extracellular domain or a PD-1 transmembrane domain, or a combination thereof, or a modified PD-1 intracellular domain comprising a substitution or deletion as compared to a wild-type PD-1 intracellular domain, or comprises or is a soluble receptor comprising a PD-1 extracellular domain that binds to PD-L1 of a certain cell.

155. The method of any of the preceding embodiments, wherein the modified cell has a reduced expression of endogenous TRAC gene.

156. The method of any of the preceding embodiments, wherein the modified cell comprises a first CAR binding a white blood antigen and a second CAR binding a solid tumor antigen.

157. The method of any of the preceding embodiments, wherein the modified cell comprises a bispecific CAR binding a white blood antigen and a solid tumor antigen.

158. The method of any of the preceding embodiments, further comprising: administering an effective amount of additional modified cell binding white blood cell antigen.

159. The method of embodiment 158, wherein the white blood cell antigen is CD19, CD22, CD20, BCMA, CD5, CD7, CD2, CD16, CD56, CD30, CD14, CD68, CD11b, CD18, CD169, CD1c, CD33, CD38, CD138, or CD13.

160. The method of embodiment 158, wherein is CD19, CD20, CD22, or BCMA. 161. The method of any of the preceding embodiments, wherein the therapeutic agent comprises or is CCR2, CCR4, CXCR3, CCR6, ICAM3, CCR7, LFA-3, CCR1, CCR3, or CCR5.

162. A method of treating a subject having a form of cancer, the method comprising: obtaining lymphocytes from a subject;

mixing the lymphocytes with one or more activators to obtain pretreated or pre-complexed lymphocytes; and administering an effective amount of the pretreated or pre-complexed lymphocytes to the subject.

163. A method of treating a subject having a form of cancer, the method comprising: obtaining lymphocytes from a healthy donor;

modifying the lymphocytes such that immune responses to the transplanting of the lymphocytes is reduced (e.g., reduced expression of TCR and/or HLA on the lymphocytes);

mixing the lymphocytes with one or more activators to obtain pretreated or pre-complexed lymphocytes; and administering an effective amount of the pretreated or pre-complexed lymphocytes to the subject.

164. The method of embodiment 162 or 163, further comprising:

culturing the pre-treated or pre-complexed lymphocytes for a time period before the infusing; and removing a certain portion of the lymphocytes from the pre-treated or pre-complexed lymphocytes based on a surface or phenotype marker (e.g., CD4, CD8), morphology, or behavior of the lymphocytes.

165. The method of any embodiment of embodiments 66-68, further comprising:

administering an effective amount of bispecific antibodies to the subject, wherein the bispecific antibodies bind a target cell (e.g., tumor cells) and one or more of the pre-complexed lymphocytes.

166. The method of embodiment 165, wherein the bispecific antibodies bind CD3 and a solid tumor antigen (e.g., GCC) or a WBC antigen (e.g., CD19), and the pre-complexed lymphocytes comprise T cells.

167. The method of embodiment 165, wherein the bispecific antibodies bind CD16A and a solid tumor antigen (e.g., GCC) or a WBC antigen (e.g., CD30), and the pre-complexed lymphocytes comprise NK cells.

168. The method of any embodiment of embodiments 66-71, wherein the pre-complexed lymphocytes comprises CAR T cells and/or CAR NK cells.

169. A composition comprising NK cells comprising a CAR targeting a solid tumor antigen and NK cells comprising a CAR targeting a WBC antigen.

170. A composition comprising NK cells comprising a CAR targeting a solid tumor antigen and T cells comprising a CAR targeting a WBC antigen, wherein the expression of TCR and/or HLA on the T cells is reduced.

171. A composition comprising NK cells comprising a CAR targeting a solid tumor antigen and a population of T cells comprising a first population of T cells targeting a WBC antigen and a second population of T cells targeting a solid tumor antigen (e.g., CoupledCAR®).

172. A method of treating a subject having a form of cancer, the method comprising: administering an effective amount of NK cells comprising a CAR targeting a solid tumor antigen; and administering an effective amount of NK or T cells comprising a CAR targeting a WBC antigen.

173. A method of treating a subject having a form of cancer, the method comprising: administering an effective amount of NK cells;

administering an effective amount of NK or T cells comprising a CAR targeting a WBC antigen; and administering an effective amount of bispecific antibodies to the subject, wherein the bispecific antibodies bind a target cell (e.g., tumor cells) and one or more of the pre-complexed lymphocytes.

174. The composition of any of embodiments 169-173, wherein the T cells comprising T cells overexpressing at least one of IL-12, IL6, and IFNγ, including any combination thereof. 175. The composition of any of embodiments 169-174, wherein the NK cells comprising NK cells overexpressing at least one of IL-12, IL6, and IFNγ, including any combination thereof. 176. The composition of any of embodiments 162-175, wherein the NK cells are cord-blood NK (cdNK) cells.

EXAMPLES

Lentiviral vectors that encode individual CAR molecules were generated and transfected with T cells, as explained below. Techniques related to cell cultures and cytotoxic T lymphocyte assay may be found in "Control of large, established tumor xenografts with genetically retargeted human T cells containing CD28 and CD137 domains," PNAS, Mar. 3, 2009, vol. 106 no. 9, 3360-3365 and "Chimeric Receptors Containing CD137 Signal Transduction Domains Mediate Enhanced Survival of T Cells and Increased Antileukemic Efficacy In Vivo," Molecular Therapy, August 2009, vol. 17 no. 8, 1453-1464, which are incorporated herein by reference in their entirety.

Substrate cells (e.g., K562 cells) were transduced with lentivirus, including nucleic acid sequences encoding various antigens to establish target tumor cell lines. The lentivirus included the IRES-mCherry construct, which encodes red fluorescence to confirm antigen expression. The red fluorescent signals of these substrate cells were observed, indicating that the target solid tumor cell lines were successfully established. Techniques for constructing cell lines may be found at "Chimeric Receptors Containing CD137 Signal Transduction Domains Mediate Enhanced Survival of T Cells and Increased Antileukemic Efficacy In Vivo Molecular Therapy vol. 17 no. 8, 1453-1464 August 2009," which is incorporated herein by reference. K562 cells were obtained from American Type Culture Collection (ATCC).

Primary T cells were transduced with lentivirus vectors (see table below) to generate mixed CAR T cells. The primary T cells were obtained from healthy human donors. The lentivirus included nucleic acid sequence encoding CAR molecules and one or more therapeutic agents, and may further include the IRES-mCherry construct, which encodes red fluorescence for confirmation of CAR expression. Techniques related to cell cultures, construction of lentiviral vectors, and flow cytometry may be found in "Treatment of Advanced Leukemia in Mice with mRNA-Engineered T Cells, HUMAN GENE THERAPY 22:1575-1586 (December 2011)", which is incorporated herein by reference. After the transduction, mixed T cells were analyzed to determine individual cell types and percentages.

Each type of CAR T cells and the corresponding type of antigen-expressed cells were co-cultured, and CAR T cells' response induced by the antigen-express K562 cells were measured. A ratio of E:T (i.e., CAR T cells: target tumor cells) of CAR T cells and target tumor cells were co-cultured for 24 hours. The supernatant was then collected, and the release of IFN-γ was measured. Various levels of IFN-γ release were observed when CAR T cells and their corresponding antigen-expressing K562 cells were co-cultured. In addition, cytokines, such as IFNγ, were measured.

CAR T cell killing assays were conducted to measure the effectiveness of CAR T cells. Primary T cells were obtained from blood samples of healthy human donors. These primary T cells were transduced with a nucleic acid sequence encoding various CARs, and CAR expression on T-cells was measured using flow cytometry techniques.

TABLE 3

Vector MOI and Estimates of Transduction Rates

| Vector MOI | Construct of CAR and Therapeutic Agent or dnPD-1 (if not specified, costimulatory domain is 41-BB) | Theoretical single-turn ratio | Estimated single-turn ratio |
|---|---|---|---|
| Group 1 | | | |
| 30 | scFv/GCC, | 30.00% | 15.00% |
| 10 | scFv/CD19- IFNγ, | 10.00% | 5.00% |
| 1 | scFv/CD19-IL6, | 1.00% | 0.50% |
| 1 | scFv/CD19-IL12, | 1.00% | 0.50% |
| Group 2 | | | |
| 10 | scFv/PAP-CD28- IFNγ, | 10.00% | 5.00% |
| 10 | scFv/PAP-IL12, | 10.00% | 5.00% |
| 10 | scFv/PAP-dnPD1-IL6 | 10.00% | 5.00% |
| 10 | scFv/CD19- IFNγ, | 10.00% | 5.00% |
| Group 3 | | | |
| 10 | scFv/PAP-CD28- IFNγ | 10.00% | 5.00% |
| 10 | scFv/PAP-IL12, | 10.00% | 5.00% |
| 10 | scFv/PAP-dnPD1-IL6 | 10.00% | 5.00% |
| 20 | scFv/CD19- IFNγ, | 20.00% | 10.00% |

TABLE 4

Measured Transduction Rates for Group 1

| | | |
|---|---|---|
| GCC+ | 17.39% | 17.88% |
| CD19+IFNγ+ | 4.64% | 2.21% |
| CD19+IL6+ | 0.05% | 0.09% |
| CD19+IL12+ | 0.28% | 0.20% |
| GCC+CD19+IFNγ+ | 4.17% | 2.47% |
| GCC+CD19+IL6+ | 0.08% | 0.06% |
| GCC+CD19+IL12+ | 0.33% | 0.09% |
| CD19+IFNγ+IL6+ | 0.07% | 0% |

TABLE 4-continued

| Measured Transduction Rates for Group 1 | | |
|---|---|---|
| CD19+IFNγ+IL12+ | 0.03% | 0.02% |
| CD19+IL6+IL12+ | 0% | 0% |
| GCC+CD19+IFNγ+IL6+ | 0.15% | 0.06% |
| GCC+CD19+IFNγ+IL12+ | 0.04% | 0.05% |
| GCC+CD19+IL6+IL12+ | 0% | 0% |
| CD19+IFNγ+IL6+IL12+ | 0.05% | 0.03% |
| GCC+CD19+IFNγ+IL6+IL12+ | 0.01% | 0.02% |
| CD19+, no vector-cytokine | 3.07% | 2.59% |
| GCC+CD19+, no vector cytokine | 2.68% | 1.58% |
| Un-transduced T | 66.95% | 72.64% |
| Summary | | |
| GCC+ | 24.85% | 22.21% |
| CD19+ | 12.97% | 7.89% |
| GCC+CD19+ | 7.46% | 4.33% |

TABLE 5

| ID | SEQ |
|---|---|
| GCC-LNP amino acid | SEQ ID NO: 1 |
| GCC-LNP Polynucleotide | SEQ ID NO: 2 |
| GFP-LNP amino acid | SEQ ID NO: 3 |
| GFP-LNP Polynucleotide | SEQ ID NO: 4 |
| Anti-GCC scFv | SEQ ID NO: 5 |
| Anti-GCC CAR | SEQ ID NO: 6 |
| CD80 aa CAR | SEQ ID NO: 7 |
| CD86 aa CAR | SEQ ID NO: 8 |
| TNFSF9/41BBL aa CAR | SEQ ID NO: 9 |
| CD28 antibody aa//Anti-CD28 antibody scFv-(mAb 9.3) CAR (VH and VL) | SEQ ID NO: 10 and 11 |
| 41BB antibody (Anti-CD137 antibody scFv) CAR (VH and HL) | SEQ ID NO: 12 and 13 |
| IL 15 aa CAR | SEQ ID NO: 14 |
| IL21 aa CAR | SEQ ID NO: 15 |
| IL23A (Associates with IL12B to form the IL-23 interleukin, a heterodimeric cytokine which functions in innate and adaptive immunity) CAR | SEQ ID NO: 16 |
| IL12B aa CAR | SEQ ID NO: 17 |
| IL12 aa CAR | SEQ ID NO: 18 |
| IL18 aa CAR | SEQ ID NO: 19 |
| CCL5 aa CAR | SEQ ID NO: 20 |
| CCL22 aa CAR | SEQ ID NO: 21 |
| IL2 aa CAR | SEQ ID NO: 22 |
| IL7 aa CAR | SEQ ID NO: 23 |

Figure 18:
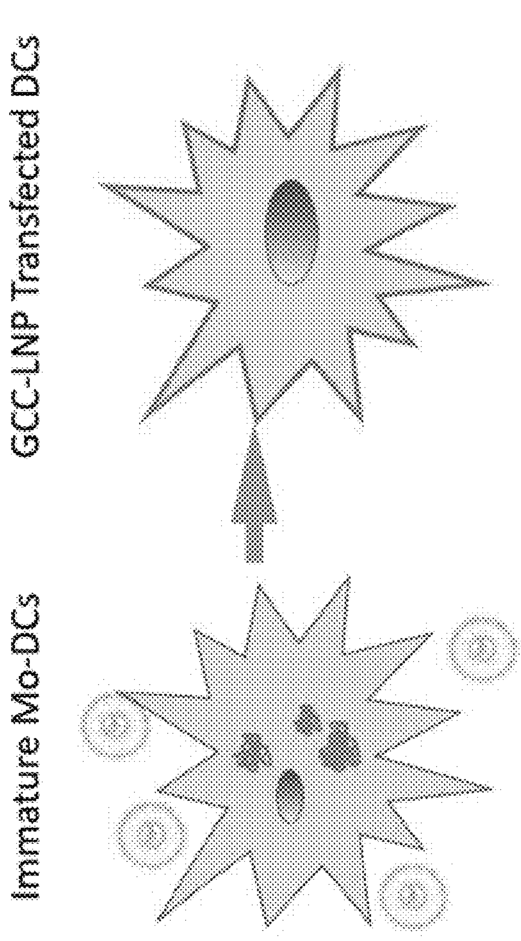
FIG. 18 shows schematic diagrams of the preparation of LNPs containing polynucleotides and the transfection of DCs using the LNPs.
Figure 18:
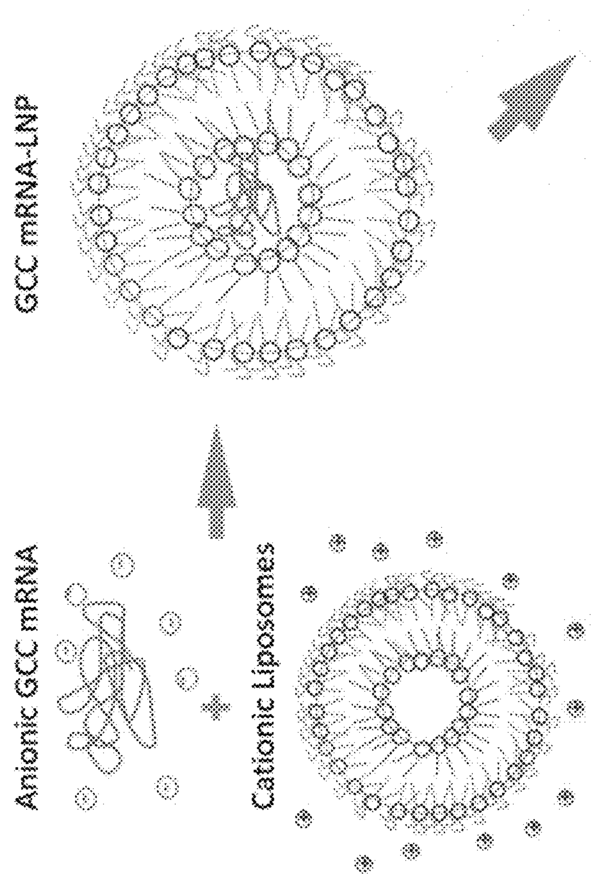
Figure 19A:
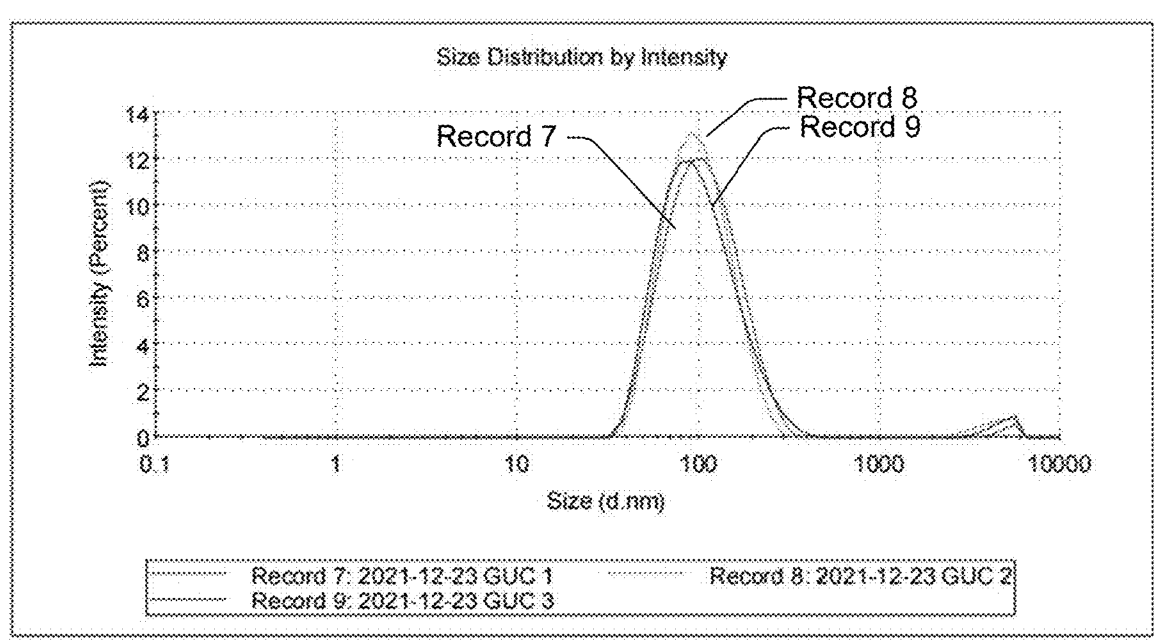
FIGS. 19A and 19B show the average particle size of GCC-LNP and GFP-LNP.
Figure 19B:
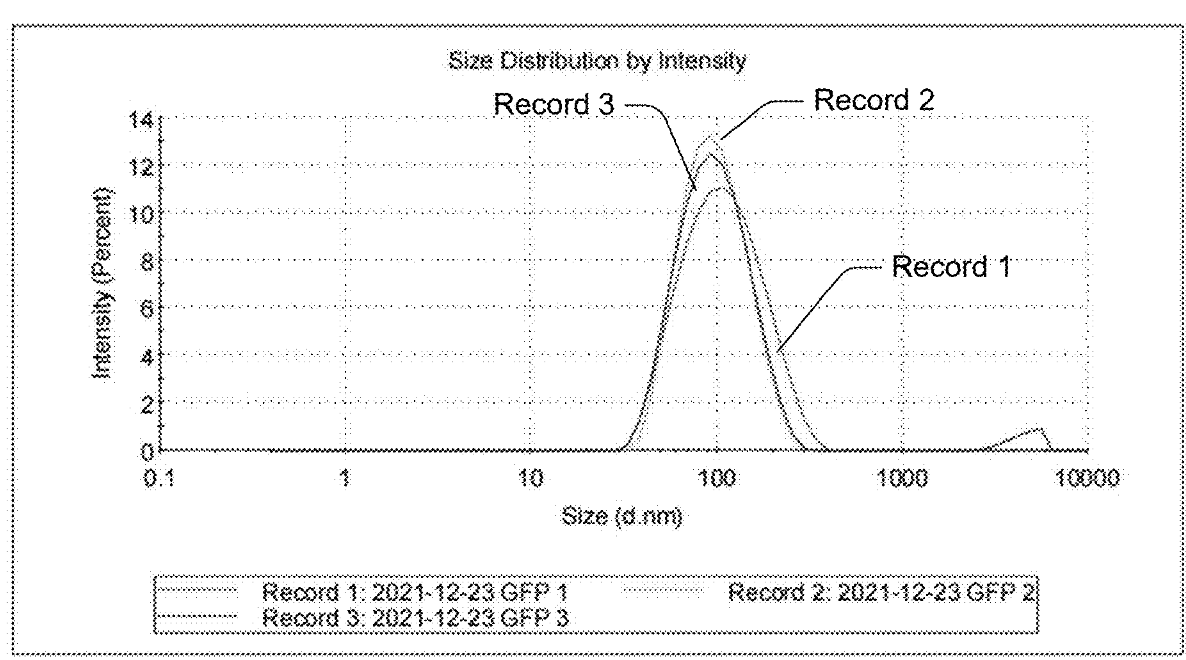

FIG. 18 show schematic diagrams for the preparation of LNPs containing polynucleotides and transfection of DCs using the LNPs. GCC-LNP transfected DCs were generated by mixing anionic GCC mRNA with cationic liposomes. FIG. 19 shows the average particle size of GCC-LNP and GFP-LNP. FIG. 20 shows GCC-LNP & GFP-LNP encapsulation efficiency and encapsulated RNA Concentration. The Nanoassembler®, Ignite™ System instrument, LNP kit Nanoassembler®, Ignite™ Training Kit, and GenVoy-ILM™ was used for GCC mRNA wrapping. More information about LNP and its uses in cell therapies can be found at PCT Publication NOS: WO2020206231, WO2005120469, WO2021021634, WO2019014623, and WO2016155809 and Reinhard et al., A nanoparticle RNA vaccine strategy targets chimeric antigen receptor (CAR)-T cells to solid tumors in difficult-to-treat mouse models, SCIENCE 24 Jan. 2020:446-453, which are incorporated herein by their entirety.

Figures 21A, 21B, 21C:
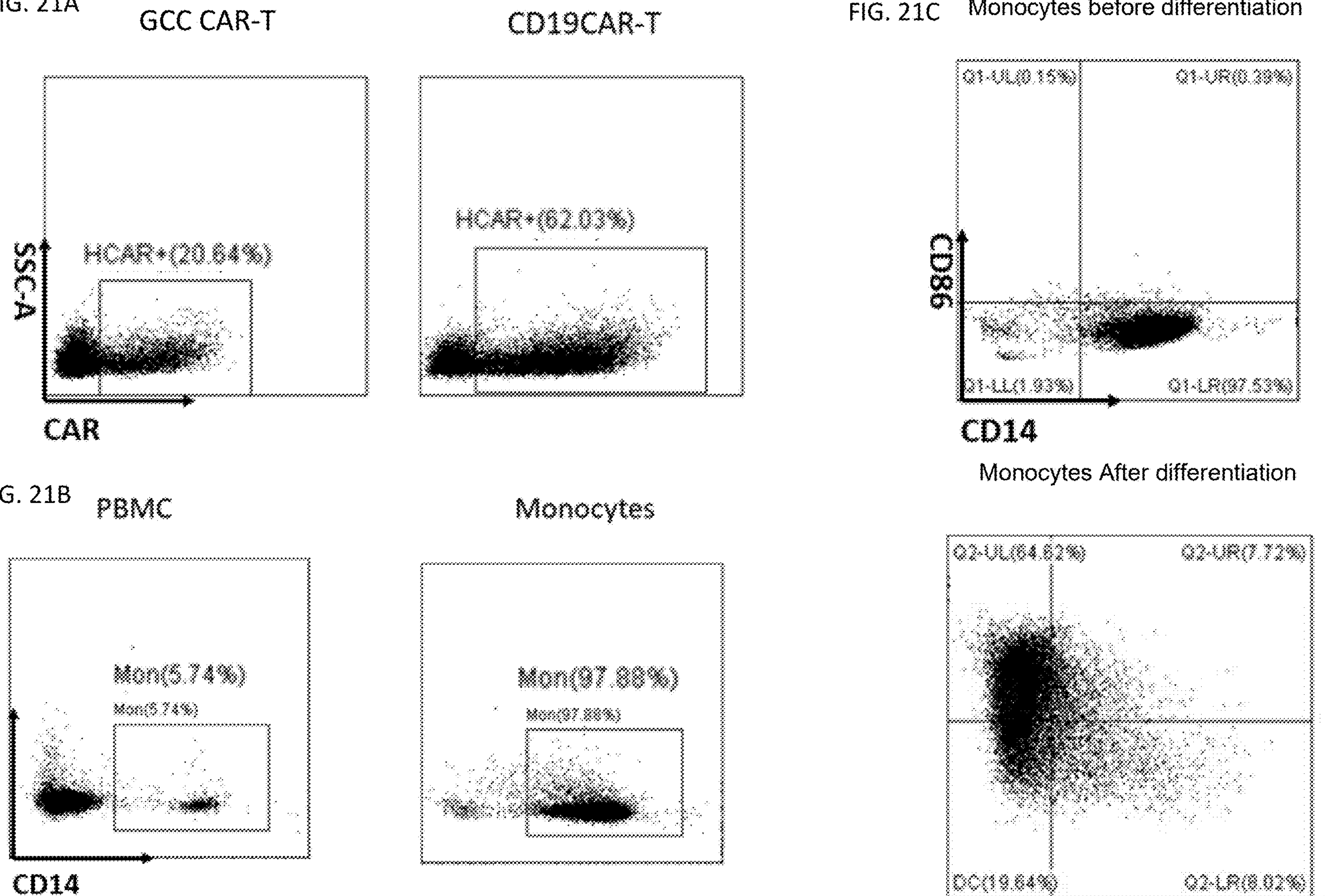
FIGS. 21A, 21B, and 21C show results of flow cytometry analysis confirming that CAR T cells and DCs were obtained.

FIGS. 21A, 21B, and 21C show results of flow cytometry analysis confirming that CAR T cells and DCs were obtained. T cells and monocytes were obtained from the peripheral blood of healthy volunteers. T cells were transfected with lentivirus encoding CAR to obtain CAR T cells (e.g., GCC CAR T cells). The monocytes were differentiated into DC cells (i.e., CD14 negative and CD86 negative).

Figure 22:
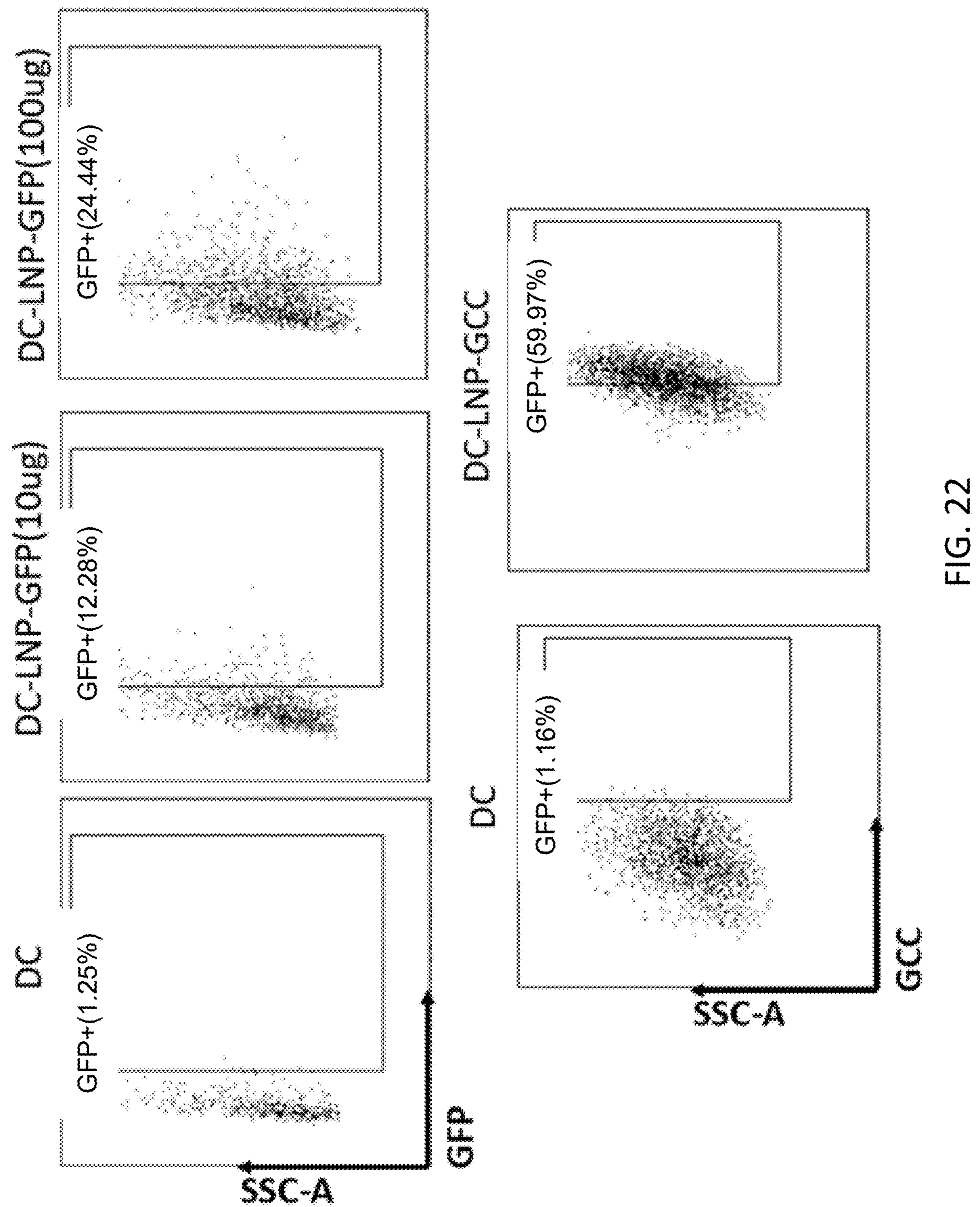
FIG. 22 show results of flow cytometry analysis confirming differentiated DC cells were transfected with LNP-GFP or LNP-GCC.

FIG. 22 show results of flow cytometry analysis confirming that differentiated DC cells were transfected with LNP-GFP or LNP-GCC. DCs were mixed with 10 ug or 100 ug of LNPs, and expression of GFP or GCC was determined. DCs mixed with 100 ug of LNPs showed higher transfection rates.

Figures 23A, 23B, 23C, 23D:
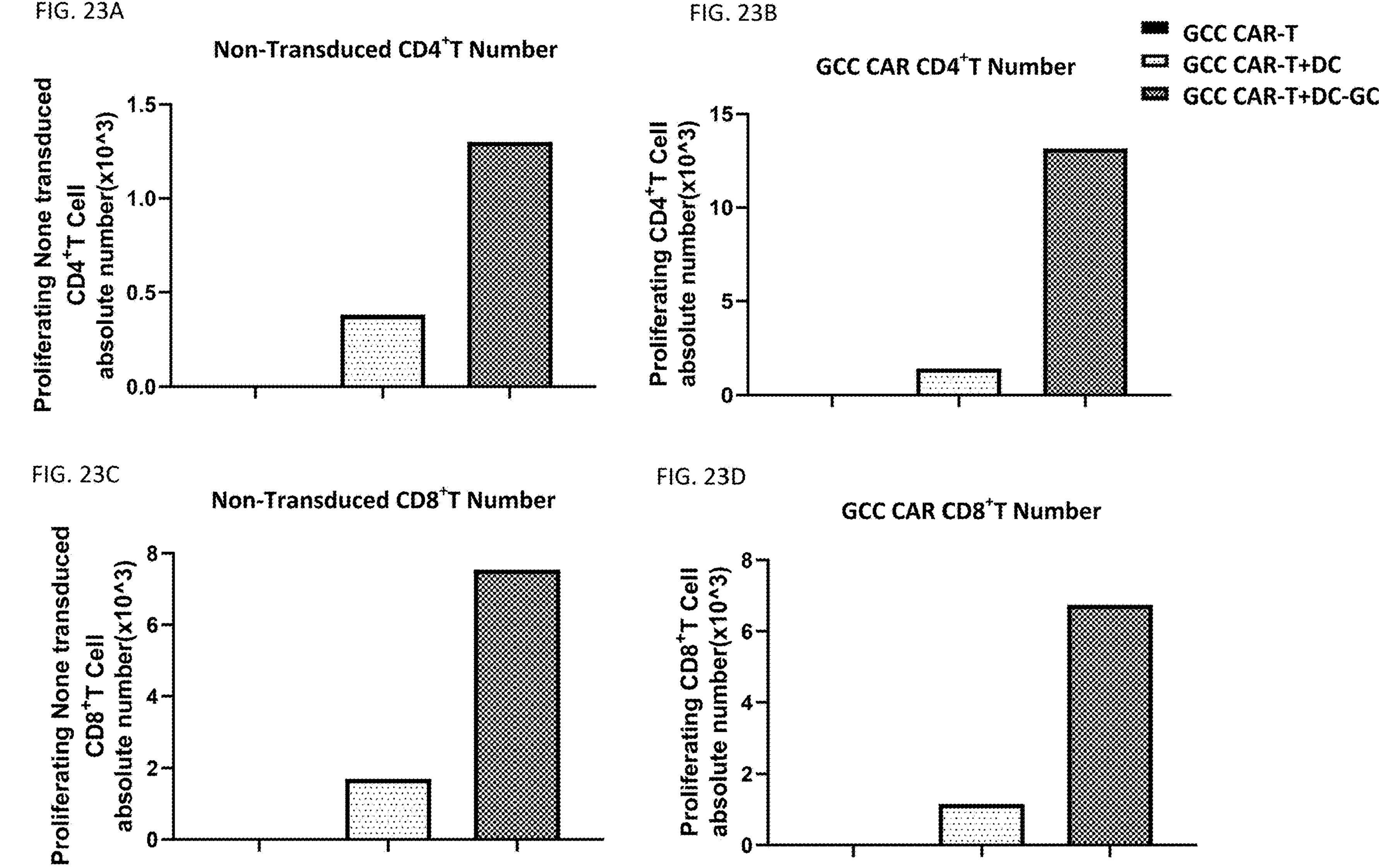
FIGS. 23A, 23B, 23C, and 23D show that DCs transfected with LNP-GCC enhanced expansion of both GCC CAR T cells and non-transduced T cells.

FIG. 23 shows that DCs transfected with LNP-GCC enhanced expansion of both GCC CAR T cells and non-transduced T cells. After the differentiated DC cells were transfected with LNP-GCC, they were co-cultured with mixed cells including GCC CAR T cells and non-transduced T cells (E:T=1:1). Expansion analysis of T cells was performed using Celltrace™. It was found that, after co-culturing with DC-GCC, GCC CAR T cells showed expansion, and non-transduced T cells also showed expansion.

Figures 24A, 24B, 24C:
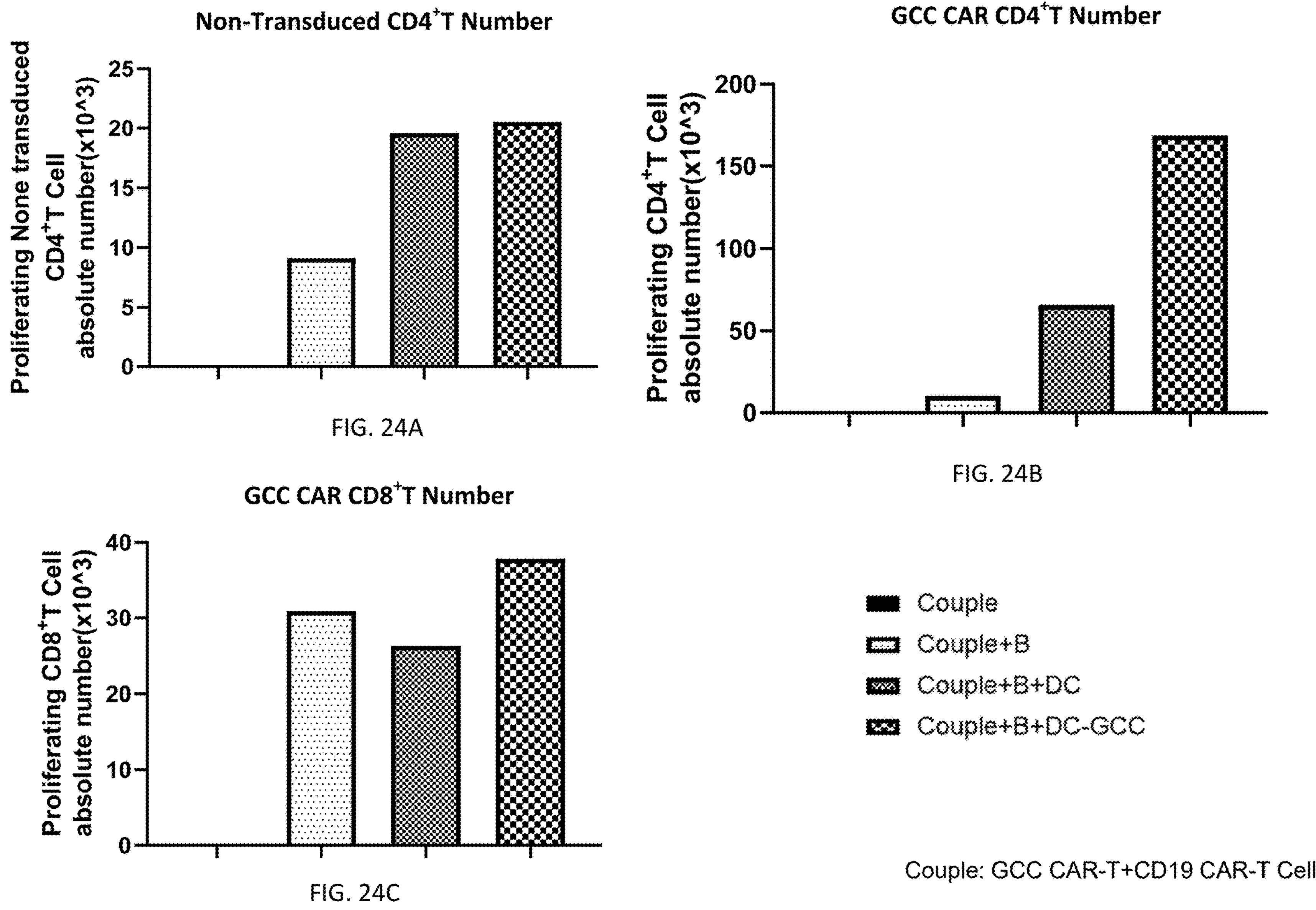
FIGS. 24A, 24B, and 24C show expansion of mixed CD19 CAR T and GCC CAR T cells after mixed with DCs transfected with LNP-GCC.

FIG. 24 shows expansion of mixed CD19 CAR T and GCC CAR T cells after mixing with DCs transfected with LNP-GCC. Twenty-four hours after the differentiated DC cells were transfected with LNP-GCC, they were mixed with CAR T cells including CD19 CAR T cells and GCC CAR T cells with or without the presence of B cells. Expansion analysis was performed. It was found that GCC CAR T cells showed significant proliferation, especially CD4+ T cells. This indicates that LNP-GCC enhanced expansion of solid tumor CAR T cells in CoupledCAR® system (e.g., CD19 CAR T cells and GCC CAR T cells).

FIG. 25 shows activation of mixed CAR19 CAR T and GCC CAR T cells after mixing with DCs transfected with LNP-GCC. It was found that GCC CAR T cells showed significant activation. This indicates that LNP-GCC enhanced activation of solid tumor CAR T cells in Coupled-CAR® system (e.g., CD19 CAR T cells and GCC CAR T cells).

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

The invention claimed is:

1. A method of enhancing expansion of T cells, the method comprising:

obtaining lipid particles comprising a polynucleotide encoding a solid tumor antigen;

contacting a population of dendritic cells (DCs) and a population of lymphocytes with the lipid particles, the population of lymphocytes comprising a first population of T cells comprising a CAR binding CD19 and a second population of T cells comprising a CAR binding the solid tumor antigen; and allowing expansion of the first and second population of T cells, wherein a level of the expansion of the first and second population of T cells is greater than a level of expansion of a first and a second population of T cells contacted with the population of DCs but without lipid particles.

2. The method of claim 1, wherein the tumor antigen comprises tMUC1, PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, CLDN 18.2, KISS1R, QRFPR, GPR119, CLDN6, UPK2, ADAM12, SLC45A3, ACPP, MUC21, MUC16, MS4A12, ALPP, CEA, EphA2, FAP, GPC3, IL13-Rα2, Mesothelin, PSMA, ROR1, VEGFR-II, GD2, FR-α, ErbB2, EpCAM, EGFRvIII, MAGE A4, EGFR, or a combination thereof.

3. The method of claim 2, wherein the polynucleotide encoding the antigen comprises transcribed RNA encapsulated in liposomes.

4. The method of claim 1, wherein the lipid particles comprise N-[1-(2,3-dioleyloxy) propyl]-N,N,N-trimethylammonium chloride (DOTMA), dioleoylphosphatidylethanolamine (DOPE), or a combination of DOTMA and cholesterol.

5. The method of claim 1, wherein the polynucleotide encodes SEQ ID NO: 1, and the CAR binding the solid tumor antigen comprises SEQ ID NO: 5 or 6.

6. The method of claim 1, wherein the lipid particles comprise lipid nanoparticles (LNPs).

7. The method of claim 1, wherein the lipid particles comprise a polynucleotide encoding a costimulatory signal-related molecule selected from the group consisting of anti-CD28, CD40L, anti-4-1BB, and agonists of CD28, CD40, or 4-1BB.

8. The method of claim 1, wherein the population of T cells comprises one or more dominant negative forms of an immune checkpoint molecule.

9. The method of claim 8, wherein the immune checkpoint molecule comprises PD-1, cytotoxic T lymphocyte antigen-4 (CTLA-4), B- and T-lymphocyte attenuator (BTLA), T-cell immunoglobulin mucin-3 (TIM-3), lymphocyte-activation protein 3 (LAG-3), T-cell immunoreceptor with Ig and ITIM domains (TIGIT), leukocyte-associated immunoglobulin-like receptor 1 (LAIR1), natural killer cell receptor 2B4 (2B4), or CD160.

10. The method of claim 1, wherein a ratio of the population of DCs to the population of T cells is from about 100:1 to about 1:100.

11. The method of claim 10, wherein the ratio of the population of DCs to the population of T cells is from about 1:1 to about 1:10.

12. The method of claim 1, wherein the contacting is performed in the presence of a cytokine comprising IL-2, IL-7, IL-15, IL-21, or a combination thereof.

13. The method of claim 1, wherein the first population of T cells or the second population of T cells comprises an intracellular signaling domain of a CD3-zeta (CD3ζ) chain, a CD28 signaling domain, a 4-1BB signaling domain, or a combination thereof.

14. The method of claim 1, wherein the first population of T cells or the second population of T cells has reduced expression of an endogenous TRAC gene.

15. The method of claim 1, wherein the contacting is performed for a time period ranging from about 1 day to about 10 days.

16. The method of claim 1, wherein the tumor antigen is GUCY2C.

17. The method of claim 1, wherein the tumor antigen is ACPP.

18. The method of claim 1, wherein the tumor antigen is TSHR.

19. The method of claim 1, wherein the contacting step comprises administering the population of DCs and the population of T cells to a subject simultaneously or sequentially via intravenous injection, intratumoral injection, or intraperitoneal injection.

* * * * *